US010448638B2

(12) United States Patent
Satchivi et al.

(10) Patent No.: US 10,448,638 B2
(45) Date of Patent: Oct. 22, 2019

(54) SYNERGISTIC WEED CONTROL FROM APPLICATIONS OF PYRIDINE CARBOXYLIC ACID HERBICIDES AND ALS INHIBITORS

(71) Applicant: Dow AgroSciences LLC, Indianapolis, IN (US)

(72) Inventors: Norbert M. Satchivi, Carmel, IN (US); Bryston L. Bangel, Camby, IN (US); Jennifer Lynn Ransberger, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 20 days.

(21) Appl. No.: 14/854,684

(22) Filed: Sep. 15, 2015

(65) Prior Publication Data

US 2016/0135457 A1     May 19, 2016

Related U.S. Application Data

(60) Provisional application No. 62/050,715, filed on Sep. 15, 2014.

(51) Int. Cl.
| | |
|---|---|
| *A01N 43/40* | (2006.01) |
| *A01N 43/54* | (2006.01) |
| *A01N 47/36* | (2006.01) |
| *A01N 43/50* | (2006.01) |
| *A01N 43/90* | (2006.01) |
| *A01N 43/653* | (2006.01) |

(52) U.S. Cl.
CPC .............. *A01N 43/40* (2013.01); *A01N 43/50* (2013.01); *A01N 43/54* (2013.01); *A01N 43/653* (2013.01); *A01N 43/90* (2013.01); *A01N 47/36* (2013.01)

(58) Field of Classification Search
CPC combination set(s) only.
See application file for complete search history.

(56) References Cited

U.S. PATENT DOCUMENTS

| | | | |
|---|---|---|---|
| 6,297,197 B1 | 10/2001 | Fields et al. | |
| 6,784,137 B2 | 8/2004 | Balko et al. | |
| 7,300,907 B2 | 11/2007 | Epp et al. | |
| 7,314,849 B2 | 1/2008 | Balko et al. | |
| 7,498,468 B2 | 3/2009 | Balko et al. | |
| 7,538,214 B2 | 5/2009 | Epp et al. | |
| 7,642,220 B2 | 1/2010 | Epp et al. | |
| 7,863,220 B2 | 1/2011 | Clark et al. | |
| 7,888,287 B2 | 2/2011 | Epp et al. | |
| 8,288,318 B2 | 10/2012 | Epp et al. | |
| 8,426,591 B2 | 4/2013 | Guenthenspberger et al. | |
| 8,536,331 B2 | 9/2013 | Eckelbarger et al. | |
| 8,609,592 B2 | 12/2013 | Guenthenspberger et al. | |
| 8,754,229 B2 | 6/2014 | Epp et al. | |
| 9,113,629 B2 | 8/2015 | Eckelbarger et al. | |
| 9,179,676 B2 * | 11/2015 | Hoffmann | C07D 417/04 |
| 9,521,847 B2 | 12/2016 | Satchivi et al. | |
| 10,231,451 B2 * | 3/2019 | Satchivi | C07D 405/04 |
| 2003/0114311 A1 | 6/2003 | Balko et al. | |
| 2007/0179059 A1 | 8/2007 | Epp et al. | |
| 2008/0045734 A1 | 2/2008 | Balko et al. | |
| 2008/0234262 A1 | 9/2008 | Zask et al. | |
| 2009/0048109 A1 | 2/2009 | Epp et al. | |
| 2009/0062121 A1 | 3/2009 | Satchivi et al. | |
| 2009/0088322 A1 | 4/2009 | Epp et al. | |
| 2009/0264429 A1 | 10/2009 | Apodaca et al. | |
| 2010/0137137 A1 | 6/2010 | Rosinger et al. | |
| 2010/0137138 A1 | 6/2010 | Rosinger et al. | |
| 2010/0179127 A1 | 7/2010 | Floersheim et al. | |
| 2010/0285959 A1 | 11/2010 | Armel et al. | |
| 2011/0105325 A1 | 5/2011 | Satchivi et al. | |
| 2011/0136666 A1 * | 6/2011 | Whittingham | A01N 43/54 |
| | | | 504/103 |
| 2011/0281873 A1 | 11/2011 | Chiang et al. | |
| 2012/0015811 A1 | 1/2012 | Dave et al. | |
| 2012/0115724 A1 | 5/2012 | Whittingham et al. | |
| 2012/0157314 A1 | 6/2012 | Ahrens et al. | |
| 2012/0184435 A1 | 7/2012 | Bristow et al. | |
| 2012/0190548 A1 | 7/2012 | Eckelbarger et al. | |
| 2012/0190549 A1 | 7/2012 | Eckelbarger | |
| 2012/0288492 A1 | 11/2012 | Kuo et al. | |
| 2012/0292905 A1 | 11/2012 | Slot | |
| 2013/0310358 A1 | 11/2013 | Coats et al. | |
| 2013/0345240 A1 | 12/2013 | Whitten et al. | |
| 2014/0274695 A1 | 9/2014 | Eckelbarger et al. | |
| 2014/0274701 A1 | 9/2014 | Eckelbarger et al. | |
| 2015/0005165 A1 | 1/2015 | Hoffmann et al. | |

FOREIGN PATENT DOCUMENTS

| | | |
|---|---|---|
| CA | 2842830 A1 | 1/2013 |
| WO | 2003011853 A1 | 2/2003 |

(Continued)

OTHER PUBLICATIONS

International Search Report and Written Opinion of the EP International Searching Authority from International Application No. PCT/EP2012/064519 dated Sep. 28, 2012.

(Continued)

*Primary Examiner* — John Pak
(74) *Attorney, Agent, or Firm* — Meunier Carlin & Curfman, LLC

(57) ABSTRACT

Disclosed herein are herbicidal compositions comprising a herbicidally effective amount of (a) a pyridine carboxylic acid herbicide or an agriculturally acceptable N-oxide, salt, or ester thereof, and (b) an acetolactate synthase (ALS) inhibitor or an agriculturally acceptable salt or ester thereof. Also disclosed herein are methods of controlling undesirable vegetation which comprise applying to vegetation or an area adjacent the vegetation or applying to soil or water to prevent the emergence or growth of vegetation (a) a pyridine carboxylic acid herbicide or an agriculturally acceptable N-oxide, salt, or ester thereof, and (b) an acetolactate synthase (ALS) inhibitor or an agriculturally acceptable salt or ester thereof, wherein (a) and (b) are each added in an amount sufficient to provide a herbicidal effect.

34 Claims, No Drawings

(56) References Cited

FOREIGN PATENT DOCUMENTS

| | | |
|---|---|---|
| WO | 2005063721 A1 | 7/2005 |
| WO | 2006121648 A2 | 11/2006 |
| WO | 2007080382 A1 | 7/2007 |
| WO | 2007082076 A1 | 7/2007 |
| WO | 2007082098 A2 | 7/2007 |
| WO | 2009007751 A2 | 1/2009 |
| WO | 2009023438 A1 | 2/2009 |
| WO | 2009029735 A1 | 3/2009 |
| WO | 2009081112 A2 | 7/2009 |
| WO | 2010060581 A2 | 6/2010 |
| WO | 2010092339 A1 | 8/2010 |
| WO | 2009138712 A3 | 9/2010 |
| WO | 2010125332 A1 | 11/2010 |
| WO | 2011080568 A2 | 7/2011 |
| WO | 2012080187 A1 | 6/2012 |
| WO | 2012149528 A1 | 11/2012 |
| WO | 2013003740 A1 | 1/2013 |
| WO | 2013014165 A1 | 1/2013 |

OTHER PUBLICATIONS

International Search Report and Written Opinion issued in International Application No. PCT/US2014/024745 dated Jul. 7, 2014.
International Search Report and Written Opinion issued in International Application No. PCT/US2014/024749, dated Jul. 10, 2014.
International Search Report and Written Opinion issued in International Application No. PCT/US2014/024752 dated Jul. 7, 2014.
Abell, "Target-Site Directed Herbicide Design in, pest control with enhanced environmental safety 15-37", 1993.
Knight, et al., "Annual Review of Phytopathology", 1997.
Ruegg, et al., "Weed Research", 2006.
Pubchem. Substance Record for SID 172846318. Deposit Date: Mar. 7, 2013. [retrieved on Dec. 1, 2015]. Retrieved from the Internet, <URL:https://pubchem.ncbl.nlm.nih.gov/substance/172846318/version/1#section=Top>. entire document.
International Search Report and Written Opinion issued in related International Application No. PCT/US2015/050122 dated Jul. 5, 2016.
International Search Report and Written Opinion, issued in International Application No. PCT/US15/50203 dated Jan. 14, 2016.
International Search Report and Written Opinion, issued in International Application No. PCT/US15/50205 dated Jan. 14, 2016.
International Search Report and Written Opinion, issued in International Application No. PCT/US15/50209 dated Jan. 14, 2016.
International Search Report and Written Opinion dated Jul. 14, 2014 in related PCT Application No. PCT/US2014/024388 (10 pages).
International Search Report and Written Opinion dated Dec. 29, 2015 in related PCT Application No. PCT/US2015/050190 (8 pages).
Extended European Search Report dated Sep. 12, 2016 in related Application No. EP 2970186 (5 pages).
Extended European Search Report dated Oct. 14, 2016 in related Application No. EP 2970187 (5 pages).
Extended European Search Report dated Apr. 3, 2018 in related European Application 15841613 (5 pages).

\* cited by examiner

SYNERGISTIC WEED CONTROL FROM APPLICATIONS OF PYRIDINE CARBOXYLIC ACID HERBICIDES AND ALS INHIBITORS

CROSS REFERENCE TO RELATED APPLICATIONS

This application claims benefit of U.S. Provisional Patent Application No. 62/050,715, filed Sep. 15, 2014, which is hereby incorporated herein by reference in its entirety.

FIELD OF THE DISCLOSURE

The present disclosure relates to herbicidal compositions comprising a herbicidally effective amount of (a) a pyridine carboxylic acid herbicide or an agriculturally acceptable N-oxide, salt, or ester thereof and (b) an acetolactate synthase (ALS) inhibitor or an agriculturally acceptable salt or ester thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Disclosed herein are herbicidal compositions. The herbicidal compositions can comprise a herbicidally effective amount of (a) a pyridine carboxylic acid herbicide or an agriculturally acceptable N-oxide, salt, or ester thereof and (b) an acetolactate synthase (ALS) inhibitor or an agriculturally acceptable salt or ester thereof. In some embodiments, (a) and (b) can be provided in a synergistic herbicidally effective amount. In some embodiments, the weight ratio of (a) to (b) can be from 1:3400 to 1200:1 (e.g., from 1:1000 to 1200:1, from 1:1700 to 600:1, from 1:280 to 160:1, from 1:200 to 160:1, from 1:7.5 to 160:1, from 1:10 to 16:1, from 1:5 to 5:1, from 2:1 to 16:1, or from 4:1 to 8:1).

The pyridine carboxylic acid herbicide can comprise a compound defined by Formula (I)

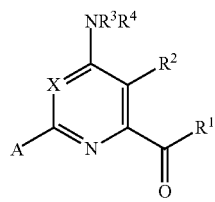

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups A1 to A36

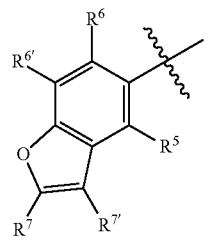

A1

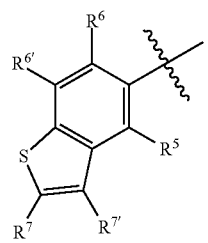

A2

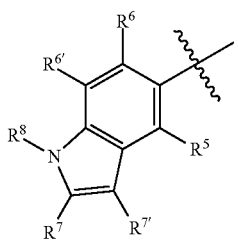

A3

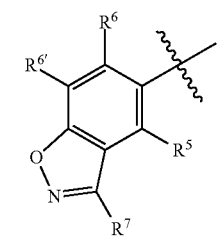

A4

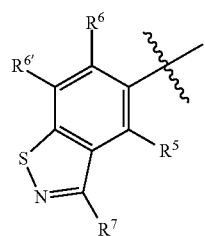 A5
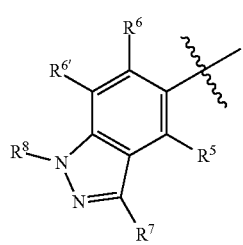 A6
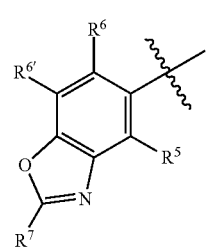 A7
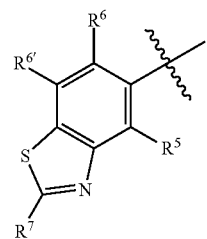 A8
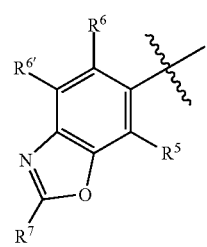 A9
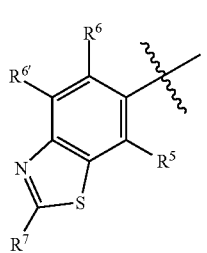 A10
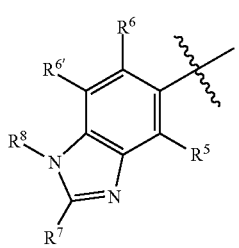 A11
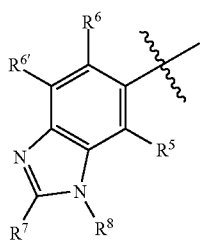 A12
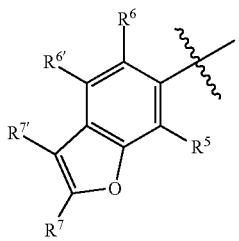 A13
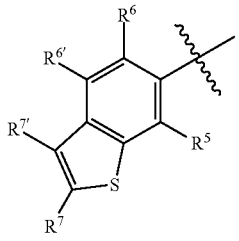 A14
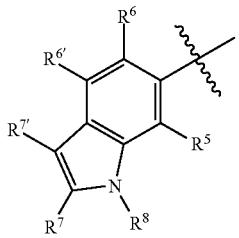 A15
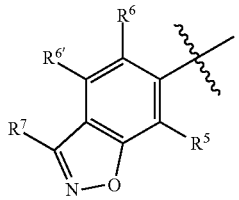 A16

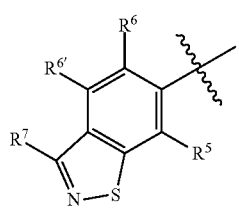
A17
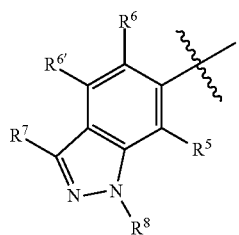
A18
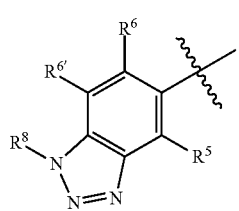
A19
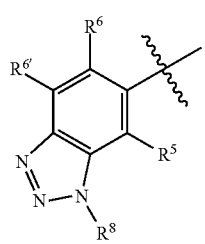
A20
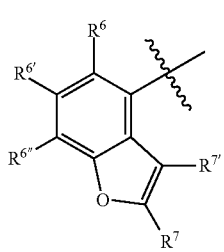
A21
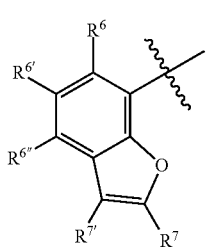
A22
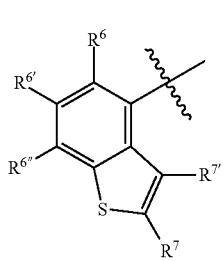
A23
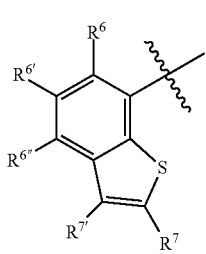
A24
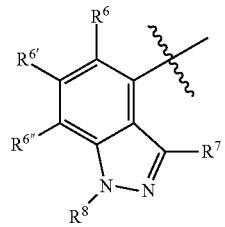
A25
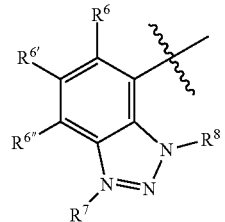
A26
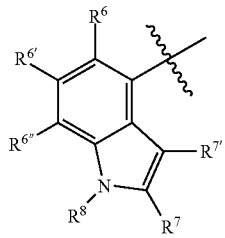
A27
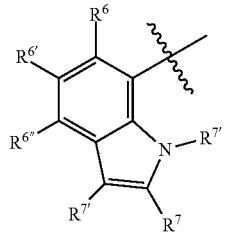
A28
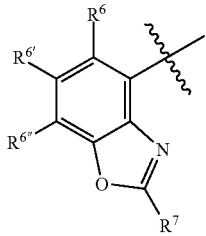
A29

-continued

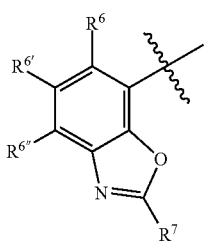

A30

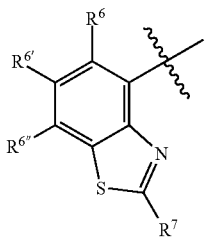

A31

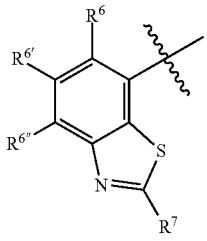

A32

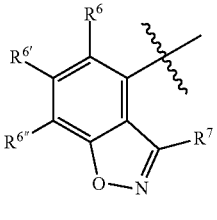

A33

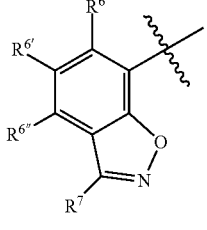

A34

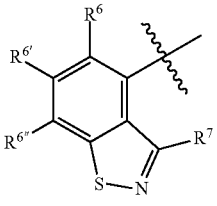

A35

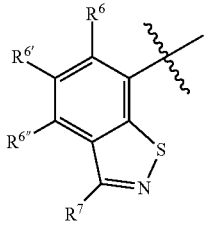

A36

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In certain embodiments, the pyridine carboxylic acid herbicide can comprise a compound defined by Formula (II):

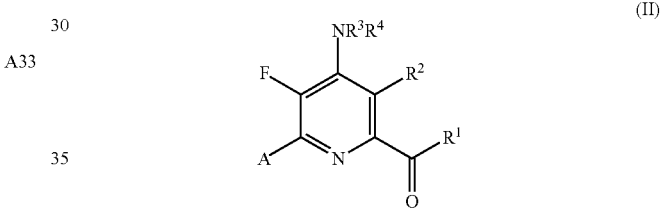

(II)

wherein $R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $—CR^{17}=CR^{18}—SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$, alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen. $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

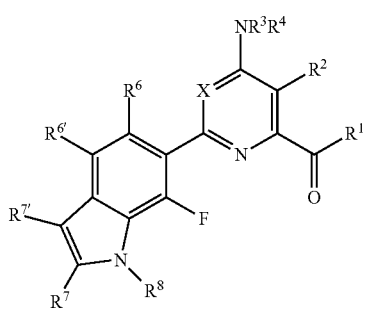

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1'}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $—CR^{17}=CR^{18}—SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, X is N, CH or CF. In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can include 4-amino-3-chloro-5-fluoro-6-(7-fluoro-1H-indol-6-yl) picolinic acid, or an agriculturally acceptable N-oxide, salt, or ester thereof.

In some embodiments, (b) can comprise a triazolopyrimidine sulfonamide herbicide. In certain embodiments, (b) can include florasulam, cloransulam, diclosulam, flumetsulam, metosulam, penoxsulam, pyroxsulam, agriculturally acceptable salts or esters thereof, or combinations thereof.

In some embodiments, (b) can comprise an imidazolinone herbicide. In certain embodiments, (b) can include imazamethabenz, imazamox, imazapic, imazapyr, imazaquin, imazethapyr, agriculturally acceptable salts or esters thereof, or combinations thereof.

In some embodiments, (b) can comprise a pyrimidinyl oxybenzoate herbicide. In certain embodiments, (b) can include bispyribac, pyribenzoxim, pyriftalid, pyriminobac, pyrimisulfan, pyrithiobac, agriculturally acceptable salts or esters thereof, or combinations thereof.

In some embodiments, (b) can comprise a sulfonylaminocarbonyl triazolinone herbicide. In certain embodiments, (b) can include flucarbazone, propoxycarbazone, thiencarbazone, agriculturally acceptable salts or esters thereof, or combinations thereof.

In some embodiments, (b) can comprise a sulfonylurea herbicide. In certain embodiments, (b) can include amidosulfuron, azimsulfuron, bensulfuron, chlorimuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, triasulfuron, tribenuron, thifensulfuron, trifloxysulfuron, tritosulfuron, agriculturally acceptable salts or esters thereof, or combinations thereof. The composition can further comprise an additional pesticide, a herbicidal safener, an agriculturally acceptable adjuvant or carrier, or a combination thereof. The composition can be provided as a herbicidal concentrate.

The present disclosure also relates to methods of controlling undesirable vegetation which comprise applying to vegetation or an area adjacent the vegetation or applying to soil or water to prevent the emergence or growth of vegetation a herbicidally effective amount of (a) a pyridine carboxylic acid herbicide or an agriculturally acceptable N-oxide, salt, or ester thereof and (b) an acetolactate synthase (ALS) inhibitor or an agriculturally acceptable salt or ester thereof. In some embodiments, (a) and (b) are provided in a synergistically effective amount. In some embodiments, (a) and (b) are applied simultaneously. In some embodiments, (a) and (b) are applied post-emergence of the undesirable vegetation.

In some embodiments, (a) can comprise a pyridine carboxylic acid herbicide described above. In certain embodiments, (a) can comprise 4-amino-3-chloro-5-fluoro-6-(7-fluoro-1H-indol-6-yl) picolinic acid or an agriculturally acceptable N-oxide, salt, or ester thereof. In some embodiments, (b) can comprise a triazolopyrimidine sulfonamide herbicide. In certain embodiments, (b) can include florasulam, cloransulam, diclosulam, flumetsulam, metosulam, penoxsulam, pyroxsulam, agriculturally acceptable salts or esters thereof, or combinations thereof. In some cases, (a) can be applied in an amount of from 0.1 grams acid equivalent per hectare (g ae/ha) to 300 g ae/ha (e.g., from 0.5 g ae/ha to 300 g ae/ha, from 5 g ae/ha to 40 g ae/ha, or from 5 g ae/ha to 15 g ae/ha) and/or (b) can be applied in an amount of from 0.25 grams active ingredient per hectare (g ai/ha) to 1000 g ai/ha (e.g., from 0.25 g ai/ha to 7.5 g ai/ha). In some cases, (a) and (b) can be applied in a weight ratio of from 1:2000 to 1200:1 (e.g., from 1:1000 to 1200:1, from 1:200 to 160:1, from 1:50 to 120:1, from 1:7.5 to 160:1, from 1:10 to 16:1, from 1:3.8 to 16:1, from 1:5 to 6:1, from 2:1 to 16:1, or from 4:1 to 8:1).

In some embodiments, (a) can comprise a pyridine carboxylic acid herbicide described above. In certain embodiments, (a) can comprise 4-amino-3-chloro-5-fluoro-6-(7-fluoro-1H-indol-6-yl) picolinic acid or an agriculturally acceptable N-oxide, salt, or ester thereof. In some embodiments, (b) can comprise an imidazolinone herbicide. In certain embodiments, (b) can include imazamethabenz, imazamox, imazapic, imazapyr, imazaquin, or imazethapyr, or agriculturally acceptable salts or esters thereof. In some cases, (a) can be applied in an amount of from 0.1 g ae/ha to 300 g ae/ha (e.g., from 0.5 g ae/ha to 300 g ae/ha, from 5 g ae/ha to 40 g ae/ha, or from 5 g ae/ha to 15 g ae/ha) and/or (b) can be applied in an amount of from 5 g ai/ha to 1700 g ai/ha (e.g., from 10 g ai/ha to 1000 g ai/ha). In some cases, (a) and (b) can be applied in a weight ratio of from 1:3400 to 60:1 (e.g., from 1:1400 to 60:1, from 1:440 to 30:1, from 1:280 to 17:1, or from 1:10 to 5:1).

In some embodiments, (a) can comprise a pyridine carboxylic acid herbicide described above. In certain embodiments, (a) can comprise 4-amino-3-chloro-5-fluoro-6-(7-fluoro-1H-indol-6-yl) picolinic acid or an agriculturally acceptable N-oxide, salt, or ester thereof. In some embodiments, (b) can comprise a pyrimidinyl oxybenzoate herbicide. In certain embodiments, (b) can include bispyribac, pyribenzoxim, pyriftalid, pyriminobac, pyrimisulfan, or pyrithiobac, or agriculturally acceptable salts or esters thereof. In some cases, (a) can be applied in an amount of from 0.1 g ae/ha to 300 g ae/ha (e.g., from 0.5 g ae/ha to 300 g ae/ha, from 5 g ae/ha to 40 g ae/ha, or from 5 g ae/ha to 15 g ae/ha) and/or (b) can be applied in an amount of from 5 g ai/ha to 300 g ai/ha (e.g., from 10 g ai/ha to 200 g ai/ha). In some cases, (a) and (b) can be applied in a weight ratio of from 1:600 to 60:1 (e.g., from 1:140 to 40:1, from 1:120 to 20:1, from 1:15 to 4.3:1, or from 1:10 to 5:1).

In some embodiments, (a) can comprise a pyridine carboxylic acid herbicide described above. In certain embodiments, (a) can comprise 4-amino-3-chloro-5-fluoro-6-(7-fluoro-1H-indol-6-yl) picolinic acid or an agriculturally acceptable N-oxide, salt, or ester thereof. In some embodiments, (b) can comprise a sulfonylaminocarbonyl triazolinone herbicide. In certain embodiments, (b) can include flucarbazone, propoxycarbazone, or thiencarbazone, or agriculturally acceptable salts or esters thereof. In some cases, (a) can be applied in an amount of from 0.1 g ae/ha to 300 g ae/ha (e.g., from 0.5 g ae/ha to 300 g ae/ha, from 5 g ae/ha to 40 g ae/ha, or from 5 g ae/ha to 15 g ae/ha) and/or (b) can be applied in an amount of from 2.5 g ai/ha to 300 g ai/ha (e.g., from 2.5 g ai/ha to 100 g ai/ha). In some cases, (a) and (b) can be applied in a weight ratio of from 1:600 to 120:1 (e.g., from 1:140 to 80:1, from 1:60 to 80:1, from 1:7.5 to 10:1, or from 1:5 to 1:1).

In some embodiments, (b) can comprise a sulfonylurea herbicide. In certain embodiments, (b) can include amidosulfuron, azimsulfuron, bensulfuron, chlorimuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, triasulfuron, tribenuron, thifensulfuron, trifloxysulfuron, tritosulfuron, or agriculturally acceptable salts or esters thereof. In some cases, (a) can be applied in an amount of from 0.1 g ae/ha to 300 g ae/ha (e.g., from 0.5 g ae/ha to 300 g ae/ha, from 5 g ae/ha to 40 g ae/ha, or from 5 g ae/ha to 15 g ae/ha) and/or (b) can be applied in an amount of from 0.75 g ai/ha to 200 g ai/ha (e.g., from 0.75 g ai/ha to 140 g ai/ha). In some cases, (a) and (b) can be applied in a weight ratio of from 1:400 to 400:1 (e.g., from 1:175 to 70:1, from 1:120 to 60:1, from 1:10 to 5:1, or from 1:8.75 to 2:1).

The description below sets forth details of one or more embodiments of the present disclosure. Other features, objects, and advantages will be apparent from the description and from the claims.

DETAILED DESCRIPTION

The present disclosure relates to herbicidal compositions comprising a herbicidally effective amount of (a) a pyridine carboxylic acid herbicide or an agriculturally acceptable N-oxide, salt, or ester thereof and (b) an acetolactate synthase (ALS) inhibitor or an agriculturally acceptable salt or ester thereof. The present disclosure also relates to methods for controlling undesirable vegetation.

I. DEFINITIONS

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the terms "herbicide" and "herbicidal active ingredient" refer to an active ingredient that kills, controls, or otherwise adversely modifies the growth of vegetation, particularly undesirable vegetation, such as weeds, when applied in an appropriate amount.

As used herein, a "herbicidally effective amount" refers to an amount of an active ingredient that causes a "herbicidal effect," i.e., an adversely modifying effect including, for instance, a deviation from natural growth or development, killing, regulation, desiccation, growth inhibition, growth reduction, and retardation.

As used herein, applying a herbicide or herbicidal composition refers to delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, the terms "crops" and "vegetation" can include, for instance, dormant seeds, germinant seeds, emerging seedlings, plants emerging from vegetative propagules, immature vegetation, and established vegetation.

As used herein, immature vegetation refers to small vegetative plants prior to reproductive stage, and mature vegetation refers to vegetative plants during and after the reproductive stage.

As used herein, the term "acyl" refers to a group of formula —C(O)R, where R is hydrogen, alkyl (e.g., $C_1$-$C_{10}$ alkyl), haloalkyl ($C_1$-$C_8$ haloalkyl), alkenyl ($C_2$-$C_8$ alkenyl), haloalkenyl (e.g., $C_2$-$C_8$ haloalkenyl), alkynyl (e.g., $C_2$-$C_8$ alkynyl), alkoxy ($C_1$-$C_8$ alkoxy), haloalkoxy ($C_1$-$C_8$ alkoxy), aryl, or heteroaryl, arylalkyl ($C_7$-$C_{10}$ arylalkyl), as defined below, where "C(O)" or "CO" is short-hand notation for C=O. In some embodiments, the acyl group can be a $C_1$-$C_6$ acyl group (e.g., a formyl group, a $C_1$-$C_5$ alkylcarbonyl group, or a $C_1$-$C_5$ haloalkylcarbonyl group). In some embodiments, the acyl group can be a $C_1$-$C_3$ acyl group (e.g., a formyl group, a $C_1$-$C_3$ alkylcarbonyl group, or a $C_1$-$C_3$ haloalkylcarbonyl group).

As used herein, the term "alkyl" refers to saturated, straight-chained or branched saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkenyl" refers to unsaturated, straight-chained, or branched hydrocarbon moieties containing a double bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, i-methyl-1-propenyl, 2-methyl-1-propenyl, i-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure —CH=CH—CH$_3$; and 2-propenyl refers to a group with the structure —CH$_2$—CH=CH$_2$. Alkenyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

The term "haloalkenyl." as used herein, refers to an alkenyl group, as defined above, which is substituted by one or more halogen atoms.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkoxy" refers to a group of the formula R—O—, where R is unsubstituted or substituted alkyl as defined above. Unless otherwise specified, alkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, the term "haloalkoxy" refers to a group of the formula R—O—, where R is unsubstituted or substituted haloalkyl as defined above. Unless otherwise specified, haloalkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) haloalkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, and 1,1,1-trifluoroprop-2-oxy.

As used herein, the term "alkylthio" refers to a group of the formula R—S—, where R is unsubstituted or substituted alkyl as defined above. Unless otherwise specified, alkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-di-methylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methyl-pentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio.

As used herein, the term "haloalkylthio" refers to an alkylthio group as defined above wherein the carbon atoms are partially or entirely substituted with halogen atoms. Unless otherwise specified, haloalkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein, the term "alkylcarbonyl" refers to an unsubstituted or substituted alkyl group bonded to a carbonyl group. $C_1$-$C_3$ alkylcarbonyl and $C_1$-$C_3$ haloalkylcarbonyl refer to groups wherein a $C_1$-$C_3$ unsubstituted or substituted alkyl or haloalkyl group is bonded to a carbonyl group (the group contains a total of 2 to 4 carbon atoms).

As used herein, the term "alkoxycarbonyl" refers to a group of the formula

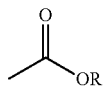

wherein R is unsubstituted or substituted alkyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

As used herein, the term "alkylamino" refers to an amino group substituted with one or two unsubstituted or substituted alkyl groups, which may be the same or different.

As used herein, the term "haloalkylamino" refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ unsubstituted or substituted alkyl, and $C_1$-$C_6$ dialkylaminocarbonyl refers to a group of the formula $R_2$NC(O)— wherein each R is independently $C_1$-$C_6$ unsubstituted or substituted alkyl.

As used herein, the term "alkylcarbamyl" refers to a carbamyl group substituted on the nitrogen with an unsubstituted or substituted alkyl group.

As used herein, the term "alkylsulfonyl" refers to a group of the formula

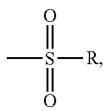

where R is unsubstituted or substituted alkyl.

As used herein, the term "carbamyl" (also referred to as carbamoyl and aminocarbonyl) refers to a group of the formula

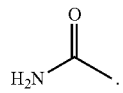

As used herein, the term "dialkylphosphonyl" refers to a group of the formula

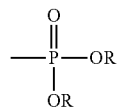

where R is independently unsubstituted or substituted alkyl in each occurrence.

As used herein, $C_1$-$C_6$ trialkylsilyl refers to a group of the formula —$SiR_3$ wherein each R is independently a $C_1$-$C_6$ unsubstituted or substituted alkyl group (the group contains a total of 3 to 18 carbon atoms).

As used herein, Me refers to a methyl group; OMe refers to a methoxy group; and i-Pr refers to an isopropyl group.

As used herein, the term "halogen" including derivative terms such as "halo" refers to fluorine, chlorine, bromine and iodine.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted. e.g., in plants, water, or soil, to the corresponding carboxylic acid which, depending on the pH, may be in the dissociated or undissociated form.

Compounds described herein can include N-oxides. Pyridine N-oxides can be obtained by oxidation of the corresponding pyridines. Suitable oxidation methods are described, for example, in Houben-Weyl, *Methoden der organischen Chemie* [*Methods in organic chemistry*], expanded and subsequent volumes to the 4th edition, volume E 7b, p. 565 f.

Pyridine Carboxylic Acid Herbicides

Compositions and methods of the present disclosure can include a pyridine carboxylic acid herbicide defined by Formula (I)

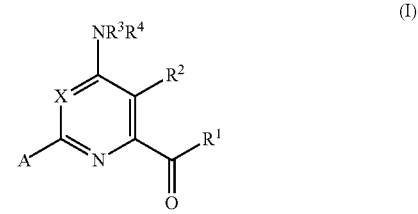

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1''}$ or $NR^{1''}R^{1'''}$, wherein $R^{1''}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

R³ and R⁴ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or R³ and R⁴ taken together with N is a 5- or 6-membered saturated ring, or R³ and R⁴ taken together represent =CR³'(R⁴'), wherein R³' and R⁴' are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, R³' and R⁴' taken together with =C represent a 5- or 6-membered saturated ring;

A is one of groups A1 to A36

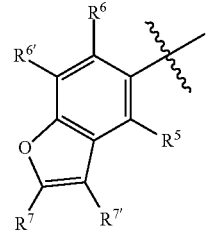

A1

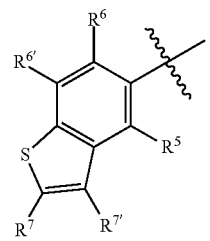

A2

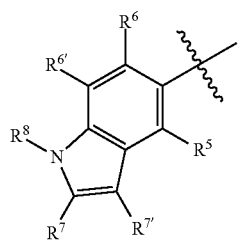

A3

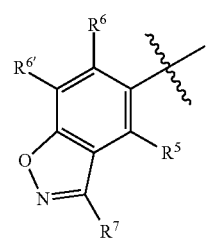

A4

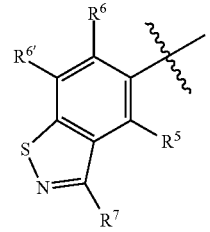

A5

-continued

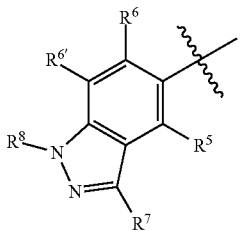

A6

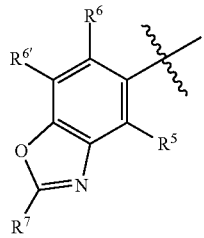

A7

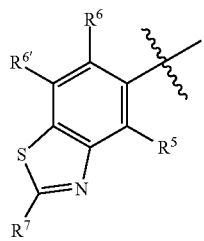

A8

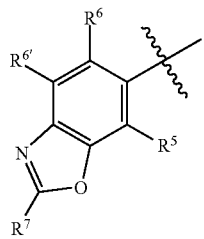

A9

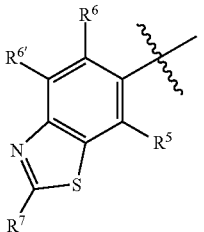

A10

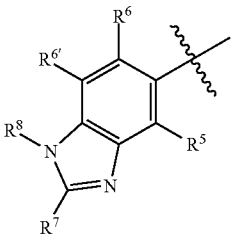

A11

-continued
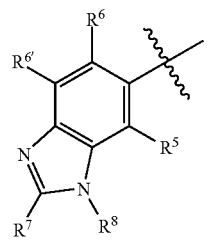 A12
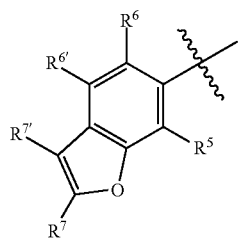 A13
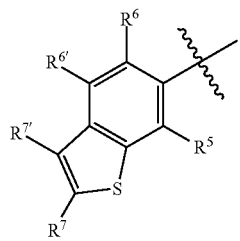 A14
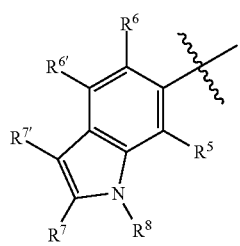 A15
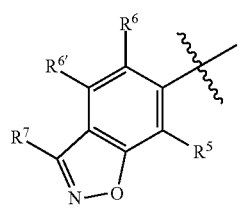 A16
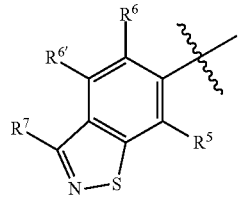 A17
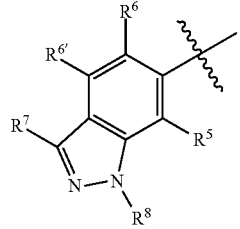 A18
-continued
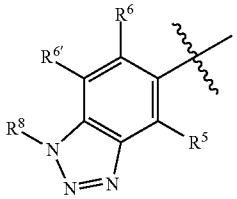 A19
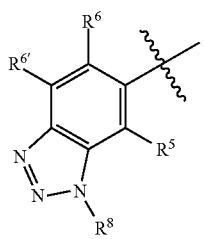 A20
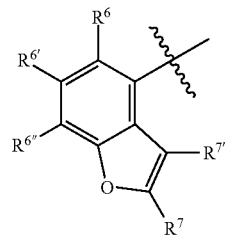 A21
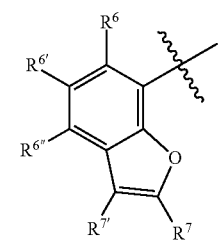 A22
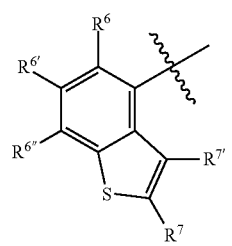 A23
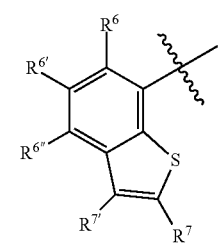 A24

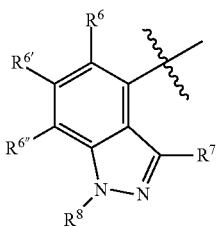 A25

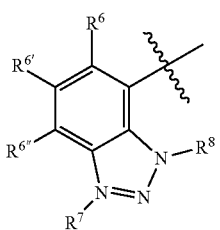 A26

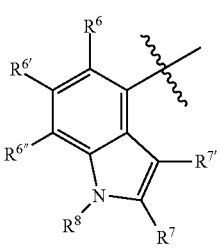 A27

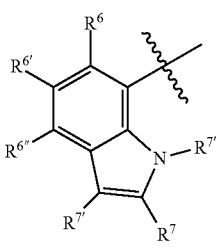 A28

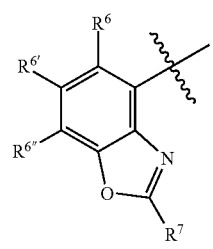 A29

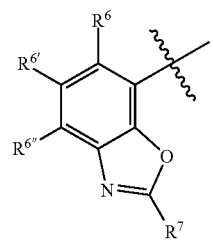 A30

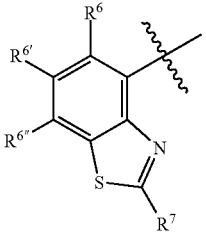 A31

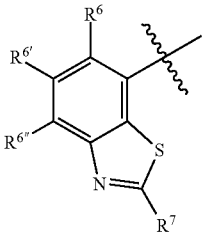 A32

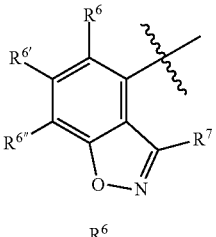 A33

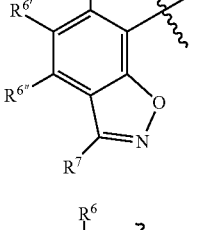 A34

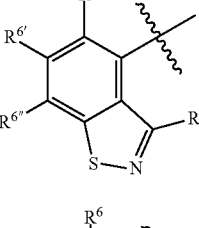 A35

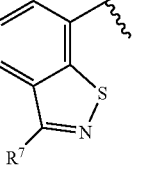 A36

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In some embodiments, $R^{1'}$ is hydrogen or $C_1$-$C_8$ alkyl. In some embodiments, $R^{1'}$ is hydrogen.

In some embodiments, $R^2$ is halogen, $C_1$-$C_4$ alkyl, $C_1$-$C_4$ haloalkyl, $C_2$-$C_4$ alkynyl, $C_2$-$C_4$-alkenyl, $C_2$-$C_4$ haloalkenyl, $C_1$-$C_4$-alkoxy, or $C_1$-$C_4$ haloalkoxy. In some embodiments, $R^2$ is halogen, $C_2$-$C_4$-alkenyl, $C_2$-$C_4$ haloalkenyl, or $C_1$-$C_4$-alkoxy. In some embodiments, $R^2$ is halogen. In some embodiments, $R^2$ is $C_2$-$C_4$-alkenyl or $C_2$-$C_4$ haloalkenyl. In some embodiments, $R^2$ is $C_1$-$C_4$ alkoxy. In some embodiments, $R^2$ is Cl, OMe, vinyl, or 1-propenyl. In some embodiments, $R^2$ is Cl. In some embodiments, $R^2$ is OMe. In some embodiments, $R^2$ is vinyl or 1-propenyl.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $R^3$ and $R^4$ taken together represent $=CR^{3'}(R^{4'})$, wherein $R^{1'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_1$-$C_6$ alkoxy or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, or $C_1$-$C_3$ haloalkylcarbonyl. In some embodiments, at least one of $R^3$ and $R^4$ are hydrogen. In some embodiments, $R^3$ and $R^4$ are both hydrogen.

In some embodiments, X is N, CH or CF. In some embodiments, X is N. In some embodiments, X is CH. In some embodiments, X is CF. In other embodiments, X is $C-CH_3$.

In some embodiments, A is A1, A2, A3, A4, A5, A6, A7, A8, A9, A10, A11, A12, A13, A14, A15, A16, A17, A18, A19, or A20. In other embodiments, A is one of A21, A22, A23, A24, A25, A26, A27, A28, A29, A30, A31, A32, A33, A34, A35, and A36.

In some embodiments, A is one of groups A1, A2, A3, A7, A8, A9, A10, A13, A14, and A15. In some embodiments, A is one of groups A1, A2, A3, A13, A14, and A15. In some embodiments, A is one of groups A13, A14, and A15. In some embodiments, A is A15.

In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, or amino. In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, or amino. In some embodiments, $R^5$ is hydrogen, halogen, $C_1$-$C_4$ alkyl or $C_1$-$C_4$ alkoxy. In some embodiments, $R^5$ is hydrogen or F. In some embodiments, $R^5$ is hydrogen.

In other embodiments, $R^5$ is F.

In some embodiments, $R^6$ is hydrogen, halogen, $C_1$-$C_4$ alkyl, $C_1$-$C_4$ haloalkyl, $C_1$-$C_3$ alkoxy, or $C_1$-$C_3$ haloalkoxy. In some embodiments, $R^6$ is hydrogen or fluorine. In some embodiments, $R^6$ is hydrogen. In some embodiments, $R^6$ is fluorine.

In some embodiments, $R^{6'}$ is hydrogen or halogen. In some embodiments, $R^{6'}$ is hydrogen, F, or Cl. In some embodiments, $R^{6'}$ is hydrogen or F. In some embodiments, $R^{6'}$ is hydrogen.

In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In some embodiments, $R^{6''}$ is hydrogen. In some embodiments, $R^{6''}$ is halogen. In some embodiments, $R^{6''}$ is $C_1$-$C_4$ alkyl. In some embodiments, $R^{6''}$ is $C_1$-$C_4$ haloalkyl. In some embodiments, $R^{6''}$ is cyclopropyl. In some embodiments, $R^{6''}$ is $C_2$-$C_4$ alkynyl. In some embodiments, $R^{6''}$ is CN. In some embodiments, $R^{6''}$ is $NO_2$.

In some embodiments:

X is N, CH, CF, CCl, or CBr;

$R^1$ is $OR^{1'}$, wherein $R^{1'}$ is hydrogen or $C_1$-$C_4$ alkyl;

$R^2$ is chlorine;

$R^3$ and $R^4$ are hydrogen;

A is A1, A2, A3, A4, A5, A6, A7, A8, A9, A10, A11, A12, A13, A14, A15, A16, A17, A18, A19, or A20;

$R^5$ is hydrogen, halogen, OH, amino, CN, $C_1$-$C_3$ alkyl, $C_1$-$C_3$ alkoxy, $C_1$-$C_3$ alkylamino, or cyclopropyl;

$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;

$R^7$ and $R^{7''}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and $R^8$ is hydrogen, $C_1$-$C_3$ alkyl, phenyl, or $C_1$-$C_3$ alkylcarbonyl.

In some embodiments, $R^2$ is halogen, $C_2$-$C_4$-alkenyl, $C_2$-$C_4$ haloalkenyl, or $C_1$-$C_4$-alkoxy; $R^3$ and $R^4$ are both hydrogen; and X is N, CH, or CF.

In some embodiments, $R^2$ is halogen; $R^3$ and $R^4$ are both hydrogen; and X is N, CH, or CF.

In some embodiments, $R^2$ is $C_2$-$C_4$-alkenyl or $C_2$-$C_4$ haloalkenyl; $R^3$ and $R^4$ are both hydrogen; and X is N, CH, or CF.

In some embodiments, $R^2$ is $C_1$-$C_4$-alkoxy; $R^3$ and $R^4$ are both hydrogen; and X is N, CH, or CF.

In some embodiments, $R^2$ is halogen, $C_2$-$C_4$-alkenyl, $C_2$-$C_4$ haloalkenyl, or $C_1$-$C_4$-alkoxy;

$R^3$ and $R^4$ are both hydrogen; X is N, CH, or CF; $R^5$ is hydrogen or F; $R^6$ is hydrogen or F; $R^{6'}$ is hydrogen; $R^{6''}$, if applicable to the relevant A group, is hydrogen or halogen; and $R^7$ and $R^{7'}$, if applicable to the relevant A group, are independently hydrogen or halogen.

In some embodiments, $R^2$ is halogen, $C_1$-$C_4$-alkoxy, or $C_2$-$C_4$-alkenyl; $R^3$ and $R^4$ are hydrogen; X is N, CH, or CF; and A is one of groups A1 to A20.

In some embodiments, $R^2$ is chlorine; $R^3$ and $R^4$ are hydrogen; X is N, CH, or CF; A is one of groups A1 to A20; $R^5$ is hydrogen or F; $R^6$ and $R^{6'}$ are independently hydrogen or F; and $R^7$ and $R^{7'}$, if applicable to the relevant A group, are independently hydrogen, halogen, $C_1$-$C_4$ alkyl, or $C_1$-$C_4$ haloalkyl.

In some embodiments, $R^2$ is chlorine, methoxy, vinyl, or 1-propenyl; $R^3$ and $R^4$ are hydrogen; and X is N, CH, or CF.

In some embodiments, $R^2$ is chlorine; $R^3$ and $R^4$ are hydrogen; and X is N, CH, or CF.

In some embodiments, $R^2$ is vinyl or 1-propenyl; $R^3$ and $R^4$ are hydrogen; and X is N, CH, or CF.

In some embodiments, $R^2$ is methoxy; $R^3$ and $R^4$ are hydrogen; and X is N, CH, or CF.

In some embodiments, $R^2$ is chlorine; $R^3$ and $R^4$ are hydrogen; and X is N.

In some embodiments, $R^2$ is chlorine; $R^3$ and $R^4$ are hydrogen; and X is CH.

In some embodiments, $R^2$ is chlorine; $R^3$ and $R^4$ are hydrogen; and X is CF.

In some embodiments, $R^2$ is chlorine; $R^3$ and $R^4$ are hydrogen; X is CF; A is one of A1, A2, A3, A7, A8, A9, A10, A13, A14, or A15; $R^5$ is F; and $R^6$ is H.

In some embodiments, $R^2$ is chlorine, methoxy, vinyl, or 1-propenyl; $R^3$ and $R^4$ are hydrogen; X is N, CH, or CF; and A is one of A21-A36.

In some embodiments, $R^2$ is chlorine, methoxy, vinyl, or 1-propenyl; $R^3$ and $R^4$ are hydrogen; X is CF; and A is one of

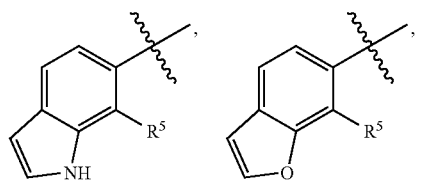
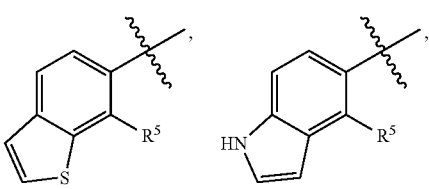
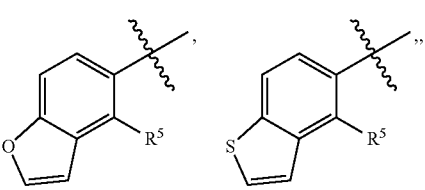
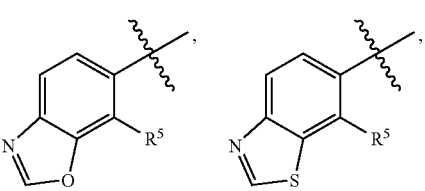
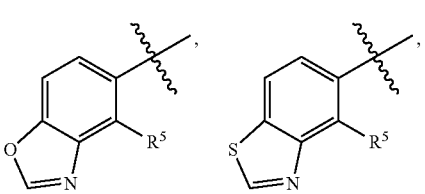

wherein $R^5$ is hydrogen or F.

In some embodiments, $R^2$ is chlorine, methoxy, vinyl, or 1-propenyl; $R^3$ and $R^4$ are hydrogen; X is N, CH, or CF; and A is

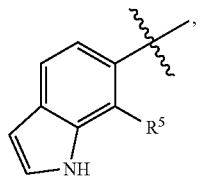

where $R^5$ is hydrogen or F.

In some embodiments, $R^2$ is chlorine, methoxy, vinyl, or 1-propenyl; $R^3$ and $R^4$ are hydrogen; X is N, CH, or CF; and A is

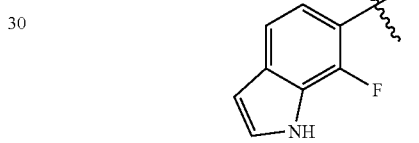

In some embodiments, $R^2$ is chlorine, methoxy, vinyl, or 1-propenyl; $R^3$ and $R^4$ are hydrogen; X is CF; and A is

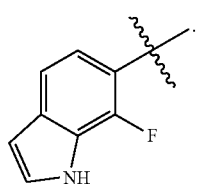 [SMILES: *c1ccc2cc[nH]c2c1F]

In some embodiments, the pyridine carboxylic acid herbicide can comprise a compound defined by Formula (I)

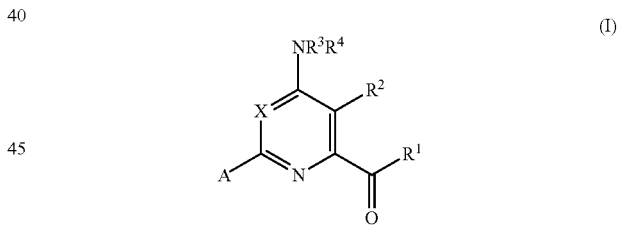

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1''}$ or $NR^{1'''}R^{1''''}$, wherein $R^{1''}$ is hydrogen, $C_1$-$C_8$ alkyl, or $C_7$-$C_{10}$ arylalkyl, and $R^{1'''}$ and $R^{1''''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof, with the proviso that the pyridine carboxylic acid herbicide is not a compound defined by Formula (I)

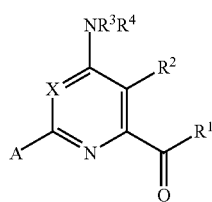

(I)

wherein

X is N, CH, CF, CCl, or CBr;

$R^1$ is $OR^{1'}$, wherein $R^{1'}$ is hydrogen or $C_1$-$C_4$ alkyl;

$R^2$ is chlorine;

$R^3$ and $R^4$ are hydrogen;

A is A1, A2, A3, A4, A5, A6, A7, A8, A9, A10, A1, A12, A13, A14, A15, A16, A17, A18, A19, or A20;

$R^5$ is hydrogen, halogen, OH, amino, CN, $C_1$-$C_3$ alkyl, $C_1$-$C_3$ alkoxy, $C_1$-$C_3$ alkylamino, or cyclopropyl;

$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;

$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and $R^8$ is hydrogen, $C_1$-$C_3$ alkyl, phenyl, or $C_1$-$C_3$ alkylcarbonyl; or an agriculturally acceptable N-oxide or salt thereof.

In some of these embodiments, $R^1$ is $OR^1$. In some of these embodiments, X is CF. In some of these embodiments, A is A15. In some of these embodiments, $R^5$ is F.

In some embodiments:

X is CY, wherein Y is $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1''}$ or $NR^{1''}R^{1'''}$, wherein $R^{1''}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is $C_5$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy. $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is F, Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^1$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently $C_1$-$C_6$ alkyl, $C_1$-$C_6$ haloalkyl, $C_3$-$C_6$ alkenyl, $C_3$-$C_6$ haloalkenyl, $C_3$-$C_6$, alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^{1'}$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio. $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen. $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently $C_1$-$C_4$ alkyl, $C_1$-$C_4$ haloalkyl, halocyclopropyl, $C_3$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino or $C_2$-$C_4$ haloalkylamino, or $NO_2$;

$R^7$ and $R^{7'}$ are independently hydrogen, halogen. $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$10 arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, or A18;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7''}$ are independently $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ haloalkylthio, amino, $C_1$-$C_4$ alkylamino, or $C_2$-$C_4$ haloalkylamino; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$, are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$, cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_3$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen. $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A3, A6, A11, A12, A15, A18, A19, or A20;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is $C_3$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, or $C_1$-$C_6$ trialkylsilyl.

In some of these embodiments, $R^1$ is $OR^1$. In some of these embodiments, X is CF. In some of these embodiments, A is A15. In some of these embodiments, $R^5$ is F.

In certain embodiments, the pyridine carboxylic acid herbicide can comprise a compound defined by Formula (II):

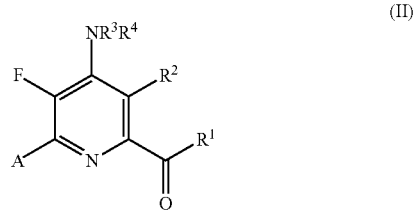

(II)

wherein $R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$ ($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy. $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments:

$R^1$ is $OR^{1'}$, wherein $R^{1'}$ is hydrogen, $C_1$-$C_8$ alkyl, or $C_1$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

A is A1, A2, A3, A7, A8, A9, A10, A11, A12, A13, A14, A15, A21, A22, A23, A24, A27, A28, A29, A30, A31, or A32;

$R^5$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy. $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, $R^1$ is $OR^{1'}$, wherein $R^{1'}$ is hydrogen, $C_1$-$C_8$ alkyl, or $C_7$-$C_{10}$ arylalkyl.

In some embodiments, $R^2$ is halogen, $C_2$-$C_4$-alkenyl, $C_2$-$C_4$ haloalkenyl, or $C_1$-$C_4$-alkoxy. In certain embodiments, $R^2$ is Cl, methoxy, vinyl, or 1-propenyl. In some embodiments, $R^3$ and $R^4$ are hydrogen.

In some embodiments, A is A1, A2, A3, A7, A8, A9, A10, A13, A14, or A15. In certain embodiments, A is A1, A2, A3, A13, A14, or A15. In certain embodiments, A is A15.

In some embodiments, $R^5$ is hydrogen or F. In certain embodiments, $R^5$ is F. In certain embodiments, $R^5$ is H.

In some embodiments, $R^6$ is hydrogen or F. In certain embodiments, $R^6$ is F. In certain embodiments, $R^6$ is H. In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$, $R^{6'}$, and $R^{6''}$ are all hydrogen.

In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

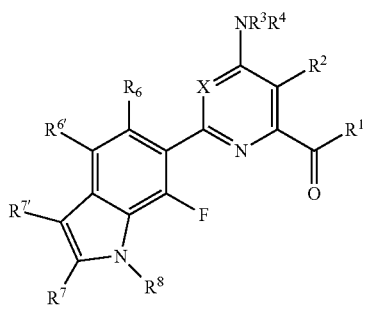

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy. $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$, haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl; or an agriculturally acceptable N-oxide or salt thereof.

In some embodiments:

X is N, CH, CF, CCl, or CBr;

$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl. $C_3$-$C_6$ alkynyl, formyl, $C_1$-$C_3$ alkylcarbonyl, $C_1$-$C_3$ haloalkylcarbonyl, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy. $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, X is N, CH or CF. In some embodiments, X is N. In some embodiments, X is CH. In some embodiments, X is CF. In other embodiments, X is C—$CH_3$.

In some embodiments, $R^2$ is halogen, $C_2$-$C_4$-alkenyl, $C_2$-$C_4$ haloalkenyl, or $C_1$-$C_4$ alkoxy. In certain embodiments, $R^2$ is Cl, methoxy, vinyl, or 1-propenyl. In some embodiments, $R^3$ and $R^4$ are hydrogen.

In some embodiments, $R^6$ is hydrogen or F. In certain embodiments, $R^6$ is F. In certain embodiments, $R^6$ is H. In some embodiments, $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$ and $R^{6'}$ are both hydrogen.

In certain embodiments, $R^7$ and $R^{7'}$ are both hydrogen.

In certain embodiments, $R^6$, $R^{6'}$, $R^7$, and $R^{7'}$ are all hydrogen.

In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise one of Compounds 1-24, the structures of which are shown in the table below.

| Compound No. | Structure |
|---|---|
| 1 | |
| 2 | |
| 3 | |
| 4 | |
| 5 | 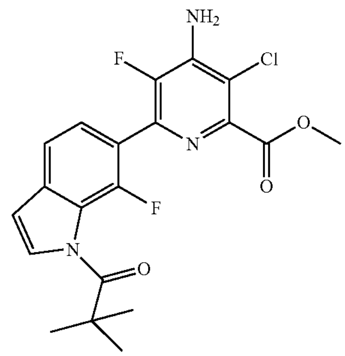 [SMILES: COC(=O)c1nc(-c2ccc3ccn(C(=O)C(C)(C)C)c3c2F)c(F)c(N)c1Cl] |
| 6 | 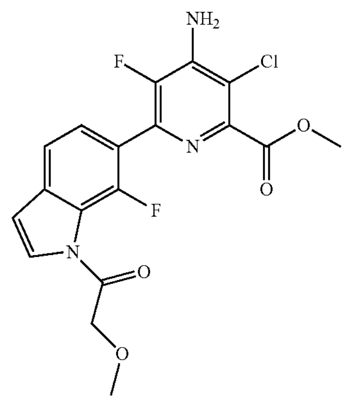 [SMILES: COCC(=O)n1ccc2ccc(-c3nc(C(=O)OC)c(Cl)c(N)c3F)c(F)c21] |
| 7 | 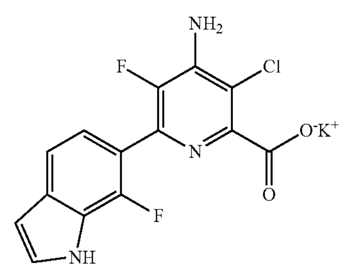 |
| 8 | 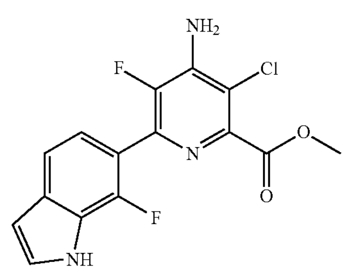 |
| 9 | 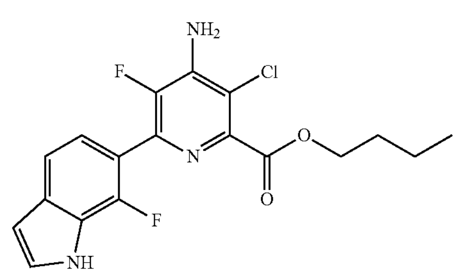 [SMILES: CCCCOC(=O)c1nc(-c2ccc3cc[nH]c3c2F)c(F)c(N)c1Cl] |

-continued
| Compound No. | Structure |
|---|---|
| 10 | 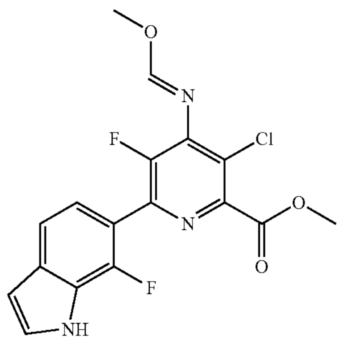 [SMILES: CO/C=N/c1c(F)c(-c2ccc3cc[nH]c3c2F)nc(C(=O)OC)c1Cl] |
| 11 | 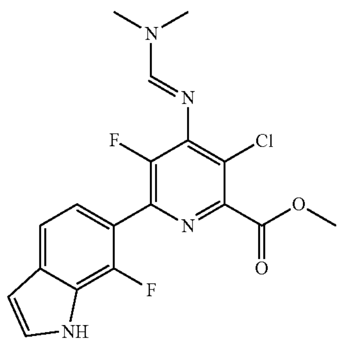 [SMILES: COC(=O)c1nc(-c2ccc3cc[nH]c3c2F)c(F)c(/N=C/N(C)C)c1Cl] |
| 12 | 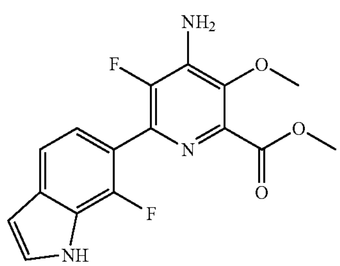 [SMILES: COC(=O)c1nc(-c2ccc3cc[nH]c3c2F)c(F)c(N)c1OC] |
| 13 | 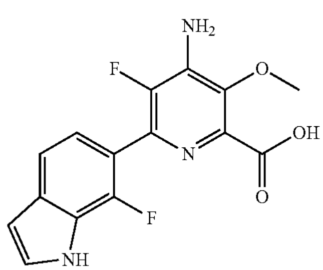 [SMILES: COc1c(C(=O)O)nc(-c2ccc3cc[nH]c3c2F)c(F)c1N] |
| 14 | 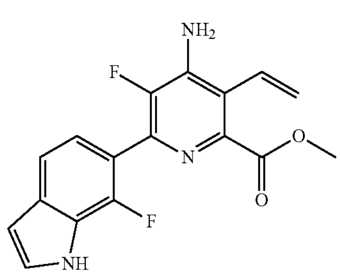 [SMILES: C=Cc1c(C(=O)OC)nc(-c2ccc3cc[nH]c3c2F)c(F)c1N] |
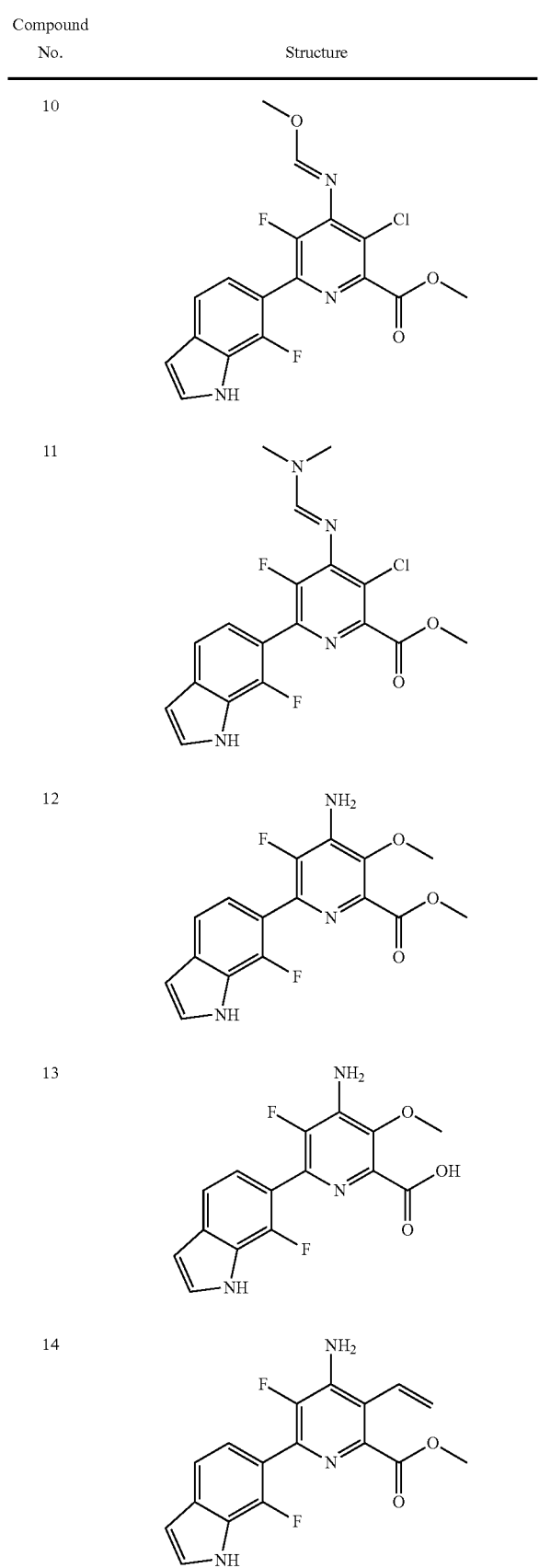
-continued
| Compound No. | Structure |
|---|---|
| 15 | 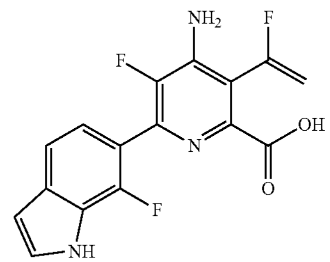 [SMILES: C=C(F)c1c(C(=O)O)nc(-c2ccc3cc[nH]c3c2F)c(F)c1N] |
| 16 | 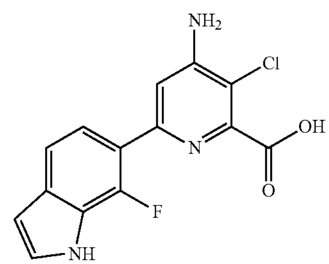 [SMILES: Nc1cc(-c2ccc3cc[nH]c3c2F)nc(C(=O)O)c1Cl] |
| 17 | 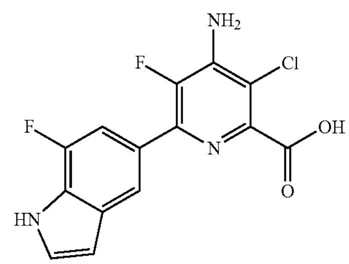 [SMILES: Nc1c(F)c(-c2cc(F)c3[nH]ccc3c2)nc(C(=O)O)c1Cl] |
| 18 | 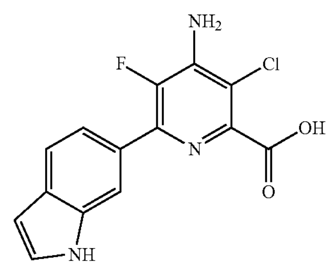 [SMILES: Nc1c(F)c(-c2ccc3cc[nH]c3c2)nc(C(=O)O)c1Cl] |
| 19 | 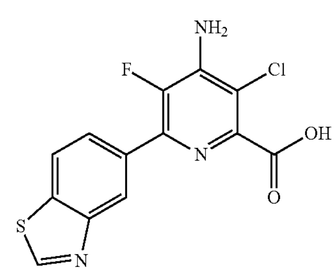 [SMILES: Nc1c(F)c(-c2ccc3scnc3c2)nc(C(=O)O)c1Cl] |
| 20 | 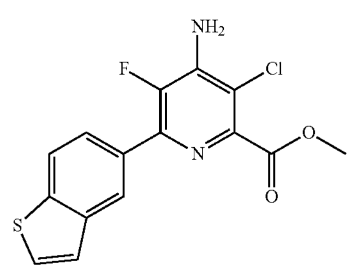 [SMILES: COC(=O)c1nc(-c2ccc3sccc3c2)c(F)c(N)c1Cl] |
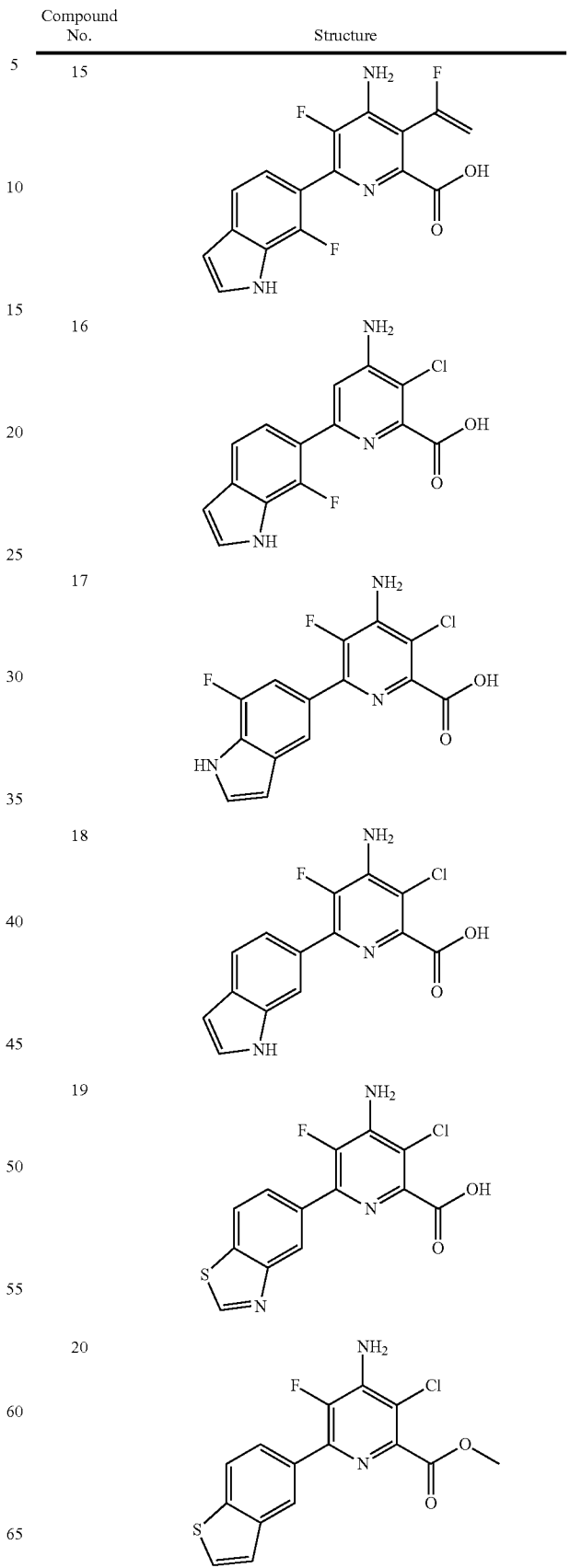

| Compound No. | Structure |
|---|---|
| 21 | (structure: 5-amino-4-methoxy-2-(benzothiophen-6-yl)pyrimidine-carboxylic acid) |
| 22 | (structure: 4-amino-5-fluoro-3-chloro-6-(benzofuran-6-yl)picolinic acid) |
| 23 | (structure: 4-amino-5-fluoro-3-chloro-6-(benzothiazol-6-yl)picolinic acid methyl ester) |
| 24 | (structure: 6-amino-5-methoxy-2-(7-fluorobenzofuran-7-yl)pyrimidine-4-carboxylic acid methyl ester) |

In certain embodiments, the pyridine carboxylic acid herbicide can comprise 4-amino-3-chloro-5-fluoro-6-(7-fluoro-1H-indol-6-yl) picolinic acid or an agriculturally acceptable N-oxide, salt, or ester thereof.

In some embodiments, the pyridine carboxylic acid herbicide can be provided as an agriculturally acceptable salt. Exemplary agriculturally acceptable salts of the pyridine carboxylic acid herbicides of Formula (I) include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, diglycolamine salts, choline salts, and quaternary ammonium salts such as those represented by the formula $R^9R^{10}R^{11}R^{12}N^+$ and wherein $R^9$, $R^{10}$, $R^{11}$ and $R^{12}$ (e.g., $R^9$-$R^{12}$) each independently can represent hydrogen, $C_1$-$C_{10}$ alkyl, $C_2$-$C_8$ alkenyl, $C_2$-$C_8$ alkynyl, $C_1$-$C_8$ alkoxy, $C_1$-$C_8$ alkylthio, or aryl groups, provided that $R^9$-$R^{12}$ are sterically compatible.

In some embodiments, the pyridine carboxylic acid herbicide can be provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl, butoxyethyl esters, substituted or unsubstituted aryl esters, orthoesters, substituted or unsubstituted alkylaryl esters, and substituted or unsubstituted arylalkyl esters. In some embodiments, the ester can comprise a $C_1$-$C_8$ alkyl ester, wherein the $C_1$-$C_8$ alkyl group is optionally substituted with one or more moieties selected from the group consisting of cyano, $C_2$-$C_8$ alkoxy, and $C_2$-$C_8$ alkylsulfonyl. For example, the ester can comprise a methyl, —$CH_2CN$, —$CH_2OCH_3$, —$CH_2OCH_2CH_2OCH_3$, or —$CH_2CH_2SO_2CH_3$ ester.

The ester can also be an acetal (e.g., a cyclic acetal) formed by protection of the carbonyl group in the pyridine carboxylic acid herbicides described above (e.g., by Formula (I)). For example, the pyridine carboxylic acid herbicides described above can be reacted with a suitable diol (e.g., a diol such as ethane-1,2-diol or butane-2,3-diol, for example, using standard protecting group chemistry, such as taught in Greene, et al., *Protective Groups in Organic Synthesis*, John Wiley and Sons, Fourth Edition, 2007, hereby incorporated by reference) to form a cyclic acetal. In one embodiment, the ester can be a cyclic acetal defined by the structure below, where $R^2$, $R^3$, $R^4$, X, and A are as described above.

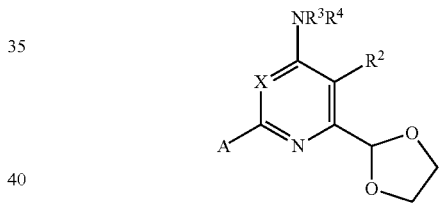

In some embodiments, the ester can comprise a substituted or unsubstituted benzyl ester. In some embodiments, the ester can comprise a benzyl ester optionally substituted with one or more moieties selected from the group consisting of halogen, $C_1$-$C_2$ alkyl, $C_1$-$C_2$ haloalkyl, and combinations thereof. In some embodiments, the ester can comprise a methyl ester.

The pyridine carboxylic acid herbicide or an agriculturally acceptable N-oxide, salt, or ester thereof can be applied to vegetation or an area adjacent the vegetation or applied to soil or water to prevent the emergence or growth of vegetation in an amount sufficient to induce a herbicidal effect. In some embodiments, the pyridine carboxylic acid herbicide or an agriculturally acceptable N-oxide, salt, or ester thereof is applied to vegetation or an area adjacent the vegetation or applied to soil or water to prevent the emergence or growth of vegetation in an amount of 0.1 grams of acid equivalent per hectare (g ae/ha) or greater (e.g., 0.2 g ae/ha or greater, 0.3 g ae/ha or greater, 0.4 g ae/ha or greater, 0.5 g ae/ha or greater, 0.6 g ae/ha or greater, 0.7 g ae/ha or greater, 0.8 g ae/ha or greater, 0.9 g ae/ha or greater, 1 g ae/ha or greater, 1.1 g ae/ha or greater, 1.2 g ae/ha or greater, 1.3 g ae/ha or greater, 1.4 g ae/ha or greater, 1.5 g ae/ha or greater, 1.6 g ae/ha or greater, 1.7 g ae/ha or greater, 1.8 g ae/ha or greater, 1.9 g ae/ha or greater, 2 g ae/ha or greater, 2.25 g ae/ha or greater, 2.5 g ae/ha or greater, 2.75 g ae/ha or greater, 3 g ae/ha or greater, 4 g ae/ha or greater, 5 g ae/ha or greater, 6 g ae/ha or greater, 7 g ae/ha or greater, 8 g ae/ha or greater, 9 g ae/ha or greater, 10 g ae/ha or greater, 11 g ae/ha or greater, 12 g ae/ha or greater, 13 g ae/ha or greater, 14 g ae/ha or greater, 15 g ae/ha or greater, 16 g ae/ha or greater, 17 g ae/ha or greater, 18 g ae/ha or greater, 19 g ae-ha or greater, 20 g ae/ha or greater, 21 g ae/ha or greater, 22 g ae/ha or greater, 23 g ae/ha or greater, 24 g ae/ha or greater, 25 g ae/ha or greater, 26 g ae/ha or greater, 27 g ae/ha or greater, 28 g ae/ha or greater, 29 g ae/ha or greater, 30 g ae/ha or greater, 31 g ae/ha or greater, 32 g ae/ha or greater, 33 g ae/ha or greater, 34 g ae/ha or greater, 35 g ae/ha or greater, 36 g ae/ha or greater, 37 g ae/ha or greater, 38 g ae/ha or greater, 39 g ae/ha or greater, 40 g ae/ha or greater, 41 g ae/ha or greater, 42 g ae/ha or greater, 43 g ae/ha or greater, 44 g ae/ha or greater, 45 g ae/ha or greater, 46 g ae/ha or greater, 47 g ae/ha or greater, 48 g ae/ha or greater, 49 g ae/ha or greater, 50 g ae/ha or greater, 55 g ae/ha or greater, 60 g ae/ha or greater, 65 g ae/ha or greater, 70 g ae/ha or greater, 75 g ae/ha or greater, 80 g ae/ha or greater, 85 g ae/ha or greater, 90 g ae/ha or greater, 95 g ae/ha or greater, 100 g ae/ha or greater, 110 g ae/ha or greater, 120 g ae/ha or greater, 130 g ae-ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, or 290 g ae/ha or greater).

In some embodiments, the pyridine carboxylic acid herbicide or an agriculturally acceptable N-oxide, salt, or ester thereof is applied to vegetation or an area adjacent the vegetation or applied to soil or water to prevent the emergence or growth of vegetation in an amount of 300 g ae/ha or less (e.g., 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 49 g ae/ha or less, 48 g ae/ha or less, 47 g ae/ha or less, 46 g ae/ha or less, 45 g ae/ha or less, 44 g ae/ha or less, 43 g ae/ha or less, 42 g ae/ha or less, 41 g ae/ha or less, 40 g ae/ha or less, 39 g ae/ha or less, 38 g ae/ha or less, 37 g ae/ha or less, 36 g ae/ha or less, 35 g ae/ha or less, 34 g ae/ha or less, 33 g ae/ha or less, 32 g ae/ha or less, 31 g ae/ha or less, 30 g ae/ha or less, 29 g ae/ha or less, 28 g ae/ha or less, 27 g ae/ha or less, 26 g ae/ha or less, 25 g ae/ha or less, 24 g ae/ha or less, 23 g ae/ha or less, 22 g ae/ha or less, 21 g ae/ha or less, 20 g ae/ha or less, 19 g ae/ha or less, 18 g ae/ha or less, 17 g ae/ha or less, 16 g ae/ha or less, 15 g ae/ha or less, 14 g ae/ha or less, 13 g ae/ha or less, 12 g ae/ha or less, 11 g ae/ha or less, 10 g ae/ha or less, 9 g ae/ha or less, 8 g ae/ha or less, 7 g ae/ha or less, 6 g ae/ha or less, 5 g ae/ha or less, 4 g ae/ha or less, 3 g ae/ha or less, 2.75 g ae/ha or less, 2.5 g ae/ha or less, 2.25 g ae/ha or less, 2 g ae/ha or less, 1.9 g ae/ha or less, 1.8 g ae/ha or less, 1.7 g ae/ha or less, 1.6 g ae/ha or less, 1.5 g ae/ha or less, 1.4 g ae/ha or less, 1.3 g ae/ha or less, 1.2 g ae/ha or less, 1.1 g ae/ha or less, 1 g ae/ha or less, 0.9 g ae/ha or less, 0.8 g ae/ha or less, 0.7 g ae/ha or less, 0.6 g ae/ha or less, 0.5 g ae/ha or less, 0.4 g ae/ha or less, 0.3 g ae/ha or less, or 0.2 g ae/ha or less).

The pyridine carboxylic acid herbicide or an agriculturally acceptable N-oxide, salt, or ester thereof can be applied to vegetation or an area adjacent the vegetation or applied to soil or water to prevent the emergence or growth of vegetation in an amount ranging from any of the minimum values described above to any of the maximum values described above. In some embodiments, the pyridine carboxylic acid herbicide or an agriculturally acceptable N-oxide, salt, or ester thereof is applied to vegetation or an area adjacent the vegetation or applied to soil or water to prevent the emergence or growth of vegetation in an amount of from 0.1-300 g ae/ha (e.g., from 0.5-300 g ae/ha, from 0.1-5 g ae/ha, from 0.5-5 g ae/ha, from 2.5-40 g ae/ha, from 0.1-40 g ae/ha, from 0.5-40 g ae/ha, from 0.1-2.5 g ae/ha, from 0.5-2.5 g ae/ha, from 2-150 g ae/ha, from 5-75 g ae/ha, from 5-40 g ae/ha, from 30-40 g ae/ha, or from 5-15 g ae/ha). In some embodiments, the pyridine carboxylic acid herbicide or an agriculturally acceptable N-oxide, salt, or ester thereof is applied in an amount from 5-40 g ae/ha. In some embodiments, the pyridine carboxylic acid herbicide or an agriculturally acceptable N-oxide, salt, or ester thereof is applied in an amount from 30-40 g ae/ha. In some embodiments, the pyridine carboxylic acid herbicide or an agriculturally acceptable N-oxide, salt, or ester thereof is applied in an amount from 5-15 g ae/ha.

ALS Inhibitors

In addition to the pyridine carboxylic acid herbicide or agriculturally acceptable N-oxide, salt or ester thereof, the compositions can include an acetolactate synthase (ALS) inhibitor. ALS inhibitors disrupt the production of amino acids in the plant, which eventually leads to inhibition of DNA synthesis. Examples of ALS inhibitors include sulfonylureas, imidazolinones, triazolopyrimidine sulfonamides, pyrimidinyl oxybenzoates and sulfonylaminocarbonyl triazolinones. In some embodiments, the ALS inhibitor can comprise a triazolopyrimidine sulfonamide herbicide. In some embodiments, the ALS inhibitor can comprise an imidazolinone herbicide. In some embodiments, the ALS inhibitor can comprise a pyrimidinyl oxybenzoate herbicide. In some embodiments, the ALS inhibitor can comprise a sulfonylaminocarbonyl triazolinone herbicide. In some embodiments, the ALS inhibitor can comprise a sulfonylurea herbicide.

In some embodiments, the composition can include an ALS inhibitor selected from the group consisting of imidazolinones, triazolopyrimidine sulfonamides, pyrimidinyl oxybenzoates, sulfonylaminocarbonyl triazolinones, sulfonylureas, and combinations thereof. In some cases, the composition can include penoxsulam, amidosulfuron, azimsulfuron, bispyribac, bensulfuron, chlorimuron, clorsulfuron, cinosulfuron, cloransulam, cyclosulfamuron, diclosulam, ethametsulfuron, ethoxysulfuron, flazasulfuron, florasulam, flucarbazone, flucetosulfuron, flumetsulam, flupyrsulfuron, foramsulfuron, halosulfuron, imazamethabenz, imazamox, imazapic, imazapyr, imazaquin, imazethapyr, imazosulfuron, iodosulfuron, iofensulfuron, mesosulfuron, metazosulfuron, metosulam, metsulfuron, nicosulfuron, orthosulfamuron, oxasulfuron, primisulfuron, propoxycarbazone, propyrisulfuron, prosulfuron, pyrazosulfuron, pyribenzoxim, pyriftalid, pyriminobac, pyrimisulfan, pyrithiobac, pyroxasulfone, pyroxsulam, rimsulfuron, sulfometuron, sulfosulfuron, thiencarbazone, thifensulfuron, thiencarbazone, triasulfuron, tribenuron, thifensulfuron, trifloxysulfuron, tritosulfuron, agriculturally acceptable salts and esters thereof, and combinations thereof.

The ALS inhibitor or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the ALS inhibitor or agriculturally acceptable salt or ester thereof is applied to vegetation or an area adjacent the vegetation or applied to soil or water to prevent the emergence or growth of vegetation in an amount of 0.25 grams active ingredient per hectare (g ai/ha) or more (e.g., 0.3 g ai/ha or more, 0.4 g ai/ha or more, 0.5 g ai/ha or more, 0.6 g ai/ha or more, 0.7 g ai/ha or more, 0.8 g ai/ha or more, 0.9 g ai/ha or more, 1 g ai/ha or more, 1.5 g ai/ha or more, 2 g ai/ha or more, 2.5 g ai/ha or more, 3 g ai/ha or more, 3.5 g ai/ha or more, 4 g ai/ha or more, 4.5 g ai/ha or more, 5 g ai/ha or more, 6 g ai/ha or more, 7 g ai/ha or more, 8 g ai/ha or more, 9 g ai/ha or more, 10 g ai/ha or more, 15 g ai/ha or more, 20 g ai/ha or more, 25 g ai/ha or more, 30 g ai/ha or more, 35 g ai/ha or more, 40 g ai/ha or more, 45 g ai/ha or more, 50 g ai/ha or more, 55 g ai/ha or more, 60 g ai/ha or more, 65 g ai/ha or more, 70 g ai/ha or more, 75 g ai/ha or more, 80 g ai/ha or more, 85 g ai/ha or more, 90 g ai/ha or more, 95 g ai/ha or more, 100 g ai/ha or more, 110 g ai/ha or more, 120 g ai/ha or more, 130 g ai/ha or more, 140 g ai/ha or more, 150 g ai/ha or more, 160 g ai/ha or more, 170 g ai/ha or more, 180 g ai/ha or more, 190 g ai/ha or more, 200 g ai/ha or more, 210 g a/ha or more, 220 g a/ha or more, 230 g a/ha or more, 240 g ai/ha or more, 250 g ai/ha or more, 260 g ai/ha or more, 270 g ai/ha or more, 280 g ai/ha or more, 290 g ai/ha or more, 300 g ai/ha or more, 310 g ai/ha or more, 320 g ai/ha or more, 330 g ai/ha or more, 340 g ai/ha or more, 350 g ai/ha or more, 360 g ai/ha or more, 370 g ai/ha or more, 380 g ai/ha or more, 390 g ai/ha or more, 400 g ai/ha or more, 420 g ai/ha or more, 440 g ai/ha or more, 460 g ai/ha or more, 480 g ai/ha or more, 500 g ai/ha or more, 520 g ai/ha or more, 540 g ai/ha or more, 560 g ai/ha or more, 580 g ai/ha or more, 600 g ai/ha or more, 625 g ai/ha or more, 650 g ai/ha or more, 675 g ai/ha or more, 700 g ai/ha or more, 725 g ai/ha or more, 750 g ai/ha or more, 775 g ai/ha or more, 800 g ai/ha or more, 825 g ai/ha or more, 850 g ai/ha or more, 875 g ai/ha or more, 900 g ai/ha or more, 925 g ai/ha or more, 950 g ai/ha or more, 975 g ai/ha or more, 1000 g ai/ha or more, 1050 g ai/ha or more, 1100 g ai/ha or more, 1150 g ai/ha or more, 1200 g ai/ha or more, 1250 g ai/ha or more, 1300 g ai/ha or more, 1350 g ai/ha or more, 1400 g ai/ha or more, 1450 g ai/ha or more, 1500 g ai/ha or more, 1550 g ai/ha or more, 1600 g ai/ha or more, 1650 g ai/ha or more, 1660 g ai/ha or more, 1670 g ai/ha or more, 1680 g ai/ha or more, or 1690 g ai/ha or more).

In some embodiments, the ALS inhibitor or agriculturally acceptable salt or ester thereof is applied to vegetation or an area adjacent the vegetation or applied to soil or water to prevent the emergence or growth of vegetation in an amount of 1700 g ai/ha or less (e.g., 1690 g ai/ha or less, 1680 g ai/ha or less, 1670 g ai/ha or less, 1660 g ai/ha or less, 1650 g ai/ha or less, 1600 g ai/ha or less, 1550 g ai/ha or less, 1500 g ai/ha or less, 1450 g ai/ha or less, 1400 g ai/ha or less, 1350 g ai/ha or less, 1300 g ai/ha or less, 1250 g ai/ha or less, 1200 g ai/ha or less, 1150 g ai/ha or less, 1100 g ai/ha or less, 1050 g ai/ha or less, 1000 g ai/ha or less, 975 g ai/ha or less, 950 g ai/ha or less, 925 g ai/ha or less, 900 g ai/ha or less, 875 g ai/ha or less, 850 g ai/ha or less, 825 g ai/ha or less, 800 g ai/ha or less, 775 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 580 g ai/ha or less, 560 g ai/ha or less, 540 g ai/ha or less, 520 g ai/ha or less, 500 g ai/ha or less, 480 g ai/ha or less, 460 g ai/ha or less, 440 g ai/ha or less, 420 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai/ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, 35 g ai/ha or less, 30 g ai/ha or less, 25 g ai/ha or less, 20 g ai/ha or less, 15 g ai/ha or less, 10 g ai/ha or less, 9 g ai/ha or less, 8 g ai/ha or less, 7 g ai/ha or less, 6 g ai/ha or less, 5 g ai/ha or less, 4.5 g ai/ha or less, 4 g ai/ha or less, 3.5 g ai/ha or less, 3 g ai/ha or less, 2.5 g ai/ha or less, 2 g ai/ha or less, 1.5 g ai/ha or less, 1 g ai/ha or less, 0.9 g ai/ha or less, 0.8 g ai/ha or less, 0.7 g ai/ha or less, 0.6 g ai/ha or less, 0.5 g ai/ha or less, 0.4 g ai/ha or less, or 0.3 g ai/ha or less).

The ALS inhibitor or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the ALS inhibitor or agriculturally acceptable salt or ester thereof is applied to vegetation or an area adjacent the vegetation or applied to soil or water to prevent the emergence or growth of vegetation in an amount of 0.25-1700 g ai/ha (e.g., 0.25-1250 g ai/ha, 1250-1700 g ai/ha, 0.25-1200 g ai/ha, 0.25-1150 g ai/ha, 0.25-1100 g ai/ha, 0.25-1060 g ai/ha, 0.25-1000 g ai/ha, 0.25-900 g ai/ha, 0.25-800 g ai/ha, 0.25-750 g ai/ha, 750-1000 g ai/ha, 0.25-700 g ai/ha, 0.25-650 g ai/ha, 0.25-600 g ai/ha, 0.25-560 g ai/ha, 0.25-500 g ai/ha, 0.25-460 g ai/ha, 0.25-400 g ai/ha, 0.25-460 g ai/ha, 0.25-400 g ai/ha, 0.25-360 g ai/ha, 0.25-300 g ai/ha, 0.25-280 g ai/ha, 5-260 g ai/ha, 0.25-240 g ai/ha, 0.25-220 g ai/ha, 0.25-200 g ai/ha, 0.25-180 g ai/ha, 0.25-160 g ai/ha, 0.25-140 g ai/ha, 0.25-120 g ai/ha, 0.25-100 g ai/ha, 0.25-90 g ai/ha, 0.25-80 g ai/ha, 0.25-70 g ai/ha, 0.25-60 g ai/ha, 0.25-50 g ai/ha, 0.25-40 g ai/ha, 0.25-30 g ai/ha, 0.25-20 g ai/ha, 0.25-10 g ai/ha, 10-560 g ai/ha, 20-500 g ai/ha, 30-460 g ai/ha, 40-400 g ai/ha, 50-360 g ai/ha, 60-300 g ai/ha, 70-280 g ai/ha, 70-100 g ai/ha, 70-140 g ai/ha, 100-140 g ai/ha, 100-280 g ai/ha, or 140-280 g ai/ha).

In certain embodiments, the herbicidal composition comprises a herbicidally effective amount of (a) a pyridine carboxylic acid herbicide or an agriculturally acceptable N-oxide, salt, or ester thereof, and (b) florasulam, cloransulam, diclosulam, flumetsulam, metosulam, penoxsulam, pyroxsulam, agriculturally acceptable salts or esters thereof, or combinations thereof.

Florasulam

Compositions and methods of the present disclosure can include florasulam or an agriculturally acceptable salt thereof. Florasulam, shown below, is a triazolopyrimidine sulfonamide that provides broad-spectrum control of many broad-leaved weeds in cereals and maize. Florasulam, as well as methods of preparing florasulam, are known in the art. Its herbicidal activity is described, for example, in *The Pesticide Manual*, Fifteenth Edition, 2009.

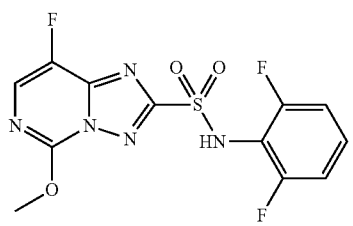 [SMILES: COc1ncc(F)c2nc(S(=O)(=O)Nc3c(F)cccc3F)nn12]

In some embodiments, florasulam can be provided as an agriculturally acceptable salt of florasulam.

The florasulam or agriculturally acceptable salt thereof can be applied to vegetation or an area adjacent the vegetation or applied to soil or water to prevent the emergence or growth of vegetation in an amount sufficient to induce a herbicidal effect. In some embodiments, the florasulam or agriculturally acceptable salt thereof is applied to vegetation or an area adjacent the vegetation or applied to soil or water to prevent the emergence or growth of vegetation in an amount of 0.25 g ai/ha or more (e.g., 0.3 g ai/ha or more, 0.4 g ai/ha or more, 0.5 g ai/ha or more, 0.6 g ai/ha or more, 0.7 g ai/ha or more, 0.8 g ai/ha or more, 0.9 g ai/ha or more, 1 g ai/ha or more, 1.1 g ai/ha or more, 1.25 g ai/ha or more, 1.5 g ai/ha or more, 1.75 g ai/ha or more, 2 g ai/ha or more, 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 5.25 g ai/ha or more, 5.5 g ai/ha or more, 5.75 g ai/ha or more, 6 g ai/ha or more, 6.25 g ai/ha or more, 6.5 g ai/ha or more, 6.75 g ai/ha or more, 7 g ai/ha or more, or 7.25 g ai/ha or more).

In some embodiments, the florasulam or agriculturally acceptable salt thereof is applied to vegetation or an area adjacent the vegetation or applied to soil or water to prevent the emergence or growth of vegetation in an amount of 7.5 g ai/ha or less (e.g., 7.25 g ai/ha or less, 7 g ai/ha or less, 6.75 g ai/ha or less, 6.5 g ai/ha or less, 6.25 g ai/ha or less, 6 g ai/ha or less, 5.75 g ai/ha or less, 5.5 g ai/ha or less, 5.25 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, 2.75 g ai/ha or less, 2.5 g ai/ha or less, 2.25 g ai/ha or less, 2 g ai/ha or less, 1.75 g ai/ha or less, 1.5 g ai/ha or less, 1.25 g ai/ha or less, 1 g ai/ha or less, 0.9 g ai/ha or less, 0.8 g ai/ha or less, 0.7 g ai/ha or less, 0.6 g ai/ha or less, 0.5 g ai/ha or less, 0.4 g ai/ha or less, or 0.3 g ai/ha or less).

The florasulam or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the florasulam or agriculturally acceptable salt thereof is applied to vegetation or an area adjacent the vegetation or applied to soil or water to prevent the emergence or growth of vegetation in an amount of 0.25-7.5 g ai/ha (e.g., 0.25-7 g ai/ha, 0.25-6.5 g ai/ha, 0.25-6 g ai/ha, 0.25-5.5 g ai/ha, 0.25-5 g ai/ha, 0.25-4.5 g ai/ha, 0.25-4 g ai/ha, 0.25-3.5 g ai/ha, 0.25-3 g ai/ha, 0.25-2.5 g ai/ha, 0.5-2 g ai/ha, 0.75-1.75 g ai/ha, or 1-1.5 g ai/ha).

Cloransulam

Compositions and methods of the present disclosure can include cloransulam or an agriculturally acceptable salt thereof. Cloransulam, as well as methods of preparing cloransulam, are known in the art. In some embodiments, cloransulam can be provided as an agriculturally acceptable ester of cloransulam. Cloransulam-methyl, shown below, is a triazolopyrimidine sulfonamide that provides broad-spectrum control of many broadleaf weeds in soybeans and other broadleaf crops. Its herbicidal activity is described in *The Pesticide Manual*, Fifteenth Edition, 2009.

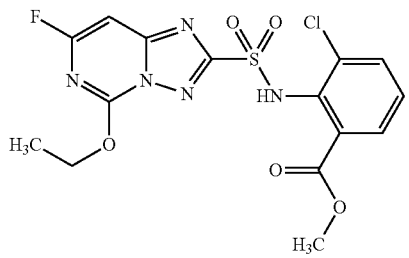 [SMILES: CCOc1nc(F)cc2nc(S(=O)(=O)Nc3c(Cl)cccc3C(=O)OC)nn12]

The cloransulam or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the cloransulam or agriculturally acceptable salt or ester thereof is applied to vegetation or an area adjacent the vegetation or applied to soil or water to prevent the emergence or growth of vegetation in an amount of 2.18 g ai/ha or more (e.g., 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or less, 4.5 g ai/ha or more, 5 g ai/ha or more, 6 g ai/ha or more, 7 g ai/ha or more, 8 g ai/ha or more, 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, or 60 g ai/ha or more).

In some embodiments, the cloransulam or agriculturally acceptable salt thereof is applied to vegetation or an area adjacent the vegetation or applied to soil or water to prevent the emergence or growth of vegetation in an amount of 61 g ai/ha or less (e.g., 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, 6 g ai/ha or less, 5 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, 2.75 g ai/ha or less, 2.5 g ai/ha or less, or 2.25 g ai/ha or less).

The cloransulam or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the cloransulam or agriculturally acceptable salt thereof is applied to vegetation or an area adjacent the vegetation or applied to soil or water to prevent the emergence or growth of vegetation in an amount of 2.18-61 g ai/ha (e.g., 2.5-60 g ai/ha, 2.75-55 g ai/ha, 3-50 g ai/ha, 3.25-60 g ai/ha, 3.5-50 g ai/ha, 3.75-60 g ai/ha, 3.75-50 g ai/ha, 4-60 g ai/ha, 4-50 g ai/ha, 4.25-60 g ai/ha, 4.25-55 g ai/ha, 4.25-50 g ai/ha, or 4.25-45 g ai/ha).

Diclosulam

Compositions and methods of the present disclosure can include diclosulam or an agriculturally acceptable salt thereof. Diclosulam, shown below, is a triazolopyrimidine sulfonamide that provides broad-spectrum control of many broadleaf weeds in soybeans and peanuts. Diclosulam, as well as methods of preparing diclosulam, are known in the art. Its herbicidal activity is described in *The Pesticide Manual*, Fifteenth Edition, 2009.

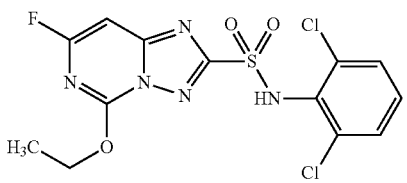 [SMILES: CCOc1nc(F)cc2nc(S(=O)(=O)Nc3c(Cl)cccc3Cl)nn12]

In some embodiments, diclosulam can be provided as an agriculturally acceptable salt of diclosulam.

The diclosulam or agriculturally acceptable salt thereof can be applied to vegetation or an area adjacent the vegetation or applied to soil or water to prevent the emergence or growth of vegetation in an amount sufficient to induce a herbicidal effect. In some embodiments, the diclosulam or agriculturally acceptable salt thereof is applied to vegetation or an area adjacent the vegetation or applied to soil or water to prevent the emergence or growth of vegetation in an amount of 2.18 g ai/ha or more (e.g., 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 10.5 g ai/ha or more, 11 g ai/ha or more, 11.5 g ai/ha or more, 12 g ai/ha or more, 12.5 g ai/ha or more, 13 g ai/ha or more, 13.5 g ai/ha or more, 14 g ai/ha or more, 14.5 g ai/ha or more, 15 g ai/ha or more, 15.5 g ai/ha or more, 16 g ai/ha or more, 16.5 g ai/ha or more, 17 g ai/ha or more, 17.5 g ai/ha or more, 18 g ai/ha or more, 18.5 g ai/ha or more, 19 g ai/ha or more, 19.5 g ai/ha or more, 20 g a/ha or more, 20.5 g ai/ha or more, 21 g ai/ha or more, 21.5 g a/ha or more, 22 g ai/ha or more, 22.5 g ai/ha or more, 23 g ai/ha or more, 23.5 g ai/ha or more, 24 g ai/ha or more, 24.5 g ai/ha or more, 25 g ai/ha or more, 25.5 g ai/ha or more, 26 g ai/ha or more, 26.5 g ai/ha or more, 27 g ai/ha or more, 27.5 g ai/ha or more, 28 g ai/ha or more, 28.5 g ai/ha or more, 29 g ai/ha or more, 29.5 g ai/ha or more, 30 g ai/ha or more, 30.5 g ai/ha or more, 31 g ai/ha or more, 31.5 g ai/ha or more, 32 g ai/ha or more, 32.5 g ai/ha or more, 33 g ai/ha or more, 33.5 g ai/ha or more, 34 g ai/ha or more, 34.5 g ai/ha or more, or 34.75 g ai/ha or more).

In some embodiments, the diclosulam or agriculturally acceptable salt thereof is applied to vegetation or an area adjacent the vegetation or applied to soil or water to prevent the emergence or growth of vegetation in an amount of 35 g ai/ha or less (e.g., 34.5 g ai/ha or less, 34 g ai/ha or less, 33.5 g ai/ha or less, 33 g ai/ha or less, 32.5 g ai/ha or less, 32 g ai/ha or less, 31.5 g ai/ha or less, 31 g ai/ha or less, 30.5 g ai/ha or less, 30 g ai/ha or less, 29.5 g ai/ha or less, 29 g ai/ha or less, 28.5 g ai/ha or less, 28 g ai/ha or less, 27.5 g ai/ha or less, 27 g ai/ha or less, 26.5 g ai/ha or less, 26 g ai/ha or less, 25.5 g ai/ha or less, 25 g ai/ha or less, 24.5 g ai/ha or less, 24 g ai/ha or less, 23.5 g ai/ha or less, 23 g ai/ha or less, 22.5 g ai/ha or less, 22 g ai/ha or less, 21.5 g ai/ha or less, 21 g ai/ha or less, 20.5 g ai/ha or less, 20 g ai/ha or less, 19.5 g ai/ha or less, 19 g ai/ha or less, 18.5 g ai/ha or less, 18 g ai/ha or less, 17.5 g ai/ha or less, 17 g ai/ha or less, 16.5 g ai/ha or less, 16 g ai/ha or less, 15.5 g ai/ha or less, 15 g ai/ha or less, 14.5 g ai/ha or less, 14 g ai/ha or less, 13.5 g ai/ha or less, 13 g ai/ha or less, 12.5 g ai/ha or less, 12 g ai/ha or less, 11.5 g ai/ha or less, 11 g ai/ha or less, 10.5 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 2.75 g ai/ha or less, 2.5 g ai/ha or less, or 2.25 g ai/ha or less).

The diclosulam or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the diclosulam or agriculturally acceptable salt thereof is applied to vegetation or an area adjacent the vegetation or applied to soil or water to prevent the emergence or growth of vegetation in an amount of 2.18-35 g ai/ha (e.g., 2.5-34 g ai/ha, 2.75-32 g ai/ha, 3-30 g ai/ha, 3.25-35 g ai/ha, 3.25-32 g ai/ha, 3.5-30 g ai/ha, 3.75-34 g ai/ha, 4-35 g ai/ha, 4-30 g ai/ha, 4.25-35 g ai/ha, 4.25-34 g ai/ha, 4.25-32 g ai/ha, or 4.25-30 g ai/ha).

Flumetsulam

Compositions and methods of the present disclosure can include flumetsulam or an agriculturally acceptable salt thereof. Flumetsulam, shown below, is a triazolopyrimidine sulfonamide that provides control of broadleaf weeds and greens in soybeans, field peas, and maize. Flumetsulam, as well as methods of preparing flumetsulam, are known in the art. Its herbicidal activity is described in *The Pesticide Manual*, Fifteenth Edition, 2009.

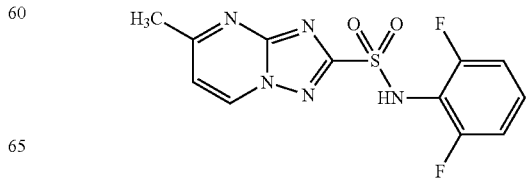

In some embodiments, flumetsulam can be provided as an agriculturally acceptable salt of flumetsulam.

The flumetsulam or agriculturally acceptable salt thereof can be applied to vegetation or an area adjacent the vegetation or applied to soil or water to prevent the emergence or growth of vegetation in an amount sufficient to induce a herbicidal effect. In some embodiments, the flumetsulam or agriculturally acceptable salt thereof is applied to vegetation or an area adjacent the vegetation or applied to soil or water to prevent the emergence or growth of vegetation in an amount of 2.18 g ai/ha or more (e.g., 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 6 g ai/ha or more, 7 g ai/ha or more, 8 g ai/ha or more, 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai/ha or more, 69 g ai/ha or more, 70 g ai/ha or more, 71 g ai/ha or more, 72 g ai/ha or more, 73 g ai/ha or more, 74 g ai/ha or more, 75 g ai/ha or more, 76 g ai/ha or more, or 77 g ai/ha or more).

In some embodiments, the flumetsulam or agriculturally acceptable salt thereof is applied to vegetation or an area adjacent the vegetation or applied to soil or water to prevent the emergence or growth of vegetation in an amount of 78 g ai/ha or less (e.g., 77 g ai/ha or less, 76 g ai/ha or less, 75 g ai/ha or less, 74 g ai/ha or less, 73 g ai/ha or less, 72 g ai/ha or less, 71 g ai/ha or less, 70 g ai/ha or less, 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai ha or less, 7 g ai/ha or less, 6 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, 2.75 g ai/ha or less, 2.5 g ai/ha or less, or 2.25 g ai/ha or less).

The flumetsulam or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the flumetsulam or agriculturally acceptable salt thereof is applied to vegetation or an area adjacent the vegetation or applied to soil or water to prevent the emergence or growth of vegetation in an amount of 2.18-78 g ai/ha (e.g., 2.5-75 g ai/ha, 2.75-70 g ai/ha, 3-65 g ai/ha, 3.25-78 g ai/ha, 3.5-75 g ai/ha, 3.75-70 g ai/ha, 4-78 g ai/ha, 4-75 g ai/ha, 4-70 g ai/ha, 4.25-78 g ai/ha, 4.25-75 g ai/ha, 4.25-70 g ai ha, or 4.25-65 g ai/ha).

Penoxsulam

Compositions and methods of the present disclosure can include penoxsulam or an agriculturally acceptable salt thereof. Penoxsulam, shown below, is a triazolopyrimidine sulfonamide that provides control of *Echinochloa* spp., as well as many broadleaf, sedge, and aquatic weeds in rice. Penoxsulam, as well as methods of preparing penoxsulam, are known in the art. Its herbicidal activity is described in *The Pesticide Manual*, Fifteenth Edition, 2009.

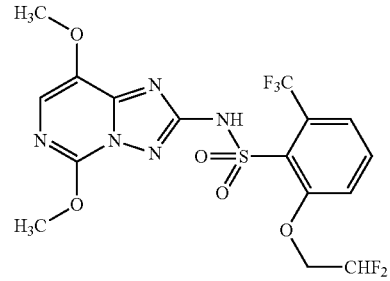 [SMILES: COc1cnc(OC)n2nc(NS(=O)(=O)c3c(OCC(F)F)cccc3C(F)(F)F)nc12]

In some embodiments, penoxsulam can be provided as an agriculturally acceptable salt of penoxsulam.

The penoxsulam or agriculturally acceptable salt thereof can be applied to vegetation or an area adjacent the vegetation or applied to soil or water to prevent the emergence or growth of vegetation in an amount sufficient to induce a herbicidal effect. In some embodiments, the penoxsulam or agriculturally acceptable salt thereof is applied to vegetation or an area adjacent the vegetation or applied to soil or water to prevent the emergence or growth of vegetation in an amount of 2.5 grams active ingredient per hectare (g ai/ha) or more (e.g., 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 6 g ai/ha or more, 7 g ai % ha or more, 8 g ai/ha or more, 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, or 49 g ai/ha or more).

In some embodiments, the penoxsulam or agriculturally acceptable salt thereof is applied to vegetation or an area adjacent the vegetation or applied to soil or water to prevent the emergence or growth of vegetation in an amount of 50 g ai/ha or less (e.g., 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, 6 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, or 2.75 g ai/ha or less).

The penoxsulam or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the penoxsulam or agriculturally acceptable salt thereof is applied to vegetation or an area adjacent the vegetation or applied to soil or water to prevent the emergence or growth of vegetation in an amount of 2.5-50 g ai/ha (e.g., 3-48 g ai/ha, 3.25-46 g ai/ha, 3.5-40 g ai/ha, 3.5-50 g ai/ha, 3.75-45 g ai/ha, 3.75-40 g ai/ha, 4-50 g ai/ha, 4-45 g ai/ha, 4-40 g ai/ha, 4.25-50 g ai/ha, 4.25-48 g ai/ha, 4.25-46 g ai/ha, or 4.25-45 g ai/ha).

Pyroxsulam

Compositions and methods of the present disclosure can include pyroxsulam or an agriculturally acceptable salt thereof. Pyroxsulam, shown below, is a triazolopyrimidine sulfonamide that provides broad spectrum post-emergence annual grass and broadleaf weeds control in cereals. Pyroxsulam, as well as methods of preparing pyroxsulam, are known in the art. Its herbicidal activity is described in *The Pesticide Manual*, Fifteenth Edition, 2009.

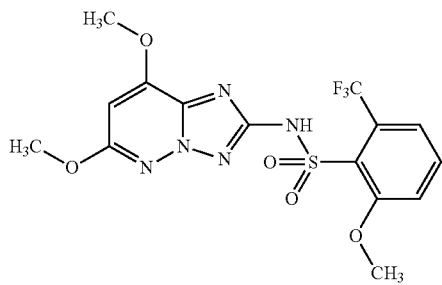 [SMILES: COc1cc(OC)c2nc(NS(=O)(=O)c3c(OC)cccc3C(F)(F)F)nn2n1]

In some embodiments, pyroxsulam can be provided as an agriculturally acceptable salt of pyroxsulam.

The pyroxsulam or agriculturally acceptable salt thereof can be applied to vegetation or an area adjacent the vegetation or applied to soil or water to prevent the emergence or growth of vegetation in an amount sufficient to induce a herbicidal effect. In some embodiments, the pyroxsulam or agriculturally acceptable salt thereof is applied to vegetation or an area adjacent the vegetation or applied to soil or water to prevent the emergence or growth of vegetation in an amount of 1.9 g ai/ha or more (e.g., 2 g ai/ha or more, 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 5.25 g ai/ha or more, 5.5 g ai/ha or more, 5.75 g ai/ha or more, 6 g ai/ha or more, 6.25 g ai/ha or more, 6.5 g ai/ha or more, 6.75 g ai/ha or more, 7 g ai/ha or more, 7.25 g ai/ha or more, 7.5 g ai/ha or more, 7.75 g ai/ha or more, 8 g ai/ha or more, 8.25 g ai/ha or more, 8.5 g ai/ha or more, 8.75 g ai/ha or more, 9 g ai/ha or more, 9.25 g ai/ha or more, 9.5 g ai/ha or more, 9.75 g ai/ha or more, 10 g ai/ha or more, 10.25 g ai/ha or more, 10.5 g ai/ha or more, 10.75 g ai/ha or more, 11 g ai/ha or more, 11.25 g ai/ha or more, 11.5 g ai/ha or more, 11.75 g ai/ha or more, 12 g ai/ha or more, 12.25 g ai/ha or more, 12.5 g ai/ha or more, 12.75 g ai/ha or more, 13 g ai/ha or more, 13.25 g ai/ha or more, 13.5 g ai/ha or more, 13.75 g ai/ha or more, 14 g ai/ha or more, 14.25 g ai/ha or more, 14.5 g ai/ha or more, 14.75 g ai/ha or more, 15 g ai/ha or more, 15.25 g ai/ha or more, 15.5 g ai/ha or more, 15.75 g ai/ha or more, 16 g ai/ha or more, 16.25 g ai/ha or more, 16.5 g ai/ha or more, 16.75 g ai/ha or more, 17 g ai/ha or more, 17.25 g ai/ha or more, 17.5 g ai/ha or more, 17.75 g ai/ha or more, 18 g ai/ha or more, 18.25 g ai/ha or more, or 18.5 g ai/ha or more).

In some embodiments, the pyroxsulam or agriculturally acceptable salt thereof is applied to vegetation or an area adjacent the vegetation or applied to soil or water to prevent the emergence or growth of vegetation in an amount of 18.75 g ai/ha or less (e.g., 18.5 g ai/ha or less, 18.25 g ai/ha or less, 18 g ai/ha or less, 17.75 g ai/ha or less, 17.5 g ai/ha or less, 17.25 g ai/ha or less, 17 g ai/ha or less, 16.75 g ai/ha or less, 16.5 g ai/ha or less, 16.25 g ai/ha or less, 16 g ai/ha or less, 15.75 g ai/ha or less, 15.5 g ai/ha or less, 15.25 g ai/ha or less, 15 g ai/ha or less, 14.75 g ai/ha or less, 14.5 g ai/ha or less, 14.25 g ai/ha or less, 14 g ai/ha or less, 13.75 g ai/ha or less, 13.5 g ai/ha or less, 13.25 g ai/ha or less, 13 g ai/ha or less, 12.75 g ai/ha or less, 12.5 g ai/ha or less, 12.25 g ai/ha or less, 12 g ai/ha or less, 11.75 g ai/ha or less, 11.5 g ai/ha or less, 11.25 g ai/ha or less, 11 g ai/ha or less, 10.75 g ai/ha or less, 10.5 g ai/ha or less, 10.25 g ai/ha or less, 10 g ai/ha or less, 9.75 g ai/ha or less, 9.5 g ai/ha or less, 9.25 g ai/ha or less, 9 g ai/ha or less, 8.75 g ai/ha or less, 8.5 g ai/ha or less, 8.25 g ai/ha or less, 8 g ai/ha or less, 7.75 g ai/ha or less, 7.5 g ai/ha or less, 7.25 g ai/ha or less, 7 g ai/ha or less, 6.75 g ai/ha or less, 6.5 g ai/ha or less, 6.25 g ai/ha or less, 6 g ai/ha or less, 5.75 g ai/ha or less, 5.5 g ai/ha or less, 5.25 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, 2.75 g ai/ha or less, 2.5 g ai/ha or less, 2.25 g ai/ha or less, or 2 g ai/ha or less).

The pyroxsulam or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the pyroxsulam or agriculturally acceptable salt thereof is applied to vegetation or an area adjacent the vegetation or applied to soil or water to prevent the emergence or growth of vegetation in an amount of 1.9-18.75 g ai/ha (e.g., 2.5-18 g ai/ha, 2.5-17 g ai/ha, 2.75-16 g ai/ha, 2.75-18.75 g ai/ha, 3-18 g ai/ha, 3.25-17 g ai/ha, 3.25-16 g ai/ha, 3.5-18.75 g ai/ha, 3.5-18 g ai/ha, 3.5-17 g ai/ha, 3.5-16 g ai/ha, 3.5-15 g ai/ha, or 3.5-14 g ai/ha).

In certain embodiments, the herbicidal composition comprises a herbicidally effective amount of (a) a pyridine carboxylic acid herbicide or an agriculturally acceptable N-oxide, salt, or ester thereof, and (b) imazamethabenz, imazamox, imazapic, imazapyr, imazaquin, imazethapyr, agriculturally acceptable salts or esters thereof, or combinations thereof.

Imazamethabenz

Compositions and methods of the present disclosure can include imazamethabenz or an agriculturally acceptable salt or ester thereof. Imazamethabenz, shown below, is a mixture of isomers and an imidazolinone that provides post-emergence control of *Avena* species, *Alopecurus myosuroides*, *Apera spica-venti* and dicotyledonous weeds in wheat, barley, rye, and sunflowers. Imazamethabenz, as well as methods of preparing imazamethabenz, are known in the art. Its herbicidal activity is described in *The Pesticide Manual*, Fifteenth Edition, 2009.

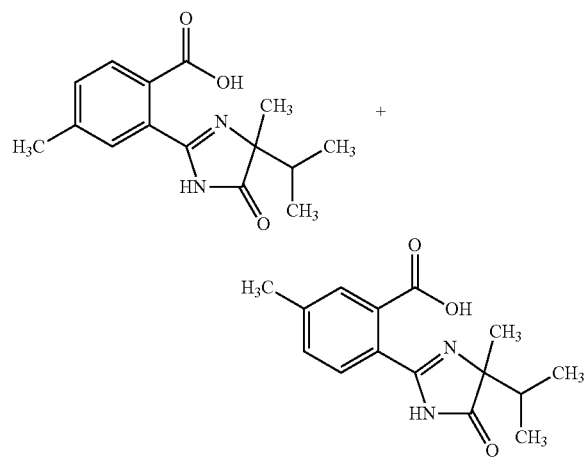

In some embodiments, imazamethabenz can be provided as an agriculturally acceptable salt or ester of imazamethabenz.

The imazamethabenz or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the imazamethabenz or agriculturally acceptable salt or ester thereof is applied to vegetation or an area adjacent the vegetation or applied to soil or water to prevent the emergence or growth of vegetation in an amount of 50 g ai/ha or more (e.g., 55 g ai/ha or more, 60 g ai/ha or more, 65 g ai/ha or more, 70 g ai/ha or more, 75 g ai/ha or more, 80 g ai/ha or more, 85 g ai/ha or more, 90 g ai/ha or more, 95 g ai/ha or more, 100 g ai/ha or more, 110 g ai/ha or more, 120 g ai/ha or more, 130 g ai/ha or more, 140 g ai/ha or more, 150 g ai/ha or more, 160 g ai/ha or more, 170 g ai/ha or more, 180 g ai/ha or more, 190 g ai/ha or more, 200 g ai/ha or more, 210 g ai/ha or more, 220 g ai/ha or more, 230 g ai/ha or more, 240 g ai/ha or more, 250 g ai/ha or more, 260 g ai/ha or more, 270 g ai/ha or more, 280 g ai/ha or more, 290 g ai/ha or more, 300 g ai/ha or more, 310 g ai/ha or more, 320 g ai/ha or more, 330 g ai ha or more, 340 g ai ha or more, 350 g ai/ha or more, 360 g ai/ha or more, 370 g ai/ha or more, 380 g ai/ha or more, 390 g ai/ha or more, 400 g ai/ha or more, 410 g ai/ha or more, 420 g ai/ha or more, 430 g ai/ha or more, 440 g ai/ha or more, 450 g ai/ha or more, 460 g ai/ha or more, 470 g ai/ha or more, 480 g ai/ha or more, 490 g ai/ha or more, 500 g ai/ha or more, 510 g ai/ha or more, 520 g ai/ha or more, 530 g ai/ha or more, 540 g ai/ha or more, 550 g ai/ha or more, 560 g ai/ha or more, 570 g ai/ha or more, 580 g ai/ha or more, 590 g ai/ha or more, 600 g ai/ha or more, 610 g ai/ha or more, 620 g ai/ha or more, 630 g ai/ha or more, 640 g ai ha or more, 650 g ai ha or more, 660 g ai ha or more, 670 g ai/ha or more, 680 g ai ha or more, or 690 g ai/ha or more).

In some embodiments, the imazamethabenz or agriculturally acceptable salt or ester thereof is applied to vegetation or an area adjacent the vegetation or applied to soil or water to prevent the emergence or growth of vegetation in an amount of 700 g ai/ha or less (e.g., 690 g ai/ha or less, 680 g ai/ha or less, 670 g ai/ha or less, 660 g ai/ha or less, 650 g ai/ha or less, 640 g ai/ha or less, 630 g ai/ha or less, 620 g ai/ha or less, 610 g ai/ha or less, 600 g ai/ha or less, 590 g ai/ha or less, 580 g ai/ha or less, 570 g ai/ha or less, 560 g ai/ha or less, 550 g ai/ha or less, 540 g ai ha or less, 530 g ai/ha or less, 520 g ai/ha or less, 510 g ai/ha or less, 500 g ai/ha or less, 490 g ai/ha or less, 480 g ai/ha or less, 470 g ai/ha or less, 460 g ai/ha or less, 450 g ai/ha or less, 440 g ai/ha or less, 430 g ai/ha or less, 420 g ai/ha or less, 410 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, or 55 g ai/ha or less).

The imazamethabenz or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the imazamethabenz or agriculturally acceptable salt or ester thereof is applied to vegetation or an area adjacent the vegetation or applied to soil or water to prevent the emergence or growth of vegetation in an amount of 50-700 g ai/ha (e.g., 50-400 g ai/ha, 400-700 g ai/ha, 50-650 g ai/ha, 50-600 g ai/ha, 50-500 g ai/ha, 60-700 g ai/ha, 60-600 g ai/ha, 60-500 g ai/ha, 70-700 g ai/ha, 70-600 g ai/ha, 70-500 g ai/ha, 70-400 g ai/ha, or 100-500 g ai/ha).

Imazamox

Compositions and methods of the present disclosure can include imazamox or an agriculturally acceptable salt thereof. Imazamox, shown below, is an imidazolinone that provides pre- and post-emergence control of broadleaf and grass weeds, e.g., in rice, maize, rape, alfalfa, peas, and beans. Imazamox, as well as methods of preparing imazamox, are known in the art. Its herbicidal activity is described in *The Pesticide Manual*, Fifteenth Edition, 2009.

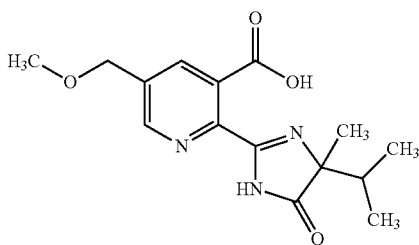 [SMILES: COCc1cnc(C2=NC(C)(C(C)C)C(=O)N2)c(C(=O)O)c1]

In some embodiments, imazamox can be provided as an agriculturally acceptable salt of imazamox.

The imazamox or agriculturally acceptable salt thereof can be applied to vegetation or an area adjacent the vegetation or applied to soil or water to prevent the emergence or growth of vegetation in an amount sufficient to induce a herbicidal effect. In some embodiments, the imazamox or agriculturally acceptable salt thereof is applied to vegetation or an area adjacent the vegetation or applied to soil or water to prevent the emergence or growth of vegetation in an amount of 5 g ai/ha or more (e.g., 6 g ai/ha or more, 7 g ai/ha or more, 8 g ai/ha or more, 9 g ai/ha or more, 10 g ai/ha or more, 11 g ai/ha or more, 12 g ai/ha or more, 13 g ai/ha or more, 14 g ai/ha or more, 15 g ai % ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, or 59 g ai/ha or more).

In some embodiments, the imazamox or agriculturally acceptable salt thereof is applied to vegetation or an area adjacent the vegetation or applied to soil or water to prevent the emergence or growth of vegetation in an amount of 60 g ai/ha or less (e.g., 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, or 6 g ai/ha or less).

The imazamox or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the imazamox or agriculturally acceptable salt thereof is applied to vegetation or an area adjacent the vegetation or applied to soil or water to prevent the emergence or growth of vegetation in an amount of 5-60 g ai/ha (e.g., 5-58 g ai/ha, 5-56 g ai/ha, 5-54 g ai/ha, 5-52 g ai/ha, 5-50 g ai/ha, 5-48 g ai/ha, 5-45 g ai/ha, 6-60 g ai/ha, 6-58 g ai/ha, 6-56 g ai/ha, 6-54 g ai/ha, 7-60 g ai/ha, or 7-58 g ai/ha).

Imazapic

Compositions and methods of the present disclosure can include imazapic or an agriculturally acceptable salt or ester thereof. Imazapic, shown below, is an imidazolinone that provides pre- and post-emergence control of a wide range of annual and perennial weeds in pasture, rangeland, and non-cropland areas. Imazapic, as well as methods of preparing imazapic, are known in the art. Its herbicidal activity is described in *The Pesticide Manual*, Fifteenth Edition, 2009.

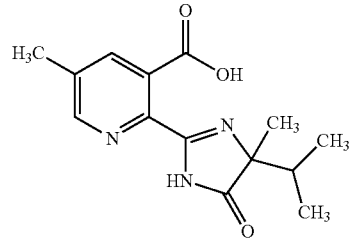 [SMILES: Cc1cnc(C2=NC(C)(C(C)C)C(=O)N2)c(C(=O)O)c1]

In some embodiments, imazapic can be provided as an agriculturally acceptable salt or ester of imazapic.

The imazapic or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the imazapic or agriculturally acceptable salt thereof is applied to vegetation or an area adjacent the vegetation or applied to soil or water to prevent the emergence or growth of vegetation in an amount of 17.5 g ai/ha or more (e.g., 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 35 g ai/ha or more, 40 g ai/ha or more, 45 g ai/ha or more, 50 g ai/ha or more, 55 g ai/ha or more, 60 g ai/ha or more, 65 g ai/ha or more, 70 g ai/ha or more, 75 g ai/ha or more, 80 g ai/ha or more, 85 g ai/ha or more, 90 g ai/ha or more, 95 g ai/ha or more, 100 g ai/ha or more, 105 g ai/ha or more, 110 g ai/ha or more, 115 g ai/ha or more, 120 g ai/ha or more, 125 g ai/ha or more, 130 g ai/ha or more, 135 g ai/ha or more, 140 g ai/ha or more, 145 g ai/ha or more, 150 g ai/ha or more, 155 g ai/ha or more, 160 g ai/ha or more, 165 g ai/ha or more, 170 g ai/ha or more, 175 g ai/ha or more, 180 g ai/ha or more, 185 g ai/ha or more, 190 g ai/ha or more, 195 g ai/ha or more, 200 g ai/ha or more, 205 g ai/ha or more, 210 g ai/ha or more, or 215 g ai/ha or more).

In some embodiments, the imazapic or agriculturally acceptable salt or ester thereof is applied to vegetation or an area adjacent the vegetation or applied to soil or water to prevent the emergence or growth of vegetation in an amount of 220 g ai/ha or less (e.g., 215 g ai/ha or less, 210 g ai/ha or less, 205 g ai/ha or less, 200 g ai/ha or less, 195 g ai/ha or less, 190 g ai/ha or less, 185 g ai/ha or less, 180 g ai/ha or less, 175 g ai/ha or less, 170 g ai/ha or less, 165 g ai/ha or less, 160 g ai/ha or less, 155 g ai/ha or less, 150 g ai/ha or less, 145 g ai/ha or less, 140 g ai/ha or less, 135 g ai/ha or less, 130 g ai/ha or less, 125 g ai/ha or less, 120 g ai/ha or less, 115 g ai/ha or less, 110 g ai/ha or less, 105 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, 35 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, or 18 g ai/ha or less).

The imazapic or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the imazapic or agriculturally acceptable salt or ester thereof is applied to vegetation or an area adjacent the vegetation or applied to soil or water to prevent the emergence or growth of vegetation in an amount of 17.5-220 g ai/ha (e.g., 17.5-210 g ai/ha, 17.5-200 g ai/ha, 18-220 g ai/ha, 18-210 g ai/ha, 18-200 g ai/ha, 18-190 g ai/ha, 20-220 g ai/ha, 20-210 g ai/ha, 20-200 g ai/ha, 20-190 g ai/ha, 20-180 g ai/ha, 25-220 g ai/ha, or 25-200 g ai/ha).

Imazapyr

Compositions and methods of the present disclosure can include imazapyr or an agriculturally acceptable salt or ester thereof. Imazapyr, shown below, is an imidazolinone that provides pre- and post-emergence control of annual and perennial grasses, broadleaf weeds, brush, and trees. Imazapyr, as well as methods of preparing imazapyr, are known in the art. Its herbicidal activity is described in *The Pesticide Manual*, Fifteenth Edition, 2009.

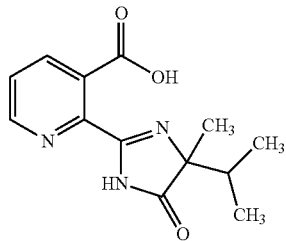 [SMILES: CC(C)C1(C)N=C(c2ncccc2C(=O)O)NC1=O]

In some embodiments, imazapyr can be provided as an agriculturally acceptable salt or ester of imazapyr.

The imazapyr or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the imazapyr or agriculturally acceptable salt or ester thereof is applied to vegetation or an area adjacent the vegetation or applied to soil or water to prevent the emergence or growth of vegetation in an amount of 140 g ai/ha or more (e.g., 145 g ai/ha or more, 150 g ai/ha or more, 155 g ai/ha or more, 160 g ai/ha or more, 165 g ai/ha or more, 170 g ai/ha or more, 175 g ai ha or more, 180 g ai/ha or more, 190 g ai/ha or more, 200 g ai/ha or more, 225 g ai/ha or more, 250 g ai/ha or more, 275 g ai/ha or more, 300 g ai/ha or more, 325 g ai/ha or more, 350 g ai/ha or more, 375 g ai/ha or more, 400 g ai/ha or more, 425 g ai/ha or more, 450 g ai/ha or more, 475 g ai/ha or more, 500 g ai/ha or more, 550 g ai/ha or more, 600 g ai/ha or more, 650 g ai/ha or more, 700 g ai/ha or more, 750 g ai/ha or more, 800 g ai/ha or more, 850 g ai/ha or more, 900 g ai/ha or more, 950 g ai/ha or more, 1000 g ai/ha or more, 1050 g ai/ha or more, 1100 g ai/ha or more, 1150 g ai/ha or more, 1200 g ai/ha or more, 1250 g ai/ha or more, 1300 g ai/ha or more, 1350 g ai/ha or more, 1400 g ai/ha or more, 1450 g ai/ha or more, 1500 g ai/ha or more, 1550 g ai/ha or more, 1600 g ai/ha or more, 1620 g ai/ha or more, 1640 g ai/ha or more, 1660 g ai/ha or more, or 1680 g ai/ha or more).

In some embodiments, the imazapyr or agriculturally acceptable salt or ester thereof is applied to vegetation or an area adjacent the vegetation or applied to soil or water to prevent the emergence or growth of vegetation in an amount of 1700 g ai/ha or less (e.g., 1680 g ai/ha or less, 1660 g ai/ha or less, 1640 g ai/ha or less, 1620 g ai/ha or less, 1600 g ai/ha or less, 1550 g ai/ha or less, 1500 g ai/ha or less, 1450 g ai/ha or less, 1400 g ai/ha or less, 1350 g ai/ha or less, 1300 g ai/ha or less, 1250 g ai/ha or less, 1200 g ai/ha or less, 1150 g ai/ha or less, 1100 g ai/ha or less, 1050 g ai/ha or less, 1000 g ai/ha or less, 950 g ai/ha or less, 900 g ai/ha or less, 850 g ai/ha or less, 800 g ai/ha or less, 750 g ai/ha or less, 700 g ai/ha or less, 650 g ai/ha or less, 600 g ai/ha or less, 550 g ai/ha or less, 500 g ai/ha or less, 475 g ai/ha or less, 450 g ai/ha or less, 425 g ai/ha or less, 400 g ai/ha or less, 375 g ai/ha or less, 350 g ai/ha or less, 325 g ai/ha or less, 300 g ai/ha or less, 275 g ai/ha or less, 250 g ai/ha or less, 225 g ai/ha or less, 200 g ai/ha or less, 190 g ai/ha or less, 180 g ai ha or less, 175 g ai/ha or less, 170 g ai/ha or less, 165 g ai/ha or less, 160 g ai/ha or less, 155 g ai/ha or less, 150 g ai/ha or less, or 145 g ai/ha or less).

The imazapyr or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the imazapyr or agriculturally acceptable salt or ester thereof is applied to vegetation or an area adjacent the vegetation or applied to soil or water to prevent the emergence or growth of vegetation in an amount of 140-1700 g ai/ha (e.g., 140-850 g ai/ha, 850-1700 g ai/ha, 140-1600 g ai/ha, 140-1500 g ai/ha, 140-1400 g ai/ha, 140-1200 g ai/ha, 140-1000 g ai/ha, 150-1700 g ai/ha, 150-1500 g ai/ha, 150-1250 g ai/ha, 150-1000 g ai/ha, 175-1500 g ai/ha, or 175-1000 g ai/ha).

Imazethapyr

Compositions and methods of the present disclosure can include imazethapyr or an agriculturally acceptable salt or ester thereof. Imazethapyr, shown below, is an imidazolinone that controls many major annual and perennial grass and broadleaf weeds in most major crops.

Imazethapyr, as well as methods of preparing imazethapyr, are known in the art. Its herbicidal activity is described in *The Pesticide Manual*, Fifteenth Edition, 2009.

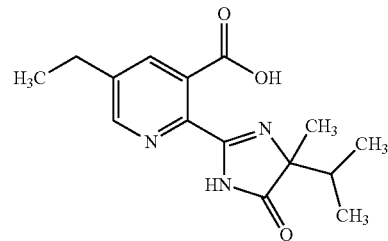 [SMILES: CCc1cnc(C2=NC(C)(C(C)C)C(=O)N2)c(C(=O)O)c1]

In some embodiments, imazethapyr can be provided as an agriculturally acceptable salt or ester of imazethapyr.

The imazethapyr or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the imazethapyr or agriculturally acceptable salt or ester thereof is applied to vegetation or an area adjacent the vegetation or applied to soil or water to prevent the emergence or growth of vegetation in an amount of 8.75 g ai/ha or more (e.g., 9 g ai/ha or more, 9.5 g ai/ha or more, 10 g ai/ha or more, 10.5 g ai/ha or more, 11 g ai/ha or more, 11.5 g ai/ha or more, 12 g ai/ha or more, 12.5 g ai/ha or more, 13 g ai/ha or more, 13.5 g ai/ha or more, 14 g ai/ha or more, 14.5 g ai/ha or more, 15 g ai/ha or more, 15.5 g ai/ha or more, 16 g ai/ha or more, 16.5 g ai/ha or more, 17 g ai/ha or more, 17.5 g ai/ha or more, 18 g ai/ha or more, 18.5 g ai/ha or more, 19 g ai/ha or more, 19.5 g ai/ha or more, 20 g ai/ha or more, 21 g ai/ha or more, 22 g ai/ha or more, 23 g ai/ha or more, 24 g ai/ha or more, 25 g ai/ha or more, 30 g ai/ha or more, 35 g ai/ha or more, 40 g ai/ha or more, 45 g ai/ha or more, 50 g ai/ha or more, 60 g ai/ha or more, 70 g ai/ha or more, 80 g ai/ha or more, 90 g ai/ha or more, 100 g ai/ha or more, 110 g ai/ha or more, 120 g ai/ha or more, 130 g ai/ha or more, 140 g ai/ha or more, 150 g ai/ha or more, 160 g ai/ha or more, 170 g ai/ha or more, 180 g ai/ha or more, 190 g ai/ha or more, 200 g ai/ha or more, 210 g ai/ha or more, 220 g ai/ha or more, 230 g ai/ha or more, 240 g ai/ha or more, 250 g ai/ha or more, 260 g ai/ha or more, 270 g ai/ha or more, 272 g ai/ha or more, 274 g ai/ha or more, 276 g ai/ha or more, or 278 g ai/ha or more).

In some embodiments, the imazethapyr or agriculturally acceptable salt or ester thereof is applied to vegetation or an area adjacent the vegetation or applied to soil or water to prevent the emergence or growth of vegetation in an amount of 280 g ai/ha or less (e.g., 278 g ai/ha or less, 276 g ai/ha or less, 274 g ai/ha or less, 272 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 90 g ai/ha or less, 80 g ai/ha or less, 70 g ai/ha or less, 60 g ai/ha or less, 50 g ai/ha or less, 45 g ai/ha or less, 40 g ai/ha or less, 35 g ai/ha or less, 30 g ai/ha or less, 25 g ai/ha or less, 24 g ai/ha or less, 23 g ai/ha or less, 22 g ai/ha or less, 21 g ai/ha or less, 20 g ai/ha or less, 19.5 g ai/ha or less, 19 g ai/ha or less, 18.5 g ai/ha or less, 18 g ai/ha or less, 17.5 g ai/ha or less, 17 g ai/ha or less, 16.5 g ai/ha or less, 16 g ai/ha or less, 15.5 g ai/ha or less, 15 g ai/ha or less, 14.5 g ai/ha or less, 14 g ai/ha or less, 13.5 g ai/ha or less, 13 g ai/ha or less, 12.5 g ai/ha or less, 12 g ai/ha or less, 11.5 g ai/ha or less, 11 g ai/ha or less, 10.5 g ai/ha or less, 10 g ai/ha or less, 9.5 g ai/ha or less, or 9 g ai/ha or less).

The imazethapyr or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the imazethapyr or agriculturally acceptable salt or ester thereof is applied to vegetation or an area adjacent the vegetation or applied to soil or water to prevent the emergence or growth of vegetation in an amount of 8.75-280 g ai/ha (e.g., 8.75-275 g ai/ha, 8.75-270 g ai/ha, 8.75-260 g ai/ha, 8.75-250 g ai/ha, 8.75-225 g ai/ha, 8.75-200 g ai/ha, 10-280 g ai/ha, 10-250 g ai/ha, 10-200 g ai/ha, 15-280 g ai/ha, 15-250 g ai/ha, 15-200 g ai/ha, or 17.5-250 g ai/ha).

In certain embodiments, the herbicidal composition comprises a herbicidally effective amount of (a) a pyridine carboxylic acid herbicide or an agriculturally acceptable N-oxide, salt, or ester thereof, and (b) bispyribac, pyribenzoxim, pyriftalid, pyriminobac, pyrimisulfan, pyrithiobac, agriculturally acceptable salts or esters thereof, or combinations thereof.

Bispyribac

Compositions and methods of the present disclosure can include bispyribac or an agriculturally acceptable salt thereof. Bispyribac-sodium, shown below, is a pyrimidinyl oxybenzoate that provides control of grasses, sedges, and broadleaf weeds. e.g., in direct-seeded and water-seeded rice and in turf. Bispyribac-sodium, as well as methods of preparing bispyribac-sodium, are known in the art. Its herbicidal activity is described in *The Pesticide Manual*, Fifteenth Edition, 2009.

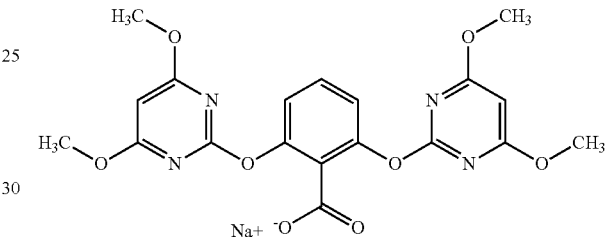

The bispyribac or agriculturally acceptable salt thereof can be applied to vegetation or an area adjacent the vegetation or applied to soil or water to prevent the emergence or growth of vegetation in an amount sufficient to induce a herbicidal effect. In some embodiments, the bispyribac or agriculturally acceptable salt thereof is applied to vegetation or an area adjacent the vegetation or applied to soil or water to prevent the emergence or growth of vegetation in an amount of 5 g ai/ha or more (e.g., 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, or 59 g ai/ha or more).

In some embodiments, the bispyribac or agriculturally acceptable salt thereof is applied to vegetation or an area adjacent the vegetation or applied to soil or water to prevent the emergence or growth of vegetation in an amount of 60 g ai/ha or less (e.g., 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, or 5.5 g ai/ha or less).

The bispyribac or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the bispyribac or agriculturally acceptable salt thereof is applied to vegetation or an area adjacent the vegetation or applied to soil or water to prevent the emergence or growth of vegetation in an amount of 5-60 g ai/ha (e.g., 5-58 g ai/ha, 5-56 g ai/ha, 5-54 g ai/ha, 5-52 g ai/ha, 5-50 g ai/ha, 6-60 g ai/ha, 6-58 g ai/ha, 6-56 g ai/ha, 6-55 g ai/ha, 7.5-60 g ai/ha, 7.5-55 g ai/ha, 7.5-50 g ai/ha, or 8-50 g ai/ha).

Pyribenzoxim

Compositions and methods of the present disclosure can include pyribenzoxim. Pyribenzoxim, shown below, is a pyrimidinyl oxybenzoate that provides post-emergence control of barnyard grass, blackgrass, and polygonums, e.g., in rice, wheat, and zoysiagrass. Pyribenzoxim, as well as methods of preparing pyribenzoxim, are known in the art. Its herbicidal activity is described, for example, in *The Pesticide Manual*, Fifteenth Edition, 2009.

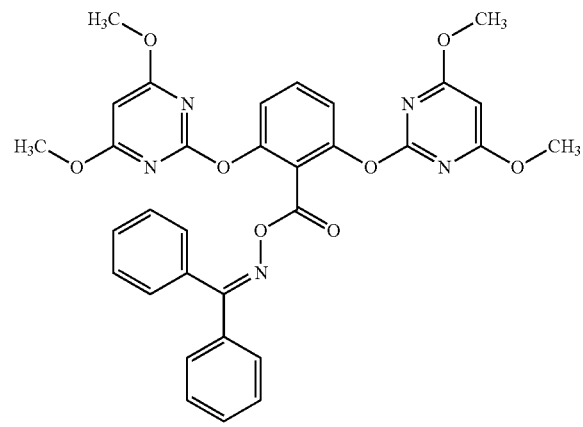

The pyribenzoxim or agriculturally acceptable salt thereof can be applied to vegetation or an area adjacent the vegetation or applied to soil or water to prevent the emergence or growth of vegetation in an amount sufficient to induce a herbicidal effect. In some embodiments, the pyribenzoxim or agriculturally acceptable salt thereof is applied to vegetation or an area adjacent the vegetation or applied to soil or water to prevent the emergence or growth of vegetation in an amount of 7.5 g ai/ha or more (e.g., 7.75 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai/ha or more, or 69 g ai/ha or more).

In some embodiments, the pyribenzoxim or agriculturally acceptable salt thereof is applied to vegetation or an area adjacent the vegetation or applied to soil or water to prevent the emergence or growth of vegetation in an amount of 70 g ai/ha or less (e.g., 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, or 7.75 g ai/ha or less).

The pyribenzoxim or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the pyribenzoxim is applied to vegetation or an area adjacent the vegetation or applied to soil or water to prevent the emergence or growth of vegetation in an amount of 7.5-70 g ai/ha (e.g., 7.5-68 g ai/ha, 7.5-65 g ai/ha, 7.75-60 g ai/ha, 9-70 g ai/ha, 9-68 g ai/ha, 9-65 g ai/ha, 9-60 g ai ha, 10-70 g ai/ha, 10-68 g ai/ha, 10-65 g ai/ha, 10-60 g ai/ha, 20-60 g ai/ha, or 20-50 g ai/ha).

In certain embodiments, the herbicidal composition comprises a herbicidally effective amount of (a) a pyridine carboxylic acid herbicide or an agriculturally acceptable N-oxide, salt, or ester thereof, and (b) flucarbazone, propoxycarbazone, thiencarbazone, agriculturally acceptable salts or esters thereof, or combinations thereof.

Flucarbazone

Compositions and methods of the present disclosure can include flucarbazone or an agriculturally acceptable salt thereof. Flucarbazone, shown below, is a sulfonylaminocarbonyl triazolinone that provides post-emergence control of annual grass weeds and some perennial grass weeds and some broad-leaved weeds. Flucarbazone, as well as methods of preparing flucarbazone, are known in the art. Its herbicidal activity is described in *The Pesticide Manual*, Fifteenth Edition, 2009.

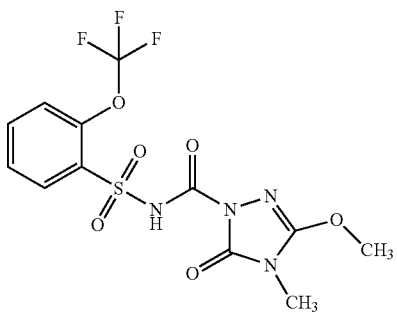 [SMILES: COc1nn(C(=O)NS(=O)(=O)c2ccccc2OC(F)(F)F)c(=O)n1C]

In some embodiments, flucarbazone can be provided as an agriculturally acceptable salt of flucarbazone.

The flucarbazone or agriculturally acceptable salt thereof can be applied to vegetation or an area adjacent the vegetation or applied to soil or water to prevent the emergence or growth of vegetation in an amount sufficient to induce a herbicidal effect. In some embodiments, the flucarbazone or agriculturally acceptable salt thereof is applied to vegetation or an area adjacent the vegetation or applied to soil or water to prevent the emergence or growth of vegetation in an amount of 3.75 g ai/ha or more (e.g., 4 g ai/ha or more, 4.25 g ai/ha or more, 4.5 g ai/ha or more, 4.75 g ai/ha or more, 5 g ai/ha or more, 5.25 g ai/ha or more, 5.5 g ai/ha or more, 5.75 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 12.5 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 25.5 g ai/ha or more, 26 g ai/ha or more, 26.5 g ai/ha or more, 27 g ai/ha or more, 27.5 g ai/ha or more, 28 g ai/ha or more, 28.5 g ai/ha or more, 29 g ai/ha or more, 29.25 g ai/ha or more, 29.5 g ai/ha or more, or 29.75 g ai/ha or more).

In some embodiments, the flucarbazone or agriculturally acceptable salt thereof is applied to vegetation or an area adjacent the vegetation or applied to soil or water to prevent the emergence or growth of vegetation in an amount of 30 g ai/ha or less (e.g., 29.75 g ai/ha or less, 29.5 g ai/ha or less, 29.25 g ai/ha or less, 29 g ai/ha or less, 28.5 g ai/ha or less, 28 g ai/ha or less, 27.5 g ai/ha or less, 27 g ai/ha or less, 26.5 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.75 g ai/ha or less, 5.5 g ai/ha or less, 5.25 g ai/ha or less, 5 g ai/ha or less, 4.75 g ai/ha or less, 4.5 g ai/ha or less, 4.25 g ai/ha or less, or 4 g ai/ha or less).

The flucarbazone or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the flucarbazone or agriculturally acceptable salt thereof is applied to vegetation or an area adjacent the vegetation or applied to soil or water to prevent the emergence or growth of vegetation in an amount of 3.75-30 g ai/ha (e.g., 3.75-29 g ai/ha, 3.75-28 g ai/ha, 3.75-27 g ai/ha, 3.75-25 g ai/ha, 4-30 g ai/ha, 4-28 g ai/ha, 4-26 g ai/ha, 4-25 g ai/ha, 5-30 g ai/ha, 5-28 g ai/ha, 5-25 g ai/ha, 6-30 g ai/ha, or 6-25 g ai/ha).

Propoxycarbazone

Compositions and methods of the present disclosure can include propoxycarbazone or an agriculturally acceptable salt thereof. Propoxycarbazone, shown below, is a sulfonylaminocarbonyl triazolinone that provides post-emergence control of grass weeds and some broad-leaved weeds. Propoxycarbazone, as well as methods of preparing propoxycarbazone, are known in the art. Its herbicidal activity is described in *The Pesticide Manual*, Fifteenth Edition, 2009.

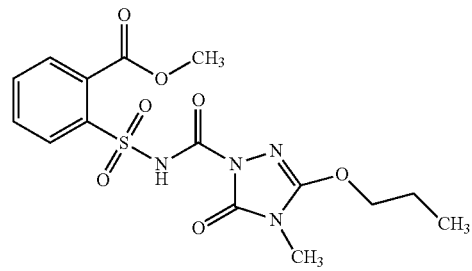 [SMILES: CCCOc1nn(C(=O)NS(=O)(=O)c2ccccc2C(=O)OC)c(=O)n1C]

In some embodiments, propoxycarbazone can be provided as an agriculturally acceptable salt of propoxycarbazone.

The propoxycarbazone or agriculturally acceptable salt thereof can be applied to vegetation or an area adjacent the vegetation or applied to soil or water to prevent the emergence or growth of vegetation in an amount sufficient to induce a herbicidal effect. In some embodiments, the propoxycarbazone or agriculturally acceptable salt thereof is applied to vegetation or an area adjacent the vegetation or applied to soil or water to prevent the emergence or growth of vegetation in an amount of 3.75 g ai/ha or more (e.g., 4 g ai/ha or more, 4.25 g ai/ha or more, 4.5 g ai/ha or more, 4.75 g ai/ha or more, 5 g ai ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai % ha or more, or 69 g ai/ha or more).

In some embodiments, the propoxycarbazone or agriculturally acceptable salt thereof is applied to vegetation or an area adjacent the vegetation or applied to soil or water to prevent the emergence or growth of vegetation in an amount of 70 g ai/ha or less (e.g., 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 57 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, 4.5 g ai/ha or less, 4.25 g ai/ha or less, or 4 g ai/ha or less).

The propoxycarbazone or agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the propoxycarbazone or agriculturally acceptable salt thereof is applied to vegetation or an area adjacent the vegetation or applied to soil or water to prevent the emergence or growth of vegetation in an amount of 3.75-70 g ai/ha (e.g., 3.75-68 g ai/ha, 3.75-66 g ai/ha, 3.75-64 g ai/ha, 3.75-62 g ai/ha, 3.75-60 g ai/ha, 4-70 g ai/ha, 4-65 g ai/ha, 4-60 g ai/ha, 5-70 g ai/ha, 5-65 g ai/ha, 5-60 g ai/ha, 5-50 g ai/ha, or 7.5-50 g ai/ha).

Thiencarbazone

Compositions and methods of the present disclosure can include thiencarbazone or an agriculturally acceptable salt or ester thereof. Thiencarbazone-methyl, shown below, is a sulfonylaminocarbonyl triazolinone that provides postemergence control of grass weeds and some broad-leaved weeds. Thiencarbazone, as well as methods of preparing thiencarbazone, are known in the art. Its herbicidal activity is described in *The Pesticide Manual*, Fifteenth Edition, 2009.

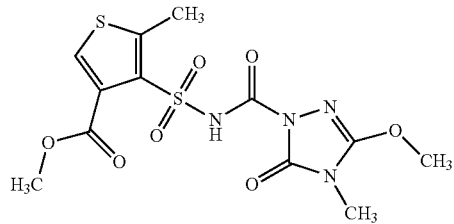

In some embodiments, thiencarbazone can be provided as an agriculturally acceptable salt or ester of thiencarbazone.

The thiencarbazone or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the thiencarbazone or agriculturally acceptable salt or ester thereof is applied to vegetation or an area adjacent the vegetation or applied to soil or water to prevent the emergence or growth of vegetation in an amount of 2.5 g ai/ha or more (e.g., 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, or 44 g ai/ha or more).

In some embodiments, the thiencarbazone or agriculturally acceptable salt thereof is applied to vegetation or an area adjacent the vegetation or applied to soil or water to prevent the emergence or growth of vegetation in an amount of 45 g ai/ha or less (e.g., 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, or 2.75 g ai/ha or less).

The thiencarbazone or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the thiencarbazone or agriculturally acceptable salt thereof is applied to vegetation or an area adjacent the vegetation or applied to soil or water to prevent the emergence or growth of vegetation in an amount of 2.5-45 g ai/ha (e.g., 2.5-42 g ai/ha, 2.5-40 g ai/ha, 2.75-45 g ai/ha, 2.75-40 g ai/ha, 3-45 g ai/ha, 3.25-45 g ai/ha, 3.25-40 g ai/ha, 3.5-45 g ai/ha, 3.5-40 g ai/ha, 3.5-35 g ai/ha, 3.75-45 g ai/ha, 3.75-40 g ai/ha, or 5-40 g ai/ha).

In certain embodiments, the herbicidal composition comprises a herbicidally effective amount of (a) a pyridine carboxylic acid herbicide or an agriculturally acceptable N-oxide, salt, or ester thereof, and (b) amidosulfuron, azimsulfuron, bensulfuron, chlorimuron, chlorsulfuron, cinosulfuron, cyclosulfamuron, ethametsulfuron, ethoxysulfuron, flazasulfuron, flucetosulfuron, flupyrsulfuron, foramsulfuron, halosulfuron, imazosulfuron, iodosulfuron, iofensulfuron, mesosulfuron, metazosulfuron, metsulfuron, nicosulfuron, orthosulfamuron, oxasulfuron, primisulfuron, propyrisulfuron, prosulfuron, pyrazosulfuron, rimsulfuron, sulfometuron, sulfosulfuron, triasulfuron, tribenuron, thifensulfuron, trifloxysulfuron, triflusulfuron, tritosulfuron, agriculturally acceptable salts or esters thereof, or combinations thereof.

Amidosulfuron

Compositions and methods of the present disclosure can include amidosulfuron or an agriculturally acceptable salt thereof. Amidosulfuron, shown below, is a sulfonylurea that provides post-emergence control of a wide range of broadleaf weeds, e.g., cleavers, in winter wheat, durum wheat, barley, rye, triticale, and oats. Amidosulfuron, as well as methods of preparing amidosulfuron, are known in the art. Its herbicidal activity is described in *The Pesticide Manual*, Fifteenth Edition, 2009.

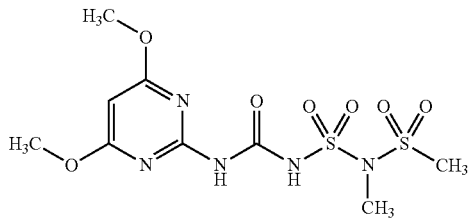

In some embodiments, amidosulfuron can be provided as an agriculturally acceptable salt of amidosulfuron.

The amidosulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the amidosulfuron or agriculturally acceptable salt thereof is applied to vegetation or an area adjacent the vegetation or applied to soil or water to prevent the emergence or growth of vegetation in an amount of 3.75 g ai/ha or more (e.g., 4 g ai/ha or more, 4.25 g ai/ha or more, 4.5 g ai/ha or more, 4.75 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, or 59 g ai/ha or more).

In some embodiments, the amidosulfuron or agriculturally acceptable salt thereof is applied to vegetation or an area adjacent the vegetation or applied to soil or water to prevent the emergence or growth of vegetation in an amount of 60 g ai/ha or less (e.g., 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, 4.5 g ai/ha or less, 4.25 g ai/ha or less, or 4 g ai/ha or less).

The amidosulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the amidosulfuron or agriculturally acceptable salt thereof is applied to vegetation or an area adjacent the vegetation or applied to soil or water to prevent the emergence or growth of vegetation in an amount of 3.75-60 g ai/ha (e.g., 3.75-58 g ai/ha, 3.75-55 g ai/ha, 3.75-50 g ai/ha, 4-60 g ai/ha, 4-55 g ai/ha, 4-50 g ai/ha, 4.25-60 g ai/ha, 4.25-55 g ai/ha, 4.25-50 g ai/ha, 4.5-60 g ai/ha, 4.5-55 g ai/ha, 4.5-50 g ai/ha, or 5-50 g ai/ha).

Azimsulfuron

Compositions and methods of the present disclosure can include azimsulfuron or an agriculturally acceptable salt thereof. Azimsulfuron, shown below, is a sulfonylurea that provides e.g., post-emergence control of annual and perennial broadleaf and sedge weeds in rice. Azimsulfuron, as well as methods of preparing azimsulfuron, are known in the art. Its herbicidal activity is described in *The Pesticide Manual*, Fifteenth Edition, 2009.

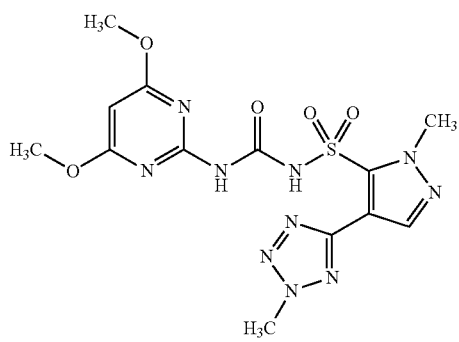 [SMILES: COc1cc(OC)nc(NC(=O)NS(=O)(=O)c2c(-c3nnn(C)n3)cnn2C)n1]

In some embodiments, azimsulfuron can be provided as an agriculturally acceptable salt of azimsulfuron.

The azimsulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the azimsulfuron or agriculturally acceptable salt thereof is applied to vegetation or an area adjacent the vegetation or applied to soil or water to prevent the emergence or growth of vegetation in an amount of 3.125 g ai/ha or more (e.g., 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 20.5 g ai/ha or more, 21 g ai/ha or more, 21.5 g ai/ha or more, 22 g ai/ha or more, 22.5 g ai/ha or more, 22.75 g ai/ha or more, 23 g ai/ha or more, 23.25 g ai/ha or more, 23.5 g ai/ha or more, 23.75 g ai/ha or more, 24 g ai/ha or more, 24.25 g ai/ha or more, 24.5 g ai/ha or more, or 24.75 g ai/ha or more).

In some embodiments, the azimsulfuron or agriculturally acceptable salt thereof is applied to vegetation or an area adjacent the vegetation or applied to soil or water to prevent the emergence or growth of vegetation in an amount of 25 g ai/ha or less (e.g., 24.75 g ai/ha or less, 24.5 g ai/ha or less, 24.25 g ai/ha or less, 24 g ai/ha or less, 23.75 g ai/ha or less, 23.5 g ai/ha or less, 23.25 g ai/ha or less, 23 g ai/ha or less, 22.75 g ai/ha or less, 22.5 g ai/ha or less, 22 g ai/ha or less, 21.5 g ai/ha or less, 21 g ai/ha or less, 20.5 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, or 3.25 g ai/ha or less).

The azimsulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the azimsulfuron or agriculturally acceptable salt thereof is applied to vegetation or an area adjacent the vegetation or applied to soil or water to prevent the emergence or growth of vegetation in an amount of 3.125-25 g ai/ha (e.g., 3.125-24 g ai/ha, 3.125-23 g ai/ha, 3.125-22 g ai/ha, 3.125-20 g ai/ha, 3.5-25 g ai/ha, 3.5-22 g ai/ha, 3.5-20 g ai/ha, 4-25 g ai/ha, 4-22 g ai/ha, 4-20 g ai/ha, 4.5-25 g ai/ha, 4.5-20 g ai/ha, or 5-20 g ai/ha).

Bensulfuron

Compositions and methods of the present disclosure can include bensulfuron or an agriculturally acceptable salt or ester thereof. Bensulfuron-methyl, shown below, is a sulfonylurea that provides e.g., pre- and post-emergence control of annual and perennial broadleaf weeds and sedges in rice. Bensulfuron, as well as methods of preparing bensulfuron, are known in the art. Its herbicidal activity is described in *The Pesticide Manual*, Fifteenth Edition, 2009.

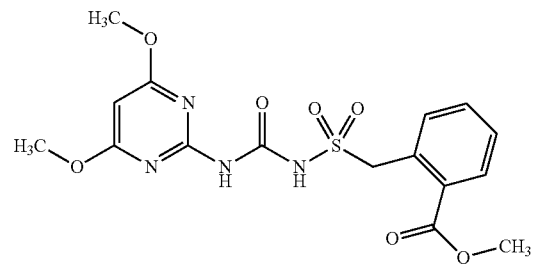

In certain embodiments, the free carboxylic acid, with respect to the methyl ester moiety, i.e., α-(4,6-dimethoxypyrimidin-2-ylcarbamoylsulfamoyl)-o-toluic acid, or its salt, is utilized. In certain embodiments, a different ester, e.g., an alkyl or aralkyl ester is utilized.

The bensulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the bensulfuron or agriculturally acceptable salt or ester thereof is applied to vegetation or an area adjacent the vegetation or applied to soil or water to prevent the emergence or growth of vegetation in an amount of 8.75 g ai/ha or more (e.g., 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai/ha or more, or 69 g ai/ha or more).

In some embodiments, the bensulfuron or agriculturally acceptable salt or ester thereof is applied to vegetation or an area adjacent the vegetation or applied to soil or water to prevent the emergence or growth of vegetation in an amount of 70 g ai/ha or less (e.g., 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, or 9 g ai/ha or less).

The bensulfuron or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the bensulfuron or agriculturally acceptable salt or ester thereof is applied to vegetation or an area adjacent the vegetation or applied to soil or water to prevent the emergence or growth of vegetation in an amount of 8.75-70 g ai/ha (e.g., 8.75-68 g ai/ha, 8.75-65 g ai/ha, 9-60 g ai/ha, 10-70 g ai/ha, 10-68 g ai/ha, 10-65 g ai/ha, 10-60 g ai/ha, 11-70 g ai/ha, 11-68 g ai/ha, 11-65 g ai/ha, 11-60 g ai/ha, 20-60 g ai/ha, or 20-50 g ai/ha).

Chlorsulfuron

Compositions and methods of the present disclosure can include chlorsulfuron or an agriculturally acceptable salt thereof. Chlorsulfuron, shown below, is a sulfonylurea that provides control of e.g., broadleaf weeds and annual grasses in wheat, barley, oats, rye, triticale, flax, and on non-crop land. Chlorsulfuron, as well as methods of preparing chlorsulfuron, are known in the art. Its herbicidal activity is described in *The Pesticide Manual*, Fifteenth Edition, 2009.

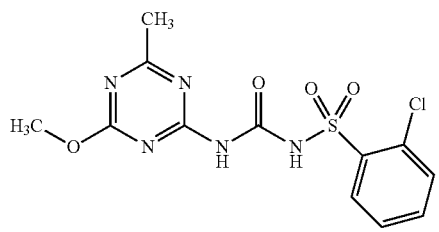 [SMILES: COc1nc(C)nc(NC(=O)NS(=O)(=O)c2ccccc2Cl)n1]

In some embodiments, chlorsulfuron can be provided as an agriculturally acceptable salt of chlorsulfuron.

The chlorsulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the chlorsulfuron or agriculturally acceptable salt thereof is applied to vegetation or an area adjacent the vegetation or applied to soil or water to prevent the emergence or growth of vegetation in an amount of 1.1 g ai/ha or more (e.g., 1.25 g ai/ha or more, 1.5 g ai/ha or more, 1.75 g ai/ha or more, 2 g ai/ha or more, 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 25 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, or 51.5 g ai/ha or more).

In some embodiments, the chlorsulfuron or agriculturally acceptable salt thereof is applied to vegetation or an area adjacent the vegetation or applied to soil or water to prevent the emergence or growth of vegetation in an amount of 52 g ai/ha or less (e.g., 51.5 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less. 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, 4.5 g ai/ha or less, or 4.25 g ai/ha or less, 4 g ai/ha or less, 3.75 g ai/ha or less, 3.5 g ai/ha or less, 3.25 g ai/ha or less, 3 g ai/ha or less, 2.75 g ai/ha or less, 2.5 g ai/ha or less, 2.25 g ai/ha or less, 2 g ai/ha or less, 1.75 g ai/ha or less, 1.5 g ai/ha or less, or 1.25 g ai/ha or less).

The chlorsulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the chlorsulfuron or agriculturally acceptable salt thereof is applied to vegetation or an area adjacent the vegetation or applied to soil or water to prevent the emergence or growth of vegetation in an amount of 1.1-52 g ai/ha (e.g., 1.1-52 g ai/ha, 1.1-50 g ai/ha, 1.5-52 g ai/ha, 1.5-50 g ai/ha, 2-52 g ai/ha, 2-50 g ai/ha, 2.5-52 g ai/ha, 2.5-52 g ai/ha, 3-52 g ai/ha, 3-50 g ai/ha, 3-45 g ai/ha, 3.5-52 g ai/ha, or 3.5-50 g ai/ha).

Ethoxysulfuron

Compositions and methods of the present disclosure can include ethoxysulfuron or an agriculturally acceptable salt thereof. Ethoxysulfuron, shown below, is a sulfonylurea that provides, e.g., control of broadleaf and sedge weeds in cereals, rice, and sugar cane. Ethoxysulfuron, as well as methods of preparing ethoxysulfuron, are known in the art. Its herbicidal activity is described in *The Pesticide Manual*, Fifteenth Edition, 2009.

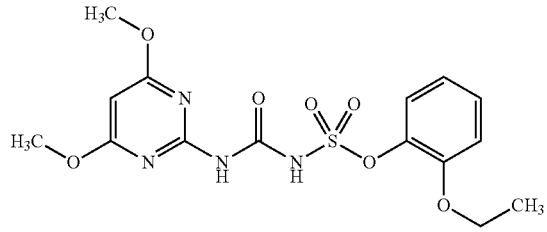 [SMILES: CCOc1ccccc1OS(=O)(=O)NC(=O)Nc1nc(OC)cc(OC)n1]

In some embodiments, ethoxysulfuron can be provided as an agriculturally acceptable salt of ethoxysulfuron.

The ethoxysulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the ethoxysulfuron or agriculturally acceptable salt thereof is applied to vegetation or an area adjacent the vegetation or applied to soil or water to prevent the emergence or growth of vegetation in an amount of 5 g ai/ha or more (e.g., 6 g ai/ha or more, 7 g ai/ha or more, 8 g ai/ha or more, 9 g ai/ha or more, 10 g ai/ha or more, 11 g ai/ha or more, 12 g ai/ha or more, 13 g ai % ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 22 g ai/ha or more, 24 g ai/ha or more, 26 g ai/ha or more, 28 g ai/ha or more, 30 g ai/ha or more, 32 g ai/ha or more, 34 g ai/ha or more, 36 g ai/ha or more, 38 g ai/ha or more, 40 g ai/ha or more, 45 g ai/ha or more, 50 g ai/ha or more, 55 g ai/ha or more, 60 g ai/ha or more, 65 g ai ha or more, 70 g ai ha or more, 75 g ai/ha or more, 80 g ai/ha or more, 85 g ai/ha or more, 90 g ai/ha or more, 95 g ai/ha or more, 100 g ai/ha or more, 101 g ai/ha or more, 102 g ai/ha or more, 103 g ai/ha or more, 104 g ai/ha or more, 105 g ai/ha or more, 106 g ai/ha or more, 107 g ai/ha or more, 108 g ai/ha or more, 109 g ai/ha or more, 110 g ai/ha or more, 111 g ai ha or more, 112 g ai ha or more, 113 g ai ha or more, 114 g ai ha or more, 115 g ai/ha or more, 116 g ai/ha or more, 117 g ai/ha or more, 118 g ai/ha or more, or 119 g ai/ha or more).

In some embodiments, the ethoxysulfuron or agriculturally acceptable salt thereof is applied to vegetation or an area adjacent the vegetation or applied to soil or water to prevent the emergence or growth of vegetation in an amount of 120 g ai/ha or less (e.g., 119 g ai/ha or less, 118 g ai/ha or less, 117 g ai/ha or less, 116 g ai/ha or less, 115 g ai/ha or less, 114 g ai/ha or less, 113 g ai/ha or less, 112 g ai/ha or less, 111 g ai/ha or less, 110 g ai/ha or less, 109 g ai/ha or less, 108 g ai/ha or less, 107 g ai/ha or less, 106 g ai/ha or less, 105 g ai/ha or less, 104 g ai/ha or less, 103 g ai/ha or less, 102 g ai/ha or less, 101 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, 38 g ai/ha or less, 36 g ai/ha or less, 34 g ai/ha or less, 32 g ai/ha or less, 30 g ai/ha or less, 28 g ai/ha or less, 26 g ai/ha or less, 24 g ai ha or less, 22 g ai/ha or less, 20 g ai/ha or less, 19 g ai ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, or 6 g ai/ha or less).

The ethoxysulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the ethoxysulfuron or agriculturally acceptable salt thereof is applied to vegetation or an area adjacent the vegetation or applied to soil or water to prevent the emergence or growth of vegetation in an amount of 5-120 g ai/ha (e.g., 5-110 g ai/ha, 5-100 g ai/ha, 5-90 g ai/ha, 8-120 g ai/ha, 8-100 g ai/ha, 8-80 g ai/ha, 10-120 g ai/ha, 10-100 g ai/ha, 10-80 g ai/ha, 15-120 g ai/ha, 15-100 g ai/ha, 15-80 g ai/ha, or 20-100 g ai/ha).

Flupyrsulfuron

Compositions and methods of the present disclosure can include flupyrsulfuron or an agriculturally acceptable salt or ester thereof. Flupyrsulfuron-methyl sodium, shown below, is a sulfonylurea that is used, e.g., for post-emergent control of grass and broadleaf weeds in cereals. Flupyrsulfuron, as well as methods of preparing flupyrsulfuron, are known in the art. Its herbicidal activity is described in *The Pesticide Manual*, Fifteenth Edition, 2009.

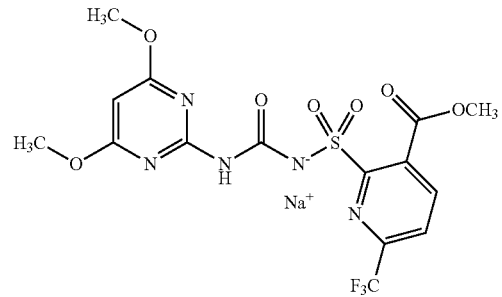 [SMILES: COC(=O)c1ccc(C(F)(F)F)nc1S(=O)(=O)[N-]C(=O)Nc1nc(OC)cc(OC)n1 ; [Na+]]

In certain embodiments, the carboxylic acid or a salt thereof, or a different ester, e.g., alkyl or aralkyl ester, with respect to the methyl ester moiety is utilized. In certain embodiments, a different salt or non-ionic form is utilized.

The flupyrsulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the flupyrsulfuron or agriculturally acceptable salt or ester thereof is applied to vegetation or an area adjacent the vegetation or applied to soil or water to prevent the emergence or growth of vegetation in an amount of 2.5 g ai/ha or more (e.g., 2.55 g ai/ha or more, 2.6 g ai/ha or more, 2.65 g ai/ha or more, 2.7 g ai/ha or more, 2.75 g ai/ha or more, 2.8 g ai/ha or more, 2.85 g ai/ha or more, 2.9 g ai/ha or more, 2.95 g ai/ha or more, 3.0 g ai/ha or more, 3.05 g ai/ha or more, 3.1 g ai/ha or more, 3.15 g ai/ha or more, 3.2 g ai/ha or more, 3.25 g ai/ha or more, 3.3 g ai/ha or more, 3.35 g ai/ha or more, 3.4 g ai/ha or more, 3.45 g ai/ha or more, 3.5 g ai/ha or more, 3.6 g ai/ha or more, 3.7 g ai/ha or more, 3.8 g ai/ha or more, 3.9 g ai/ha or more, 4 g ai/ha or more, 4.1 g ai/ha or more, 4.2 g ai/ha or more, 4.3 g ai/ha or more, 4.4 g ai/ha or more, 4.5 g ai/ha or more, 4.6 g ai/ha or more, 4.7 g ai/ha or more, 4.8 g ai/ha or more, 4.9 g ai/ha or more, 5 g ai/ha or more, 5.1 g ai/ha or more, 5.2 g ai/ha or more, 5.3 g ai/ha or more, 5.4 g ai/ha or more, 5.5 g ai/ha or more, 5.6 g ai/ha or more, 5.7 g ai/ha or more, 5.8 g ai/ha or more, 5.9 g ai/ha or more, 6 g ai/ha or more, 6.1 g ai/ha or more, 6.2 g ai/ha or more, 6.3 g ai/ha or more, 6.4 g ai/ha or more, 6.5 g ai/ha or more, 6.6 g ai/ha or more, 6.7 g ai/ha or more, 6.8 g ai/ha or more, 6.9 g ai/ha or more, 7 g ai/ha or more, 7.1 g ai/ha or more, 7.2 ai/ha or more, 7.3 g ai/ha or more, 7.4 g ai/ha or more, 7.5 g ai/ha or more, 7.6 g ai/ha or more, 7.7 g ai/ha or more, 7.8 g ai/ha or more, 7.9 g ai/ha or more, 8 g ai/ha or more, 8.1 g ai/ha or more, 8.2 g ai/ha or more, 8.3 g ai/ha or more, 8.4 ai/ha or more, 8.5 g ai/ha or more, 8.6 g ai/ha or more, 8.7 g ai/ha or more, 8.8 g ai/ha or more, 8.9 g ai/ha or more, 9 g ai/ha or more, 9.1 g ai/ha or more, 9.2 g ai/ha or more, 9.3 g ai/ha or more, 9.4 g ai/ha or more, 9.5 g ai/ha or more, 9.6 g ai/ha or more, 9.7 g ai/ha or more, 9.8 g ai/ha or more, or 9.9 g ai/ha or more).

In some embodiments, the flupyrsulfuron or agriculturally acceptable salt or ester thereof is applied to vegetation or an area adjacent the vegetation or applied to soil or water to prevent the emergence or growth of vegetation in an amount of 10 g ai/ha or less (e.g., 9.9 g ai/ha or less, 9.8 g ai/ha or less, 9.7 g ai/ha or less, 9.6 g ai/ha or less, 9.5 g ai/ha or less, 9.4 g ai/ha or less, 9.3 g ai/ha or less, 9.2 g ai/ha or less, 9.1 g ai/ha or less, 9 g ai/ha or less, 8.9 g ai/ha or less, 8.8 g ai/ha or less, 8.7 g ai/ha or less, 8.6 g ai/ha or less, 8.5 g ai/ha or less, 8.4 g ai/ha or less, 8.3 g ai/ha or less, 8.2 g ai/ha or less, 8.1 g ai/ha or less, 8 g ai/ha or less, 7.9 g ai/ha or less, 7.8 g ai/ha or less, 7.7 g ai/ha or less, 7.6 g ai/ha or less, 7.5 g ai/ha or less, 7.4 g ai/ha or less, 7.3 g ai/ha or less, 7.2 g ai/ha or less, 7.1 g ai/ha or less, 7 g ai/ha or less, 6.9 g ai/ha or less, 6.8 g ai/ha or less, 6.7 g ai/ha or less, 6.6 g ai/ha or less, 6.5 g ai/ha or less, 6.4 g ai/ha or less, 6.3 g ai/ha or less, 6.2 g ai/ha or less, 6.1 g ai/ha or less, 6 g ai/ha or less, 5.9 g ai/ha or less, 5.8 g ai/ha or less, 5.7 g ai/ha or less, 5.6 g ai/ha or less, 5.5 g ai/ha or less, 5.4 g ai/ha or less, 5.3 g ai/ha or less, 5.2 g ai/ha or less, 5.1 g ai/ha or less, 5 g ai/ha or less, 4.9 g ai/ha or less, 4.8 g ai/ha or less, 4.7 g ai/ha or less, 4.6 g ai/ha or less, 4.5 g ai/ha or less, 4.4 g ai/ha or less, 4.3 g ai/ha or less, 4.2 g ai/ha or less, 4.1 g ai/ha or less, 4 g ai/ha or less, 3.9 g ai/ha or less, 3.8 g ai/ha or less, 3.7 g ai/ha or less, 3.6 g ai/ha or less, 3.5 g ai/ha or less, 3.45 g ai/ha or less, 3.4 g ai/ha or less, 3.35 g ai/ha or less, 3.3 g ai/ha or less, 3.25 g ai/ha or less, 3.2 g ai/ha or less, 3.15 g ai/ha or less, 3.1 g ai/ha or less, 3.05 g ai/ha or less, 3 g ai/ha or less, 2.95 g ai/ha or less, 2.9 g ai/ha or less, 2.85 g ai/ha or less, 2.8 g ai/ha or less, 2.75 g ai/ha or less, 2.7 g ai/ha or less, 2.65 g ai/ha or less, 2.6 g ai/ha or less, or 2.55 g ai/ha or less).

The flupyrsulfuron or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the flupyrsulfuron or agriculturally acceptable salt or ester thereof is applied to vegetation or an area adjacent the vegetation or applied to soil or water to prevent the emergence or growth of vegetation in an amount of 2.5-10 g ai/ha (e.g., 2.5-9.5 g ai/ha, 2.5-9 g ai/ha, 2.75-10 g ai/ha, 2.75-9 g ai/ha, 3-10 g ai/ha, 3.25-10 g ai/ha, 3.25-8 g ai/ha, 3.5-10 g ai/ha, 3.5-9 g ai/ha, 3.5-8 g ai/ha, 3.5-7 g ai/ha, 3.5-6 g ai/ha, or 3.5-5 g ai/ha).

Foramsulfuron

Compositions and methods of the present disclosure can include foramsulfuron or an agriculturally acceptable salt thereof. Foramsulfuron, shown below, is a sulfonylurea that provides e.g., post-emergence control of grass and broadleaf weeds in maize. Foramsulfuron, as well as methods of preparing foramsulfuron, are known in the art. Its herbicidal activity is described in *The Pesticide Manual*, Fifteenth Edition, 2009.

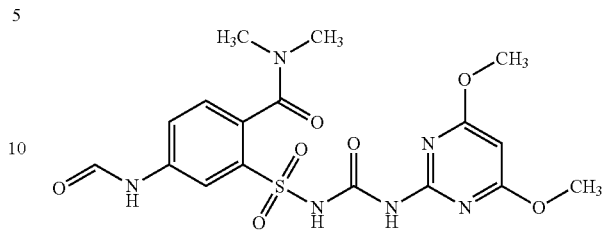

In some embodiments, foramsulfuron can be provided as an agriculturally acceptable salt of foramsulfuron.

The foramsulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the foramsulfuron or agriculturally acceptable salt thereof is applied to vegetation or an area adjacent the vegetation or applied to soil or water to prevent the emergence or growth of vegetation in an amount of 2.5 g ai/ha or more (e.g., 3 g ai/ha or more, 3.5 g ai/ha or more, 4 g ai/ha or more, 4.5 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 8.5 g ai/ha or more, 9 g a/ha or more, 9.5 g ai/ha or more, 10 g ai/ha or more, 10.5 g a/ha or more, 11 g ai/ha or more, 11.5 g ai/ha or more, 12 g ai/ha or more, 12.5 g ai/ha or more, 13 g ai/ha or more, 13.5 g ai/ha or more, 14 g ai/ha or more, 14.5 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, or 59 g ai/ha or more).

In some embodiments, the foramsulfuron or agriculturally acceptable salt thereof is applied to vegetation or an area adjacent the vegetation or applied to soil or water to prevent the emergence or growth of vegetation in an amount of 60 g ai/ha or less (e.g., 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14.5 g ai/ha or less, 14 g ai/ha or less, 13.5 g ai/ha or less, 13 g ai/ha or less, 12.5 g ai/ha or less, 12 g ai/ha or less, 11.5 g ai/ha or less, 11 g ai/ha or less, 10.5 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.5 g ai/ha or less, 4 g ai/ha or less, 3.5 g ai/ha or less, or 3 g ai/ha or less).

The foramsulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the foramsulfuron or agriculturally acceptable salt thereof is applied to vegetation or an area adjacent the vegetation or applied to soil or water to prevent the emergence or growth of vegetation in an amount of 2.5-60 g ai/ha (e.g., 2.5-59 g ai/ha, 2.5-58 g ai/ha, 2.5-57 g ai/ha, 2.5-55 g ai/ha, 5-60 g ai/ha, 5-59 g ai/ha, 5-58 g ai/ha, 5-57 g ai/ha, 5-55 g ai/ha, 7.5-60 g ai/ha, 7.5-58 g ai/ha, 7.5-55 g ai/ha, 10-60 g ai/ha, 10-58 g ai/ha, 10-55 g ai/ha, 12.5-60 g ai/ha, 12.5-55 g ai/ha, or 15-55 g ai/ha).

Halosulfuron

Compositions and methods of the present disclosure can include halosulfuron or an agriculturally acceptable salt or ester thereof. Halosulfuron-methyl, shown below, is a sulfonylurea that has demonstrated activity for the control of annual broadleaf weeds and nutsedge species, in maize, sugar cane, rice, sorghum, nuts, and turf. Halosulfuron, as well as methods of preparing halosulfuron, are known in the art. Its herbicidal activity is described in *The Pesticide Manual*, Fifteenth Edition, 2009.

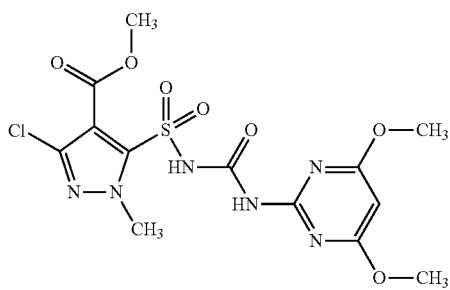 [SMILES: COC(=O)c1c(Cl)nn(C)c1S(=O)(=O)NC(=O)Nc1nc(OC)cc(OC)n1]

In some embodiments, halosulfuron can be provided as an agriculturally acceptable salt or ester of halosulfuron.

The halosulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the halosulfuron or agriculturally acceptable salt or ester thereof is applied to vegetation or an area adjacent the vegetation or applied to soil or water to prevent the emergence or growth of vegetation in an amount of 4.375 g ai/ha or more (e.g., 4.5 g ai/ha or more, 4.75 g ai/ha or more, 5 g ai/ha or more, 6 g ai/ha or more, 7 g ai/ha or more, 8 g ai/ha or more, 9 g ai/ha or more, 10 g ai/ha or more, 15 g ai/ha or more, 20 g ai/ha or more, 25 g ai/ha or more, 30 g ai/ha or more, 35 g ai/ha or more, 40 g ai/ha or more, 45 g ai/ha or more, 50 g ai/ha or more, 55 g ai/ha or more, 60 g ai/ha or more, 65 g ai/ha or more, 70 g ai/ha or more, 75 g ai/ha or more, 80 g ai/ha or more, 85 g ai/ha or more, 90 g ai/ha or more, 95 g ai/ha or more, 100 g ai/ha or more, 105 g ai/ha or more, 110 g ai/ha or more, 115 g ai/ha or more, 120 g ai/ha or more, 122 g ai/ha or more, 124 g ai/ha or more, 126 g ai/ha or more, 128 g ai/ha or more, 130 g ai/ha or more, 131 g ai/ha or more, 132 g ai/ha or more, 133 g ai/ha or more, 134 g ai/ha or more, 135 g ai/ha or more, 136 g ai/ha or more, 137 g ai/ha or more, 138 g ai/ha or more, or 139 g ai/ha or more).

In some embodiments, the halosulfuron or agriculturally acceptable ester thereof is applied to vegetation or an area adjacent the vegetation or applied to soil or water to prevent the emergence or growth of vegetation in an amount of 140 g ai/ha or less (e.g., 139 g ai/ha or less, 138 g ai/ha or less, 137 g ai/ha or less, 136 g ai/ha or less, 135 g ai/ha or less, 134 g ai/ha or less, 133 g ai/ha or less, 132 g ai/ha or less, 131 g ai/ha or less, 130 g ai/ha or less, 129 g ai/ha or less, 128 g ai/ha or less, 126 g ai/ha or less, 124 g ai/ha or less, 122 g ai/ha or less, 120 g ai/ha or less, 115 g ai/ha or less, 110 g ai/ha or less, 105 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, 35 g ai/ha or less, 30 g ai/ha or less, 25 g ai/ha or less, 20 g ai/ha or less, 15 g ai/ha or less, 10 g ai/ha or less, 9 g ai/ha or less, 8 g ai/ha or less, 7 g ai/ha or less, 6 g ai/ha or less, 5 g ai/ha or less, 4.75 g ai/ha or less, or 4.5 g ai/ha or less).

The halosulfuron or an agriculturally acceptable ester thereof can be applied to vegetation or an area adjacent the vegetation or applied to soil or water to prevent the emergence or growth of vegetation in an amount ranging from any of the minimum values described above to any of the maximum values described above. In some embodiments, the halosulfuron or agriculturally acceptable salt thereof is applied to vegetation or an area adjacent the vegetation or applied to soil or water to prevent the emergence or growth of vegetation in an amount of 4.375-140 g ai/ha (e.g., 4.375-120 g ai/ha, 4.375-100 g ai/ha, 4.5-140 g ai/ha, 4.5-120 g ai/ha, 4.5-100 g ai/ha, 5-140 g ai/ha, 5-120 g ai/ha, 5-100 g ai/ha, 10-140 g ai/ha, 10-120 g ai/ha, 10-100 g ai/ha, 25-140 g ai/ha, or 25-100 g ai/ha).

Iodosulfuron

Compositions and methods of the present disclosure can include iodosulfuron or an agriculturally acceptable salt or ester thereof. Iodosulfuron-methyl-sodium, shown below, is a sulfonylurea that provides, e.g., post-emergence control of grass and broadleaf weeds in winter, spring and durum wheat, triticale, rye and spring barley. Iodosulfuron, as well as methods of preparing iodosulfuron, are known in the art. Its herbicidal activity is described in *The Pesticide Manual*, Fifteenth Edition, 2009.

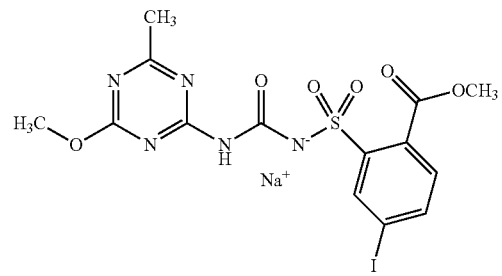 [SMILES: COC(=O)c1ccc(I)cc1S(=O)(=O)[N-]C(=O)Nc1nc(C)nc(OC)n1 ; [Na+]]

In certain embodiments, the carboxylic acid or a salt thereof, or a different ester, e.g., alkyl or aralkyl ester, with respect to the methyl ester moiety is utilized. In certain embodiments, a different salt or non-ionic form is utilized.

The iodosulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the iodosulfuron or agriculturally acceptable salt or ester thereof is applied to vegetation or an area adjacent the vegetation or applied to soil or water to prevent the emergence or growth of vegetation in an amount of 1.25 g ai/ha or more (e.g., 1.3 g ai/ha or more, 1.4 g ai/ha or more, 1.5 g ai/ha or more, 1.6 g ai/ha or more, 1.7 g ai/ha or more, 1.8 g ai/ha or more, 1.9 g ai/ha or more, 2.0 g ai/ha or more, 2.1 g ai/ha or more, 2.2 g ai/ha or more, 2.3 g ai/ha or more, 2.3 g ai/ha or more, 2.4 g ai/ha or more, 2.5 g ai/ha or more, 2.6 g ai/ha or more, 2.7 g ai/ha or more, 2.8 g ai/ha or more, 2.9 g ai/ha or more, 3.0 g ai/ha or more, 3.1 g ai/ha or more, 3.2 g ai/ha or more, 3.3 g ai/ha or more, 3.4 g ai/ha or more, 3.5 g ai/ha or more, 3.6 g ai/ha or more, 3.7 g ai/ha or more, 3.8 g ai/ha or more, 3.9 g ai/ha or more, 4 g ai/ha or more, 4.1 g ai/ha or more, 4.2 g ai/ha or more, 4.3 g ai/ha or more, 4.4 g ai/ha or more, 4.5 g ai/ha or more, 4.6 g ai/ha or more, 4.7 g ai/ha or more, 4.8 g ai/ha or more, 4.9 g ai/ha or more, 5 g ai/ha or more, 5.1 g ai/ha or more, 5.2 g ai/ha or more, 5.3 g ai/ha or more, 5.4 g ai/ha or more, 5.5 g ai/ha or more, 5.6 g ai/ha or more, 5.7 g ai/ha or more, 5.8 g ai/ha or more, 5.9 g ai/ha or more, 6 g ai/ha or more, 6.1 g ai/ha or more, 6.2 g ai/ha or more, 6.3 g ai/ha or more, 6.4 g ai/ha or more, 6.5 g ai/ha or more, 6.6 g ai/ha or more, 6.7 g ai/ha or more, 6.8 g ai/ha or more, 6.9 g ai/ha or more, 7 g ai/ha or more, 7.1 g ai/ha or more, 7.2 ai/ha or more, 7.3 g ai/ha or more, 7.4 g ai/ha or more, 7.5 g ai/ha or more, 7.6 g ai/ha or more, 7.7 g ai/ha or more, 7.8 g ai/ha or more, 7.9 g ai/ha or more, 8 g ai/ha or more, 8.1 g ai/ha or more, 8.2 g ai/ha or more, 8.3 g ai/ha or more, 8.4 ai/ha or more, 8.5 g ai/ha or more, 8.6 g ai/ha or more, 8.7 g ai/ha or more, 8.8 g ai/ha or more, 8.9 g ai/ha or more, 9 g ai/ha or more, 9.1 g ai/ha or more, 9.2 g ai/ha or more, 9.3 g ai/ha or more, 9.4 g ai/ha or more, 9.5 g ai/ha or more, 9.6 g ai/ha or more, 9.7 g ai/ha or more, 9.8 g ai/ha or more, or 9.9 g ai/ha or more).

In some embodiments, the iodosulfuron or agriculturally acceptable salt or ester thereof is applied to vegetation or an area adjacent the vegetation or applied to soil or water to prevent the emergence or growth of vegetation in an amount of 10 g ai/ha or less (e.g., 9.9 g ai/ha or less, 9.8 g ai/ha or less, 9.7 g ai/ha or less, 9.6 g ai/ha or less, 9.5 g ai/ha or less, 9.4 g ai/ha or less, 9.3 g ai/ha or less, 9.2 g ai/ha or less, 9.1 g ai/ha or less, 9 g ai/ha or less, 8.9 g ai/ha or less, 8.8 g ai/ha or less, 8.7 g ai/ha or less, 8.6 g ai/ha or less, 8.5 g ai/ha or less, 8.4 g ai/ha or less, 8.3 g ai/ha or less, 8.2 g ai/ha or less, 8.1 g ai/ha or less, 8 g ai/ha or less, 7.9 g ai/ha or less, 7.8 g ai % ha or less, 7.7 g ai/ha or less, 7.6 g ai/ha or less, 7.5 g ai/ha or less, 7.4 g ai/ha or less, 7.3 g ai/ha or less, 7.2 g ai/ha or less, 7.1 g ai/ha or less, 7 g ai/ha or less, 6.9 g ai/ha or less, 6.8 g ai/ha or less, 6.7 g ai/ha or less, 6.6 g ai/ha or less, 6.5 g ai/ha or less, 6.4 g ai/ha or less, 6.3 g ai/ha or less, 6.2 g ai/ha or less, 6.1 g ai/ha or less, 6 g ai/ha or less, 5.9 g ai/ha or less, 5.8 g ai/ha or less, 5.7 g ai/ha or less, 5.6 g ai/ha or less, 5.5 g ai/ha or less, 5.4 g ai/ha or less, 5.3 g ai/ha or less, 5.2 g ai ha or less, 5.1 g ai/ha or less, 5 g ai/ha or less, 4.9 g ai/ha or less, 4.8 g ai/ha or less, 4.7 g ai/ha or less, 4.6 g ai/ha or less, 4.5 g ai/ha or less, 4.4 g ai/ha or less, 4.3 g ai/ha or less, 4.2 g ai/ha or less, 4.1 g ai/ha or less, 4 g ai/ha or less, 3.9 g ai/ha or less, 3.8 g ai/ha or less, 3.7 g ai/ha or less, 3.6 g ai/ha or less, 3.5 g ai/ha or less, 3.4 g ai/ha or less, 3.3 g ai/ha or less, 3.2 g ai/ha or less, 3.1 g ai/ha or less, 3 g ai/ha or less, 2.9 g ai/ha or less, 2.8 g ai/ha or less, 2.7 g ai/ha or less, 2.6 g ai/ha or less, 2.5 g ai/ha or less, 2.4 g ai/ha or less, 2.3 g ai/ha or less, 2.2 g ai/ha or less, 2.1 g ai/ha or less, 2.0 g ai/ha or less, 1.9 g ai/ha or less, 1.8 g ai/ha or less, 1.7 g ai/ha or less, 1.6 g ai/ha or less, 1.5 g ai/ha or less, 1.4 g ai/ha or less, or 1.3 g ai/ha or less).

The iodosulfuron or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the iodosulfuron or agriculturally acceptable salt or ester thereof is applied to vegetation or an area adjacent the vegetation or applied to soil or water to prevent the emergence or growth of vegetation in an amount of 1.25-10 g ai/ha (e.g., 1.25-9 g ai/ha, 1.25-8 g ai/ha, 1.25-7.5 g ai/ha, 1.5-10 g ai/ha, 1.5-9 g ai/ha, 1.5-8 g ai/ha, 1.5-7.5 g ai/ha, 2-10 g ai/ha, 2-9 g ai/ha, 2-8 g ai/ha, 2-7.5 g ai/ha, 2.5-10 g ai/ha, or 2.5-9 g ai/ha).

Mesosulfuron

Compositions and methods of the present disclosure can include mesosulfuron or an agriculturally acceptable salt or ester thereof. Mesosulfuron-methyl, shown below, is a sulfonylurea that provides, e.g., early to mid post-emergence control of grass and some broadleaf weeds in winter, spring, and durum wheat, triticale, and rye. Mesosulfuron, as well as methods of preparing mesosulfuron, are known in the art. Its herbicidal activity is described in *The Pesticide Manual*, Fifteenth Edition, 2009.

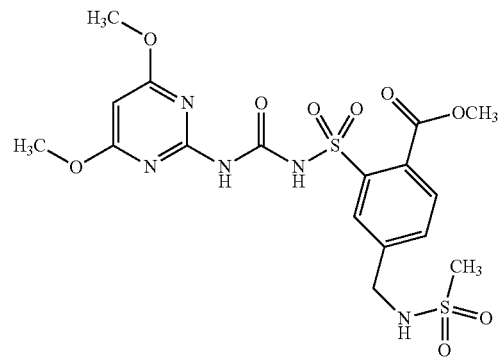 [SMILES: COC(=O)c1ccc(CNS(C)(=O)=O)cc1S(=O)(=O)NC(=O)Nc1nc(OC)cc(OC)n1]

In certain embodiments, the carboxylic acid or a salt thereof, or a different ester, e.g., alkyl or aralkyl ester, with respect to the methyl ester moiety is utilized.

The mesosulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the mesosulfuron or agriculturally acceptable salt or ester thereof is applied to vegetation or an area adjacent the vegetation or applied to soil or water to prevent the emergence or growth of vegetation in an amount of 1.5 g ai/ha or more (e.g., 1.55 g ai/ha or more, 1.6 g ai/ha or more, 1.65 g ai/ha or more, 1.7 g ai/ha or more, 1.75 g ai/ha or more, 1.8 g ai/ha or more, 1.85 g ai/ha or more, 1.9 g ai/ha or more, 1.95 g ai/ha or more, 2 g ai/ha or more, 2.25 g ai/ha or more, 2.5 g ai/ha or more, 2.75 g ai/ha or more, 3 g ai/ha or more, 3.25 g ai/ha or more, 3.5 g ai/ha or more, 3.75 g ai/ha or more, 4 g ai/ha or more, 4.25 g ai/ha or more, 4.5 g ai/ha or more, 4.75 g ai/ha or more, 5 g ai/ha or more, 6 g ai/ha or more, 7 g ai/ha or more, 8 g ai/ha or more, 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, or 44 g ai/ha or more).

In some embodiments, the mesosulfuron or agriculturally acceptable salt or ester thereof is applied to vegetation or an area adjacent the vegetation or applied to soil or water to prevent the emergence or growth of vegetation in an amount of 45 g ai/ha or less (e.g., 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7 g ai/ha or less, 6 g ai/ha or less, 5 g ai/ha or less, 4.75 g ai/ha or less, 4.5 g ai/ha or less, 4.25 g ai/ha or less, 4 g ai/ha or less, 3.75 g ai/ha or less, 3.5 g ai/ha or less, 3.25 g ai/ha or less, 3 g ai/ha or less, 2.75 g ai/ha or less, 2.5 g ai/ha or less, 2.25 g ai/ha or less, 2 g ai/ha or less, 1.95 g ai/ha or less, 1.9 g ai/ha or less, 1.85 g ai/ha or less, 1.8 g ai/ha or less, 1.75 g ai/ha or less, 1.7 g ai/ha or less, 1.65 g ai/ha or less, 1.6 g ai/ha or less, or 1.55 g ai/ha or less).

The mesosulfuron or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the mesosulfuron or agriculturally acceptable salt or ester thereof is applied to vegetation or an area adjacent the vegetation or applied to soil or water to prevent the emergence or growth of vegetation in an amount of 1.5-45 g ai/ha (e.g., 1.5-42 g ai/ha, 1.5-40 g ai/ha, 1.75-45 g ai/ha, 1.75-40 g ai/ha, 2-45 g ai/ha, 2.25-45 g ai/ha, 2.25-40 g ai/ha, 2.5-45 g ai/ha, 2.5-40 g ai/ha, 2.5-35 g ai/ha, 2.75-45 g ai/ha, 2.75-40 g ai/ha, or 4-40 g ai/ha).

Metsulfuron

Compositions and methods of the present disclosure can include metsulfuron or an agriculturally acceptable salt or ester thereof. Metsulfuron-methyl, shown below, is a sulfonylurea that controls, e.g., grass and broadleaf weeds in wheat, barley, rice, oats, and triticale. Metsulfuron, as well as methods of preparing metsulfuron, are known in the art. Its herbicidal activity is described in *The Pesticide Manual*, Fifteenth Edition, 2009.

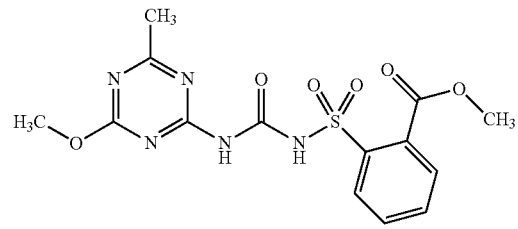

In certain embodiments, the carboxylic acid or a salt thereof, or a different ester, e.g., alkyl or aralkyl ester, with respect to the methyl ester moiety is utilized.

The metsulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the metsulfuron or agriculturally acceptable salt thereof is applied to vegetation or an area adjacent the vegetation or applied to soil or water to prevent the emergence or growth of vegetation in an amount of 1 g ai/ha or more (e.g., 1.25 g ai/ha or more, 1.3 g ai/ha or more, 1.4 g ai/ha or more, 1.5 g ai/ha or more, 1.6 g ai/ha or more, 1.7 g ai/ha or more, 1.8 g ai/ha or more, 1.9 g ai/ha or more, 2 g ai/ha or more, 2.1 g ai/ha or more, 2.2 g ai/ha or more, 2.3 g ai/ha or more, 2.3 g ai/ha or more, 2.4 g ai/ha or more, 2.5 g ai/ha or more, 2.6 g ai/ha or more, 2.7 g ai/ha or more, 2.8 g ai/ha or more, 2.9 g ai/ha or more, 3 g ai/ha or more, 3.1 g ai/ha or more, 3.2 g ai/ha or more, 3.3 g ai/ha or more, 3.4 g ai/ha or more, 3.5 g ai/ha or more, 3.6 g ai/ha or more, 3.7 g ai/ha or more, 3.8 g ai/ha or more, 3.9 g ai/ha or more, 4 g ai/ha or more, 4.1 g ai/ha or more, 4.2 g ai/ha or more, 4.3 g ai/ha or more, 4.4 g ai/ha or more, 4.5 g ai/ha or more, 4.6 g ai/ha or more, 4.7 g ai/ha or more, 4.8 g ai/ha or more, 4.9 g ai/ha or more, 5 g ai/ha or more, 5.1 g ai/ha or more, 5.2 g ai/ha or more, 5.3 g ai/ha or more, 5.4 g ai/ha or more, 5.5 g ai/ha or more, 5.6 g ai/ha or more, 5.7 g ai/ha or more, 5.8 g ai/ha or more, 5.9 g ai/ha or more, 6 g ai/ha or more, 6.1 g ai/ha or more, 6.2 g ai/ha or more, 6.3 g ai/ha or more, 6.4 g ai/ha or more, 6.5 g ai/ha or more, 6.6 g ai/ha or more, 6.7 g ai/ha or more, 6.8 g ai/ha or more, 6.9 g ai/ha or more, 7 g ai/ha or more, 7.1 g ai/ha or more, 7.2 g ai/ha or more, 7.3 g ai/ha or more, 7.4 g ai/ha or more, 7.5 g ai/ha or more, 7.6 g ai/ha or more, 7.7 g ai/ha or more, 7.8 g ai/ha or more, 7.9 g ai/ha or more, 8 g ai/ha or more, 8.1 g ai/ha or more, 8.2 g ai/ha or more, 8.3 g ai/ha or more, 8.4 g ai/ha or more, 8.5 g ai/ha or more, 8.6 g ai/ha or more, 8.7 g ai/ha or more, 8.8 g ai/ha or more, 8.9 g ai/ha or more, 9 g ai/ha or more, 9.1 g ai/ha or more, 9.2 g ai/ha or more, 9.3 g ai/ha or more, 9.4 g ai/ha or more, 9.5 g ai/ha or more, 9.6 g ai/ha or more, 9.7 g ai/ha or more, 9.8 g ai/ha or more, 9.9 g ai/ha or more, 10 g ai/ha or more, 10.1 g ai/ha or more, 10.2 g ai/ha or more, 10.3 g ai/ha or more, 10.4 g ai/ha or more, 10.5 g a/ha or more, 10.6 g ai/ha or more, 10.7 g ai/ha or more, 10.8 g ai/ha or more, 10.9 g ai/ha or more, 11 g ai/ha or more, 11.1 g ai/ha or more, 11.2 g ai/ha or more, 11.3 g ai/ha or more, 11.4 g ai/ha or more, 11.5 g ai/ha or more, 11.6 g ai/ha or more, 11.7 g ai/ha or more, 11.8 g ai/ha or more, or 11.9 g ai/ha or more).

In some embodiments, the metsulfuron or agriculturally acceptable salt or ester thereof is applied to vegetation or an area adjacent the vegetation or applied to soil or water to prevent the emergence or growth of vegetation in an amount of 12 g ai/ha or less (e.g., 11.9 g ai/ha or less, 11.8 g ai/ha or less, 11.7 g ai/ha or less, 11.6 g ai/ha or less, 11.5 g ai/ha or less, 1.4 g ai/ha or less, 11.3 g ai/ha or less, 11.2 g ai/ha or less, 11.1 g ai/ha or less, 11 g ai/ha or less, 10.9 g ai/ha or less, 10.8 g ai/ha or less, 10.7 g ai/ha or less, 10.6 g ai/ha or less, 10.5 g ai/ha or less, 10.4 g ai/ha or less, 10.3 g ai/ha or less, 10.2 g ai/ha or less, 10.1 g ai/ha or less, 10 g ai/ha or less, 9.9 g ai/ha or less, 9.8 g ai ha or less, 9.7 g ai/ha or less, 9.6 g ai/ha or less, 9.5 g ai/ha or less, 9.4 g ai/ha or less, 9.3 g ai/ha or less, 9.2 g ai/ha or less, 9.1 g ai/ha or less, 9 g ai/ha or less, 8.9 g ai/ha or less, 8.8 g ai/ha or less, 8.7 g ai/ha or less, 8.6 g ai/ha or less, 8.5 g ai/ha or less, 8.4 g ai/ha or less, 8.3 g ai/ha or less, 8.2 g ai/ha or less, 8.1 g ai/ha or less, 8 g ai/ha or less, 7.9 g ai/ha or less, 7.8 g ai/ha or less, 7.7 g ai/ha or less, 7.6 g ai ha or less, 7.5 g ai/ha or less, 7.4 g ai/ha or less, 7.3 g ai/ha or less, 7.2 g ai/ha or less, 7.1 g ai/ha or less, 7 g ai/ha or less, 6.9 g ai/ha or less, 6.8 g ai/ha or less, 6.7 g ai/ha or less, 6.6 g ai/ha or less, 6.5 g ai/ha or less, 6.4 g ai/ha or less, 6.3 g ai/ha or less, 6.2 g ai ha or less, 6.1 g ai/ha or less, 6 g ai/ha or less, 5.9 g ai/ha or less, 5.8 g ai/ha or less, 5.7 g ai/ha or less, 5.6 g ai/ha or less, 5.5 g ai/ha or less, 5.4 g ai/ha or less, 5.3 g ai/ha or less, 5.2 g ai/ha or less, 5.1 g ai/ha or less, 5 g ai/ha or less, 4.9 g ai/ha or less, 4.8 g ai/ha or less, 4.7 g ai/ha or less, 4.6 g ai/ha or less, 4.5 g ai/ha or less, 4.4 g ai/ha or less, 4.3 g ai/ha or less, 4.2 g ai/ha or less, 4.1 g ai ha or less, 4 g ai/ha or less, 3.9 g ai/ha or less, 3.8 g ai/ha or less, 3.7 g ai/ha or less, 3.6 g ai/ha or less, 3.5 g ai/ha or less, 3.4 g ai/ha or less, 3.3 g ai/ha or less, 3.2 g ai/ha or less, 3.1 g ai/ha or less, 3 g ai/ha or less, 2.9 g ai/ha or less, 2.8 g ai/ha or less, 2.7 g ai/ha or less, 2.6 g ai/ha or less, 2.5 g ai/ha or less, 2.4 g ai/ha or less, 2.3 g ai/ha or less, 2.2 g ai/ha or less, 2.1 g ai/ha or less, 2 g ai/ha or less, 1.9 g ai/ha or less, 1.8 g ai/ha, 1.7 g ai/ha or less, 1.6 g ai/ha or less, 1.5 g ai/ha or less, 1.4 g ai/ha or less, 1.3 g ai/ha or less, or 1.25 g ai/ha or less).

The metsulfuron or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the metsulfuron or agriculturally acceptable salt or ester thereof is applied to vegetation or an area adjacent the vegetation or applied to soil or water to prevent the emergence or growth of vegetation in an amount of 1-12 g ai/ha (e.g., 1-11 g ai/ha, 1-10 g ai/ha, 1-8 g ai/ha, 1.25-12 g ai/ha, 1.25-10 g ai/ha, 1.25-8 g ai/ha, 1.5-12 g ai/ha, 1.5-10 g ai/ha, 2-12 g ai/ha, 2-10 g ai/ha, 2-8 g ai/ha, 2-7.5 g ai/ha, 2.5-12 g ai/ha, or 2.5-10 g ai/ha).

Nicosulfuron

Compositions and methods of the present disclosure can include nicosulfuron or an agriculturally acceptable salt thereof. Nicosulfuron, shown below, is a sulfonylurea that provides, e.g., selective post-emergence control in maize of annual grass weeds, including *Setaria*, *Echinochloa*, *Digitaria*, *Panicum*, *Lolium* and *Avena* spp., broadleaf weeds, including *Amaranthus* spp. and *Cruciferae*, and perennials such as *Sorghum halepense* and *Agropyron repens*. Nicosulfuron, as well as methods of preparing nicosulfuron, are known in the art. Its herbicidal activity is described in *The Pesticide Manual*, Fifteenth Edition, 2009.

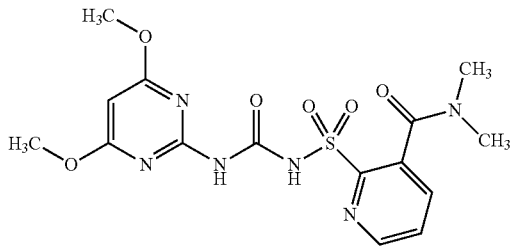

In some embodiments, nicosulfuron can be provided as an agriculturally acceptable salt of nicosulfuron.

The nicosulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the nicosulfuron or agriculturally acceptable salt thereof is applied to vegetation or an area adjacent the vegetation or applied to soil or water to prevent the emergence or growth of vegetation in an amount of 8.75 g ai/ha or more (e.g., 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai/ha or more, or 69 g ai/ha or more).

In some embodiments, the nicosulfuron or agriculturally acceptable salt thereof is applied to vegetation or an area adjacent the vegetation or applied to soil or water to prevent the emergence or growth of vegetation in an amount of 70 g ai/ha or less (e.g., 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, or 9 g ai/ha or less).

The nicosulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the nicosulfuron or agriculturally acceptable salt thereof is applied to vegetation or an area adjacent the vegetation or applied to soil or water to prevent the emergence or growth of vegetation in an amount of 8.75-70 g ai/ha (e.g., 8.75-68 g ai/ha, 8.75-65 g ai/ha, 9-60 g ai/ha, 10-70 g ai/ha, 10-68 g ai/ha, 10-65 g ai/ha, 10-60 g ai/ha, 11-70 g ai/ha, 11-68 g ai/ha, 11-65 g ai/ha, 11-60 g ai/ha, 20-60 g ai/ha, or 20-50 g ai/ha).

Orthosulfamuron

Compositions and methods of the present disclosure can include orthosulfamuron or an agriculturally acceptable salt thereof. Orthosulfamuron, shown below, is a sulfonylurea that provides, e.g., early post-emergence control of annual and perennial broadleaf weeds and sedges in rice, cereals, pastures, and sugar cane. Orthosulfamuron, as well as methods of preparing orthosulfamuron, are known in the art. Its herbicidal activity is described, for example, in *The Pesticide Manual*, Fifteenth Edition, 2009.

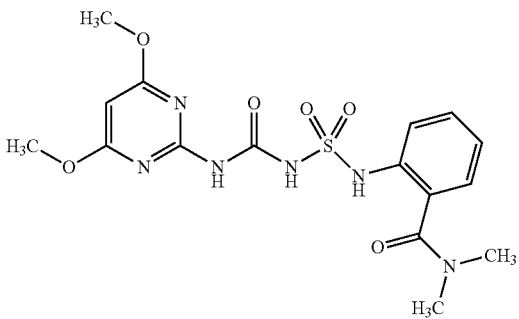

In some embodiments, orthosulfamuron can be provided as an agriculturally acceptable salt of orthosulfamuron.

The orthosulfamuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the orthosulfamuron or agriculturally acceptable salt thereof is applied to vegetation or an area adjacent the vegetation or applied to soil or water to prevent the emergence or growth of vegetation in an amount of 7.5 g ai ha or more (e.g., 7.75 g ai/ha or more, 8 g ai/ha or more, 8.25 g ai/ha or more, 8.5 g ai/ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai/ha or more, 69 g ai/ha or more, 70 g ai/ha or more, 71 g ai/ha or more, 72 g ai/ha or more, 73 g ai/ha or more, or 74 g ai/ha or more).

In some embodiments, the orthosulfamuron or agriculturally acceptable salt thereof is applied to vegetation or an area adjacent the vegetation or applied to soil or water to prevent the emergence or growth of vegetation in an amount of 75 g ai/ha or less (e.g., 74 g ai/ha or less, 73 g ai/ha or less, 72 g ai/ha or less, 71 g ai/ha or less, 70 g ai/ha or less, 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8.25 g ai/ha or less, 8 g ai/ha or less, or 7.75 g ai/ha or less).

The orthosulfamuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the orthosulfamuron or agriculturally acceptable salt thereof is applied to vegetation or an area adjacent the vegetation or applied to soil or water to prevent the emergence or growth of vegetation in an amount of 7.5-75 g ai/ha (e.g., 7.5-72 g ai/ha, 7.5-70 g ai/ha, 7.75-65 g ai/ha, 9-75 g ai/ha, 9-72 g ai/ha, 9-70 g ai/ha, 9-65 g ai/ha, 10-75 g ai/ha, 10-72 g ai/ha, 10-65 g ai/ha, 10-60 g ai/ha, 20-70 g ai/ha, or 20-50 g ai/ha).

Sulfosulfuron

Compositions and methods of the present disclosure can include sulfosulfuron or an agriculturally acceptable salt thereof. Sulfosulfuron, shown below, is a sulfonylurea that provides, e.g., control of annual broadleaf weeds and grass weeds in cereals. Sulfosulfuron, as well as methods of preparing sulfosulfuron, are known in the art. Its herbicidal activity is described in *The Pesticide Manual*, Fifteenth Edition, 2009.

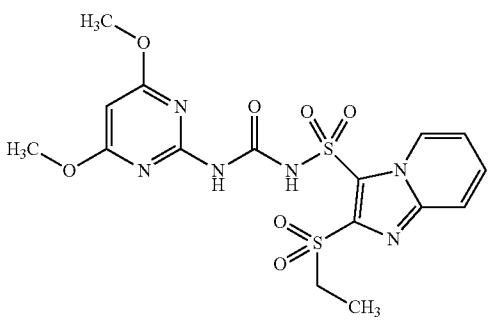 [SMILES: CCS(=O)(=O)c1nc2ccccn2c1S(=O)(=O)NC(=O)Nc1nc(OC)cc(OC)n1]

In some embodiments, sulfosulfuron can be provided as an agriculturally acceptable salt of sulfosulfuron.

The sulfosulfuron or agriculturally acceptable salt thereof can be applied to vegetation or an area adjacent the vegetation or applied to soil or water to prevent the emergence or growth of vegetation in an amount sufficient to induce a herbicidal effect. In some embodiments, the sulfosulfuron or agriculturally acceptable salt thereof is applied to vegetation or an area adjacent the vegetation or applied to soil or water to prevent the emergence or growth of vegetation in an amount of 4.375 g ai/ha or more (e.g., 4.5 g ai/ha or more, 4.75 g ai/ha or more, 5 g ai/ha or more, 5.5 g ai/ha or more, 6 g ai/ha or more, 6.5 g ai/ha or more, 7 g ai/ha or more, 7.5 g ai/ha or more, 8 g ai/ha or more, 9 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 26 g ai/ha or more, 27 g ai/ha or more, 28 g ai/ha or more, 29 g ai/ha or more, 30 g ai/ha or more, 31 g ai/ha or more, 32 g ai/ha or more, 33 g ai/ha or more, 34 g ai/ha or more, 35 g ai/ha or more, 36 g ai/ha or more, 37 g ai/ha or more, 38 g ai/ha or more, 39 g ai/ha or more, 40 g ai/ha or more, 41 g ai/ha or more, 42 g ai/ha or more, 43 g ai/ha or more, 44 g ai/ha or more, 45 g ai/ha or more, 46 g ai/ha or more, 47 g ai/ha or more, 48 g ai/ha or more, 49 g ai/ha or more, 50 g ai/ha or more, 51 g ai/ha or more, 52 g ai/ha or more, 53 g ai/ha or more, 54 g ai/ha or more, 55 g ai/ha or more, 56 g ai/ha or more, 57 g ai/ha or more, 58 g ai/ha or more, 59 g ai/ha or more, 60 g ai/ha or more, 61 g ai/ha or more, 62 g ai/ha or more, 63 g ai/ha or more, 64 g ai/ha or more, 65 g ai/ha or more, 66 g ai/ha or more, 67 g ai/ha or more, 68 g ai/ha or more, 69 g ai/ha or more, 70 g ai/ha or more, 71 g ai/ha or more, 72 g ai/ha or more, 73 g ai/ha or more, or 74 g ai/ha or more).

In some embodiments, the sulfosulfuron or agriculturally acceptable salt thereof is applied to vegetation or an area adjacent the vegetation or applied to soil or water to prevent the emergence or growth of vegetation in an amount of 75 g ai/ha or less (e.g., 74 g ai/ha or less, 73 g ai/ha or less, 72 g ai/ha or less, 71 g ai/ha or less, 70 g ai/ha or less, 69 g ai/ha or less, 68 g ai/ha or less, 67 g ai/ha or less, 66 g ai/ha or less, 65 g ai/ha or less, 64 g ai/ha or less, 63 g ai/ha or less, 62 g ai/ha or less, 61 g ai/ha or less, 60 g ai/ha or less, 59 g ai/ha or less, 58 g ai/ha or less, 57 g ai/ha or less, 56 g ai/ha or less, 55 g ai/ha or less, 54 g ai/ha or less, 53 g ai/ha or less, 52 g ai/ha or less, 51 g ai/ha or less, 50 g ai/ha or less, 49 g ai/ha or less, 48 g ai/ha or less, 47 g ai/ha or less, 46 g ai/ha or less, 45 g ai/ha or less, 44 g ai/ha or less, 43 g ai/ha or less, 42 g ai/ha or less, 41 g ai/ha or less, 40 g ai/ha or less, 39 g ai/ha or less, 38 g ai/ha or less, 37 g ai/ha or less, 36 g ai/ha or less, 35 g ai/ha or less, 34 g ai/ha or less, 33 g ai/ha or less, 32 g ai/ha or less, 31 g ai/ha or less, 30 g ai/ha or less, 29 g ai/ha or less, 28 g ai/ha or less, 27 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9 g ai/ha or less, 8 g ai/ha or less, 7.5 g ai/ha or less, 7 g ai/ha or less, 6.5 g ai/ha or less, 6 g ai/ha or less, 5.5 g ai/ha or less, 5 g ai/ha or less, 4.75 g ai/ha or less, or 4.5 g ai/ha or less).

The sulfosulfuron or an agriculturally acceptable salt thereof can be applied to vegetation or an area adjacent the vegetation or applied to soil or water to prevent the emergence or growth of vegetation in an amount ranging from any of the minimum values described above to any of the maximum values described above. In some embodiments, the sulfosulfuron or agriculturally acceptable salt thereof is applied to vegetation or an area adjacent the vegetation or applied to soil or water to prevent the emergence or growth of vegetation in an amount of 4.375-75 g ai/ha (e.g., 4.375-70 g ai/ha, 4.375-60 g ai/ha, 4.5-75 g ai/ha, 4.5-70 g ai/ha, 4.5-60 g ai/ha, 5-75 g ai/ha, 5-70 g ai/ha, 5-60 g ai/ha, 10-75 g ai/ha, 10-70 g ai/ha, 10-60 g ai/ha, 25-75 g ai/ha, or 25-70 g ai/ha).

Thifensulfuron

Compositions and methods of the present disclosure can include thifensulfuron or an agriculturally acceptable salt or ester thereof. Thifensulfuron-methyl, shown below, is a sulfonylurea that provides, e.g., control of annual weeds in cereals, maize, and pasture. Thifensulfuron, as well as methods of preparing thifensulfuron, are known in the art. Its herbicidal activity is described in *The Pesticide Manual*, Fifteenth Edition, 2009.

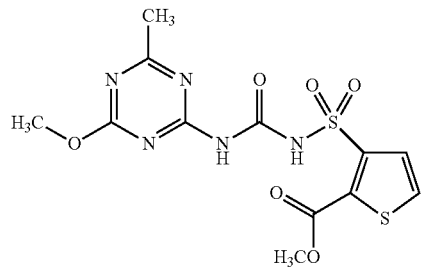 [SMILES: COC(=O)c1sccc1S(=O)(=O)NC(=O)Nc1nc(C)nc(OC)n1]

In certain embodiments, the carboxylic acid or a salt thereof, or a different ester, e.g., alkyl or aralkyl ester, with respect to the methyl ester moiety is utilized.

The thifensulfuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the thifensulfuron or agriculturally acceptable salt or ester thereof is applied to vegetation or an area adjacent the vegetation or applied to soil or water to prevent the emergence or growth of vegetation in an amount of 4.4 g ai/ha or more (e.g., 4.5 g ai/ha or more, 4.6 g ai/ha or more, 4.7 g ai/ha or more, 4.8 g ai/ha or more, 4.9 g ai/ha or more, 5 g ai/ha or more, 5.1 g ai/ha or more, 5.2 g ai/ha or more, 5.3 g ai/ha or more, 5.4 g ai/ha or more, 5.5 g ai/ha or more, 5.6 g ai/ha or more, 5.7 g ai/ha or more, 5.8 g ai/ha or more, 5.9 g ai/ha or more, 6 g ai/ha or more, 6.1 g ai/ha or more, 6.2 g ai/ha or more, 6.3 g ai/ha or more, 6.4 g ai/ha or more, 6.5 g ai/ha or more, 6.6 g ai/ha or more, 6.7 g ai/ha or more, 6.8 g ai/ha or more, 6.9 g ai/ha or more, 7 g ai/ha or more, 7.1 g ai/ha or more, 7.2 g ai/ha or more, 7.3 g ai/ha or more, 7.4 g ai/ha or more, 7.5 g ai/ha or more, 7.6 g ai/ha or more, 7.7 g ai/ha or more, 7.8 g ai/ha or more, 7.9 g ai/ha or more, 8 g ai/ha or more, 8.2 g ai/ha or more, 8.4 g ai/ha or more, 8.6 g ai/ha or more, 8.8 g ai/ha or more, 9 g ai/ha or more, 9.2 g ai/ha or more, 9.4 g ai/ha or more, 9.6 g ai/ha or more, 9.8 g ai/ha or more, 10 g ai/ha or more, 10.5 g ai/ha or more, 11 g ai/ha or more, 11.5 g ai/ha or more, 12 g ai/ha or more, 12.5 g ai/ha or more, 13 g ai/ha or more, 13.5 g ai/ha or more, 14 g ai/ha or more, 14.5 g ai/ha or more, 15 g ai/ha or more, 15.5 g ai/ha or more, 16 g ai/ha or more, 16.2 g ai/ha or more, 16.4 g ai/ha or more, 16.6 g ai/ha or more, 16.8 g ai/ha or more, 17 g ai/ha or more, 17.1 g ai/ha or more, 17.2 g ai/ha or more, 17.3 g ai/ha or more, or 17.4 g ai/ha or more).

In some embodiments, the thifensulfuron or agriculturally acceptable salt or ester thereof is applied to vegetation or an area adjacent the vegetation or applied to soil or water to prevent the emergence or growth of vegetation in an amount of 17.5 g ai/ha or less (e.g., 17.4 g ai/ha or less, 17.3 g ai/ha or less, 17.2 g ai/ha or less, 17.1 g ai/ha or less, 17 g ai/ha or less, 16.8 g ai/ha or less, 16.6 g ai/ha or less, 16.4 g ai/ha or less, 16.2 g ai/ha or less, 16 g ai/ha or less, 15.5 g ai/ha or less, 15 g ai/ha or less, 14.5 g ai/ha or less, 14 g ai/ha or less, 13.5 g ai/ha or less, 13 g ai/ha or less, 12.5 g ai/ha or less, 12 g ai/ha or less, 11.5 g ai/ha or less, 11 g ai/ha or less, 10.5 g ai/ha or less, 10 g ai/ha or less, 9.8 g ai/ha or less, 9.6 g ai/ha or less, 9.4 g ai/ha or less, 9.2 g ai/ha or less, 9 g ai/ha or less, 8.8 g ai/ha or less, 8.6 g ai/ha or less, 8.4 g ai/ha or less, 8.2 g ai/ha or less, 8 g ai/ha or less, 7.9 g ai/ha or less, 7.8 g ai/ha or less, 7.7 g ai/ha or less, 7.6 g ai/ha or less, 7.5 g ai/ha or less, 7.4 g ai/ha or less, 7.3 g ai/ha or less, 7.2 g ai/ha or less, 7.1 g ai/ha or less, 7 g ai/ha or less, 6.9 g ai/ha or less, 6.8 g ai/ha or less, 6.7 g ai/ha or less, 6.6 g ai/ha or less, 6.5 g ai/ha or less, 6.4 g ai/ha or less, 6.3 g ai/ha or less, 6.2 g ai/ha or less, 6.1 g ai/ha or less, 6 g ai/ha or less, 5.9 g ai/ha or less, 5.8 g ai ha or less, 5.7 g ai/ha or less, 5.6 g ai/ha or less, 5.5 g ai/ha or less, 5.4 g ai/ha or less, 5.3 g ai/ha or less, 5.2 g ai/ha or less, 5.1 g ai/ha or less, 5 g ai/ha or less, 4.9 g ai/ha or less, 4.8 g ai/ha or less, 4.7 g ai/ha or less, 4.6 g ai/ha or less, or 4.5 g ai/ha or less).

The thifensulfuron or agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the thifensulfuron or agriculturally acceptable salt or ester thereof is applied to vegetation or an area adjacent the vegetation or applied to soil or water to prevent the emergence or growth of vegetation in an amount of 4.4-17.5 g ai/ha (e.g., 4.4-16 g ai/ha, 4.4-15 g ai/ha, 4.8-17.5 g ai/ha, 4.8-17.5 g ai/ha, 5-17.5 g ai/ha, 5-16 g ai/ha, 5-15 g ai/ha, 6-17.5 g ai/ha, 6-16 g ai/ha, 6-15 g ai/ha, 7.5-17.5 g ai/ha, 7.5-16 g ai/ha, or 7.5-15 g ai/ha).

Tribenuron

Compositions and methods of the present disclosure can include tribenuron or an agriculturally acceptable salt thereof. Tribenuron-methyl, shown below, is a sulfonylurea that provides e.g., post-emergence control of broadleaf weeds in cereal crops, including wheat, barley, oats, rye and triticale. Tribenuron, as well as methods of preparing tribenuron, are known in the art. Its herbicidal activity is described in *The Pesticide Manual*, Fifteenth Edition, 2009.

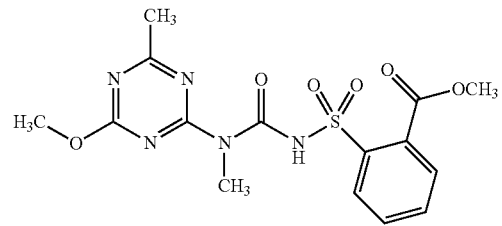 [SMILES: COC(=O)c1ccccc1S(=O)(=O)NC(=O)N(C)c1nc(C)nc(OC)n1]

In some embodiments, tribenuron can be provided as an agriculturally acceptable salt or ester of tribenuron.

The tribenuron or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the tribenuron or agriculturally acceptable salt or ester thereof is applied to vegetation or an area adjacent the vegetation or applied to soil or water to prevent the emergence or growth of vegetation in an amount of 3.75 g ai/ha or more (e.g., 4 g ai/ha or more, 4.25 g ai/ha or more, 4.5 g ai/ha or more, 4.75 g ai/ha or more, 5 g ai/ha or more, 5.25 g ai/ha or more, 5.5 g ai/ha or more, 5.75 g ai/ha or more, 6 g ai/ha or more, 6.5 g ai/ha or more, 7 g ai/ha or more, 7.5 g ai/ha or more, 8 g ai/ha or more, 8.5 g ai ha or more, 9 g ai/ha or more, 9.5 g ai/ha or more, 10 g ai/ha or more, 11 g ai/ha or more, 12 g ai/ha or more, 13 g ai/ha or more, 14 g ai/ha or more, 15 g ai/ha or more, 16 g ai/ha or more, 17 g ai/ha or more, 18 g ai/ha or more, 19 g ai/ha or more, 20 g ai/ha or more, 21 g ai/ha or more, 22 g ai/ha or more, 23 g ai/ha or more, 24 g ai/ha or more, 25 g ai/ha or more, 25.5 g ai/ha or more, 26 g ai/ha or more, 26.5 g ai/ha or more, 27 g ai/ha or more, 27.5 g ai/ha or more, 28 g ai/ha or more, 28.5 g ai/ha or more, 29 g ai/ha or more, 29.25 g ai/ha or more, 29.5 g ai/ha or more, or 29.75 g ai/ha or more).

In some embodiments, the tribenuron or agriculturally acceptable salt or ester thereof is applied to vegetation or an area adjacent the vegetation or applied to soil or water to prevent the emergence or growth of vegetation in an amount of 30 g ai/ha or less (e.g., 29.75 g ai/ha or less, 29.5 g ai/ha or less, 29.25 g ai/ha or less, 29 g ai/ha or less, 28.5 g ai/ha or less, 28 g ai/ha or less, 27.5 g ai/ha or less, 27 g ai/ha or less, 26.5 g ai/ha or less, 26 g ai/ha or less, 25 g ai/ha or less, 24 g ai/ha or less, 23 g ai/ha or less, 22 g ai/ha or less, 21 g ai/ha or less, 20 g ai/ha or less, 19 g ai/ha or less, 18 g ai/ha or less, 17 g ai/ha or less, 16 g ai/ha or less, 15 g ai/ha or less, 14 g ai/ha or less, 13 g ai/ha or less, 12 g ai/ha or less, 11 g ai/ha or less, 10 g ai/ha or less, 9.5 g ai/ha or less, 9 g ai/ha or less, 8.5 g ai/ha or less, 8 g ai/ha or less, 7.5 g ai/ha or less, 7 g ai/ha or less, 6.5 g ai/ha or less, 6 g ai/ha or less, 5.75 g ai/ha or less, 5.5 g ai/ha or less, 5.25 g ai/ha or less, 5 g ai/ha or less, 4.75 g ai/ha or less, 4.5 g ai/ha or less, 4.25 g ai/ha or less, or 4 g ai/ha or less).

The tribenuron or agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the imazamox or agriculturally acceptable salt thereof is applied to vegetation or an area adjacent the vegetation or applied to soil or water to prevent the emergence or growth of vegetation in an amount of 3.75-30 g ai/ha (e.g., 3.75-29 g ai/ha, 3.75-28 g ai/ha, 3.75-27 g ai/ha, 3.75-25 g ai/ha, 4-30 g ai/ha, 4-28 g ai/ha, 4-26 g ai/ha, 4-25 g ai/ha, 5-30 g ai/ha, 5-ai/ha, 5-28 g ai/ha, 5-25 g ai/ha, 6-30 g ai/ha, or 6-25 g ai/ha).

II. COMPOSITIONS

A. Herbicidal Mixtures or Combinations

The (a) pyridine carboxylic acid herbicide or an agriculturally acceptable N-oxide, salt, or ester thereof is mixed with or applied in combination with (b) an ALS inhibitor or an agriculturally acceptable salt or ester thereof. In some embodiments, (a) and (b) can be provided in an amount sufficient to induce a herbicidal effect. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Tenth Edition, 20014, p. 487, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X*Y}{100}$$

wherein

X=effect in percent using (a) a pyridine carboxylic acid herbicide or an agriculturally acceptable N-oxide, salt, or ester thereof at an application rate a;

Y=effect in percent using (b) an ALS inhibitor or an agriculturally acceptable salt or ester thereof at an application rate b;

E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of a pyridine carboxylic acid herbicide or an agriculturally acceptable N-oxide, salt, or ester thereof and an ALS inhibitor or an agriculturally acceptable salt or ester thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the observed effect for undesired vegetation is at least 1%, at least 2%, at least 3%, at least 4%, at least 5%, at least 10%, at least 15%, at least 20%, or at least 25% greater than the effect (E) calculated according to the Colby equation (e.g., an observed effect of 96% would be 4% greater than an calculated effect (E) of 92%). In some embodiments, for undesired vegetation, the difference ($D_O$) between 100% and the observed effect is at least 5%, at least 10%, at least 15%, at least 20%, at least 25%, at least 30%, at least 35%, at least 40%, at least 45%, or at least 50% less than the difference ($D_E$) between 100% and the effect (E) calculated according to the Colby equation (e.g., an observed effect of 96% would produce a $D_O$ of 4%, a calculated effect (E) of 92% would produce a $D_E$ of 8%, and $D_O$ would be 50% less than or half of $D_E$).

In some embodiments, the weight ratio of (a) a pyridine carboxylic acid herbicide or an agriculturally acceptable N-oxide, salt, or ester thereof (in g ae/ha) to (b) an ALS inhibitor or an agriculturally acceptable salt or ester thereof (in g ai/ha) is 1:34000 or more (e.g., 1:3200 or more, 1:3000 or more, 1:2800 or more, 1:2600 or more, 1:2400 or more, 1:2200 or more, 1:2000 or more, 1:1800 or more, 1:1600 or more, 1:1400 or more, 1:1200 or more, 1:1000 or more, 1:900 or more, 1:800 or more, 1:700 or more, 1:600 or more, 1:500 or more, 1:400 or more, 1:300 or more, 1:200 or more, 1:100 or more, 1:90 or more, 1:80 or more, 1:70 or more, 1:60 or more, 1:50 or more, 1:40 or more, 1:30 or more, 1:20 or more, 1:10 or more, 1:9 or more, 1:8 or more, 1:7 or more, 1:6 or more, 1:5 or more, 1:4 or more, 1:3 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 3:1 or more, 4:1 or more, 5:1 or more, 6:1 or more, 7:1 or more, 8:1 or more, 9:1 or more, 10:1 or more, 20:1 or more, 30:1 or more, 40:1 or more, 50:1 or more, 60:1 or more, 70:1 or more, 80:1 or more, 90:1 or more, 100:1 or more, 200:1 or more, 300:1 or more, 400:1 or more, 500:1 or more, 600:1 or more, 700:1 or more, 800:1 or more, 900:1 or more, 1000:1 or more, or 1100:1 or more).

In some embodiments, the weight ratio of (a) a pyridine carboxylic acid herbicide or an agriculturally acceptable N-oxide, salt, or ester thereof (in g ae/ha) to (b) an ALS inhibitor or an agriculturally acceptable salt or ester thereof (in g ai/ha) is 1200:1 or less (e.g., 1100:1 or less, 1000:1 or less, 900:1 or less, 800:1 or less, 700:1 or less, 600:1 or less, 500:1 or less, 400:1 or less, 300:1 or less, 200:1 or less, 100:1 or less, 90:1 or less, 80:1 or less, 70:1 or less, 60:1 or less, 50:1 or less, 40:1 or less, 30:1 or less, 20:1 or less, 10:1 or less, 9:1 or less, 8:1 or less, 7:1 or less, 6:1 or less, 5:1 or less, 4:1 or less, 3:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:3 or less, 1:4 or less, 1:5 or less, 1:6 or less, 1:7 or less, 1:8 or less, 1:9 or less, 1:10 or less, 1:20 or less, 1:30 or less, 1:40 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, 1:900 or less, 1:1000 or less, 1:1200 or less, 1:1400 or less, 1:1600 or less, 1:1800 or less, 1:2000 or less, 1:2200 or less, 1:2400 or less, 1:2600 or less, 1:2800 or less, 1:3000 or less, or 1:3200 or less).

The weight ratio of (a) a pyridine carboxylic acid herbicide or an agriculturally acceptable N-oxide, salt, or ester thereof (in g ae/ha) to (b) an ALS inhibitor or an agriculturally acceptable salt or ester thereof (in g ai/ha) can range from any of the minimum ratios described above to any of the maximum values described above. In some embodiments, the weight ratio of (a) a pyridine carboxylic acid herbicide or an agriculturally acceptable N-oxide, salt, or ester thereof (in g ae/ha) to (b) an ALS inhibitor or an agriculturally acceptable salt or ester thereof (in g ai/ha) is from 1:34000 to 1200:1 (e.g., from 1:3400 to 1000:1, from 1:3200 to 1000:1, from 1:3200 to 800:1, from 1:3000 to 600:1, from 1:2500 to 400:1, from 1:2000 to 200:1, from 1:1000 to 1200:1, from 1:1000 to 1000:1, from 1:1000 to 100:1, from 1:800 to 1000:1, from 1:800 to 800:1, from 1:800 to 400:1, from 1:600 to 600:1, from 1:400 to 400:1, from 1:400 to 200:1, from 1:200 to 200:1, from 1:200 to 100:1, from 1:100 to 100:1, from 1:50 to 50:1, from 1:40 to 40:1, from 1:30 to 30:1, from 1:20 to 20:1, from 1:10 to 10:1, 1:1000 to 20:1, from 1:900 to 10:1, from 1:900 to 50:1, from 1:800 to 40:1, from 1:700 to 30:1, from 1:600 to 20:1, from 1:500 to 15:1, from 1:400 to 10:1, from 1:300 to 9:1, from 1:200 to 8:1, from 1:100 to 7:1, from 1:50 to 6:1, from 1:40 to 5:1, from 1:30 to 4:1, from 1:20 to 3:1, from 1:10 to 2:1, from 1:5 to 5:1, from 1:4 to 4:1, from 1:3 to 3:1, or from 1:2 to 2:1).

In some embodiments, (b) includes a triazolopyrimidine sulfonamide or an agriculturally acceptable salt or ester thereof. In some embodiments, the weight ratio of (a) a pyridine carboxylic acid herbicide or an agriculturally acceptable N-oxide, salt, or ester thereof (in g ae/ha) to (b) a triazolopyrimidine sulfonamide or an agriculturally acceptable salt or ester thereof (in g ai/ha) is 1:2000 or more (e.g., 1:1900 or more, 1:1800 or more, 1:1700 or more, 1:1600 or more, 1:1500 or more, 1:1400 or more, 1:1300 or more, 1:1200 or more, 1:1100 or more, 1:1000 or more, 1:900 or more, 1:800 or more, 1:700 or more, 1:600 or more, 1:500 or more, 1:400 or more, 1:300 or more, 1:200 or more, 1:100 or more, 1:90 or more, 1:80 or more, 1:70 or more, 1:60 or more, 1:50 or more, 1:40 or more, 1:30 or more, 1:20 or more, 1:10 or more, 1:9 or more, 1:8 or more, 1:7 or more, 1:6 or more, 1:5 or more, 1:4 or more, 1:3 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 3:1 or more, 4:1 or more, 5:1 or more, 6:1 or more, 7:1 or more, 8:1 or more, 9:1 or more, 10:1 or more, 20:1 or more, 30:1 or more, 40:1 or more, 50:1 or more, 60:1 or more, 70:1 or more, 80:1 or more, 90:1 or more, 100:1 or more, 200:1 or more, 300:1 or more, 400:1 or more, 500:1 or more, 600:1 or more, 700:1 or more, 800:1 or more, 900:1 or more, 1000:1 or more, or 1100:1 or more).

In some embodiments, the weight ratio of (a) a pyridine carboxylic acid herbicide or an agriculturally acceptable N-oxide, salt, or ester thereof (in g ae/ha) to (b) a triazolopyrimidine sulfonamide or an agriculturally acceptable salt or ester thereof (in g ai ha) is 1200:1 or less (e.g., 1100:1 or less, 1000:1 or less, 900:1 or less, 800:1 or less, 700:1 or less, 600:1 or less, 500:1 or less, 400:1 or less, 300:1 or less, 200:1 or less, 100:1 or less, 90:1 or less, 80:1 or less, 70:1 or less, 60:1 or less, 50:1 or less, 40:1 or less, 30:1 or less, 20:1 or less, 10:1 or less, 9:1 or less, 8:1 or less, 7:1 or less, 6:1 or less, 5:1 or less, 4:1 or less, 3:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:3 or less, 1:4 or less, 1:5 or less, 1:6 or less, 1:7 or less, 1:8 or less, 1:9 or less, 1:10 or less, 1:20 or less, 1:30 or less, 1:40 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, 1:900 or less, 1:1000 or less, 1:1100 or less, 1:1200 or less, 1:1300 or less, 1:1400 or less, 1:1500 or less, 1:1600 or less, 1:1700 or less, 1:1800 or less, or 1:1900 or less).

The weight ratio of (a) a pyridine carboxylic acid herbicide or an agriculturally acceptable N-oxide, salt, or ester thereof to (b) a triazolopyrimidine sulfonamide or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) triazolopyrimidine sulfonamide or an agriculturally acceptable salt or ester thereof is from 1:2000 to 1200:1 (e.g., from 1:2000 to 1000:1, from 1:2000 to 800:1, from 1:2000 to 600:1, from 1:1000 to 400:1, from 1:500 to 200:1, from 1:400 to 190:1, from 1:300 to 180:1, from 1:200 to 170:1, from 1:50 to 120:1, from 1:1.5 to 150:1, from 1:1.5 to 100:1, from 1:1.5 to 50:1, from 1:10 to 16:1, or from 1:1.5 to 40:1). In certain embodiments, the weight ratio of (a) a pyridine carboxylic acid herbicide or an agriculturally acceptable N-oxide, salt, or ester thereof to (b) a triazolopyrimidine sulfonamide or an agriculturally acceptable salt or ester thereof is from 1:3.8 to 16:1, or from 1:5 to 6:1.

In some embodiments, (b) includes an imidazolinone or an agriculturally acceptable salt or ester thereof. In some embodiments, the weight ratio of (a) a pyridine carboxylic acid herbicide or an agriculturally acceptable N-oxide, salt, or ester thereof (in g ae/ha) to (b) imidazolinone or an agriculturally acceptable salt or ester thereof (in g ai/ha) is 1:3400 or more (e.g., 1:3200 or more, 1:3000 or more, 1:2800 or more, 1:2600 or more, 1:2400 or more, 1:2200 or more, 1:2000 or more, 1:1800 or more, 1:1600 or more, 1:1400 or more, 1:1200 or more, 1:1000 or more, 1:900 or more, 1:800 or more, 1:700 or more, 1:600 or more, 1:500 or more, 1:400 or more, 1:300 or more, 1:200 or more, 1:100 or more, 1:90 or more, 1:80 or more, 1:70 or more, 1:60 or more, 1:50 or more, 1:40 or more, 1:30 or more, 1:20 or more, 1:10 or more, 1:9 or more, 1:8 or more, 1:7 or more, 1:6 or more, 1:5 or more, 1:4 or more, 1:3 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 3:1 or more, 4:1 or more, 5:1 or more, 6:1 or more, 7:1 or more, 8:1 or more, 9:1 or more, 10:1 or more, 15:1 or more, 20:1 or more, 25:1 or more, 30:1 or more, 35:1 or more, 40:1 or more, 45:1 or more, 50:1 or more, 51:1 or more, 52:1 or more, 53:1 or more, 54:1 or more, 55:1 or more, 56:1 or more, 57:1 or more, 58:1 or more, or 59:1 or more).

In some embodiments, the weight ratio of (a) a pyridine carboxylic acid herbicide or an agriculturally acceptable N-oxide, salt, or ester thereof (in g ae/ha) to (b) an imidazolinone or an agriculturally acceptable salt or ester thereof (in g ai/ha) is 60:1 or less (e.g., 59:1 or less, 58:1 or less, 57:1 or less, 56:1 or less, 55:1 or less, 54:1 or less, 53:1 or less, 52:1 or less, 51:1 or less, 50:1 or less, 45:1 or less, 40:1 or less, 35:1 or less, 30:1 or less, 25:1 or less, 20:1 or less, 15:1 or less, 10:1 or less, 9:1 or less, 8:1 or less, 7:1 or less, 6:1 or less, 5:1 or less, 4:1 or less, 3:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:3 or less, 1:4 or less, 1:5 or less, 1:6 or less, 1:7 or less, 1:8 or less, 1:9 or less, 1:10 or less, 1:20 or less, 1:30 or less, 1:40 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, 1:900 or less, 1:1000 or less, 1:1200 or less, 1:1400 or less, 1:1600 or less, 1:1800 or less, 1:2000 or less, 1:2200 or less, 1:2400 or less, 1:2600 or less, 1:2800 or less, 1:3000 or less, or 1:3200 or less).

The weight ratio of (a) a pyridine carboxylic acid herbicide or an agriculturally acceptable N-oxide, salt, or ester thereof to (b) an imidazolinone or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) an imidazolinone or an agriculturally acceptable salt or ester thereof is from 1:3400 to 60:1 (e.g., from 1:3000 to 60:1, from 1:2500 to 50:1, from 1:2000 to 50:1, from 1:1400 to 60:1, from 1:1500 to 50:1, from 1:1000 to 40:1, from 1:750 to 50:1, from 1:440 to 30:1, from 1:280 to 17:1, from 1:100 to 15:1, from 1:50 to 10:1, or from 1:50 to 7:1). In certain embodiments, the weight ratio of (a) a pyridine carboxylic acid herbicide or an agriculturally acceptable N-oxide, salt, or ester thereof to (b) an imidazolinone or an agriculturally acceptable salt or ester thereof is from 1:10 to 5:1, or from 1:10 to 1:6.

In some embodiments, (b) includes pyrimidinyl oxybenzoate or an agriculturally acceptable salt or ester thereof. In some embodiments, the weight ratio of (a) a pyridine carboxylic acid herbicide or an agriculturally acceptable N-oxide, salt, or ester thereof (in g ae/ha) to (b) pyrimidinyl oxybenzoate or an agriculturally acceptable salt or ester thereof (in g ai/ha) is 1:600 or more (e.g., 1:590 or more, 1:580 or more, 1:570 or more, 1:560 or more, 1:550 or more, 1:500 or more, 1:450 or more, 1:400 or more, 1:350 or more, 1:300 or more, 1:250 or more, 1:225 or more, 1:200 or more, 1:175 or more, 1:150 or more, 1:125 or more, 1:100 or more, 1:90 or more, 1:80 or more, 1:70 or more, 1:60 or more, 1:50 or more, 1:40 or more, 1:30 or more, 1:20 or more, 1:15 or more, 1:10 or more, 1:5 or more, 1:2.5 or more, 1:1.25 or more, 1:1.1 or more, 1:1 or more, 1.1:1 or more, 1.25:1 or more, 1.5:1 or more, 2:1 or more, 3:1 or more, 4:1 or more, 5:1 or more, 6:1 or more, 7:1 or more, 8:1 or more, 9:1 or more, 10:1 or more, 12:1 or more, 14:1 or more, 16:1 or more, 18:1 or more, 20:1 or more, 22:1 or more, 24:1 or more, 26:1 or more, 28:1 or more, 30:1 or more, 32:1 or more, 34:1 or more, 36:1 or more, 38:1 or more, 40:1 or more, 42:1 or more, 44:1 or more, 46:1 or more, 48:1 or more, 50:1 or more, 51:1 or more, 52:1 or more, 53:1 or more, 54:1 or more, 55:1 or more, 56:1 or more, 58:1 or more, or 59:1 or more).

In some embodiments, the weight ratio of (a) a pyridine carboxylic acid herbicide or an agriculturally acceptable N-oxide, salt, or ester thereof (in g ae/ha) to (b) a pyrimidinyl oxybenzoate or an agriculturally acceptable salt or ester thereof (in g ai/ha) is 60:1 or less (e.g., 59:1 or less, 58:1 or less, 57:1 or less, 56:1 or less, 55:1 or less, 54:1 or less, 53:1 or less, 52:1 or less, 51:1 or less, 50:1 or less, 48:1 or less, 46:1 or less, 44:1 or less, 42:1 or less, 40:1 or less, 38:1 or less, 36:1 or less, 34:1 or less, 32:1 or less, 30:1 or less, 28:1 or less, 26:1 or less, 24:1 or less, 22:1 or less, 20:1 or less, 18:1 or less, 16:1 or less, 14:1 or less, 12:1 or less, 10:1 or less, 9:1 or less, 8:1 or less, 7:1 or less, 6:1 or less, 5:1 or less, 4:1 or less, 3:1 or less, 2:1 or less, 1.5:1 or less, 1.25:1 or less, 1.1:1 or less, 1:1 or less, 1:1.1 or less, 1:1.25 or less, 1:2.5 or less, 1:5 or less, 1:10 or less, 1:15 or less, 1:20 or less, 1:30 or less, 1:40 or less, 1:50 or less, 1:60 or less, 1:70 or less, 1:80 or less, 1:90 or less, 1:100 or less, 1:125 or less, 1:150 or less, 1:175 or less, 1:200 or less, 1:225 or less, 1:250 or less, 1:300 or less, 1:350 or less, 1:400 or less, 1:450 or less, 1:500 or less, 1:550 or less, 1:560 or less, 1:570 or less, 1:580 or less, or 1:590 or less).

The weight ratio of (a) a pyridine carboxylic acid herbicide or an agriculturally acceptable N-oxide, salt, or ester thereof to (b) a pyrimidinyl oxybenzoate or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) a pyrimidinyl oxybenzoate or an agriculturally acceptable salt thereof is from 1:600 to 60:1 (e.g., from 1:500 to 60:1, from 1:500 to 55:1, from 1:400 to 52:1, from 1:400 to 50:1, from 1:300 to 47:1, from 1:250 to 45:1, from 1:200 to 42:1, from 1:140 to 40:1, from 1:130 to 30:1, 1:120 to 20:1 or from 1:100 to 10:1). In certain embodiments, the weight ratio of (a) a pyridine carboxylic acid herbicide or an agriculturally acceptable N-oxide, salt, or ester thereof to (b) a pyrimidinyl oxybenzoate or an agriculturally acceptable salt or ester thereof is from 1:15 to 5:1, or from 1:10 to 5:1.

In some embodiments, (b) includes a sulfonylaminocarbonyl triazolinone or an agriculturally acceptable salt or ester thereof. In some embodiments, the weight ratio of (a) a pyridine carboxylic acid herbicide or an agriculturally acceptable N-oxide, salt, or ester thereof (in g ae/ha) to (b) sulfonylaminocarbonyl triazolinone or an agriculturally acceptable salt or ester thereof (in g ai/ha) is 1:600 or more (e.g., 1:590 or more, 1:580 or more, 1:570 or more, 1:560 or more, 1:550 or more, 1:500 or more, 1:450 or more, 1:400 or more, 1:350 or more, 1:300 or more, 1:250 or more, 1:225 or more, 1:200 or more, 1:175 or more, 1:150 or more, 1:125 or more, 1:100 or more, 1:90 or more, 1:80 or more, 1:70 or more, 1:60 or more, 1:50 or more, 1:40 or more, 1:30 or more, 1:20 or more, 1:15 or more, 1:10 or more, 1:5 or more, 1:2.5 or more, 1:1.25 or more, 1:1.1 or more, 1:1 or more, 1.1:1 or more, 1.25:1 or more, 1.5:1 or more, 2:1 or more, 3:1 or more, 4:1 or more, 5:1 or more, 6:1 or more, 7:1 or more, 8:1 or more, 9:1 or more, 10:1 or more, 12:1 or more, 14:1 or more, 16:1 or more, 18:1 or more, 20:1 or more, 25:1 or more, 30:1 or more, 35:1 or more, 40:1 or more, 45:1 or more, 50:1 or more, 55:1 or more, 60:1 or more, 65:1 or more, 70:1 or more, 75:1 or more, 80:1 or more, 85:1 or more, 90:1 or more, 95:1 or more, 100:1 or more, 105:1 or more, 110:1 or more, 112:1 or more, 114:1 or more, 116:1 or more, 117:1 or more, 118:1 or more, or 119:1 or more).

In some embodiments, the weight ratio of (a) a pyridine carboxylic acid herbicide or an agriculturally acceptable N-oxide, salt, or ester thereof (in g ae/ha) to (b) a sulfonylaminocarbonyl triazolinone or an agriculturally acceptable salt or ester thereof (in g ai/ha) is 120:1 or less (e.g., 119:1 or less, 118:1 or less, 117:1 or less, 116:1 or less, 114:1 or less, 112:1 or less, 110:1 or less, 105:1 or less, 100:1 or less, 95:1 or less, 90:1 or less, 85:1 or less, 80:1 or less, 75:1 or less, 70:1 or less, 65:1 or less, 60:1 or less, 55:1 or less, 50:1 or less, 45:1 or less, 40:1 or less, 35:1 or less, 30:1 or less, 25:1 or less, 20:1 or less, 18:1 or less, 16:1 or less, 14:1 or less, 12:1 or less, 10:1 or less, 9:1 or less, 8:1 or less, 7:1 or less, 6:1 or less, 5:1 or less, 4:1 or less, 3:1 or less, 2:1 or less, 1.5:1 or less, 1.25:1 or less, 1.1:1 or less, 1:1 or less, 1:1.1 or less, 1:1.25 or less, 1:2.5 or less, 1:5 or less, 1:10 or less, 1:15 or less, 1:20 or less, 1:30 or less, 1:40 or less, 1:50 or less, 1:60 or less, 1:70 or less, 1:80 or less, 1:90 or less, 1:100 or less, 1:125 or less, 1:150 or less, 1:175 or less, 1:200 or less, 1:225 or less, 1:250 or less, 1:300 or less, 1:350 or less, 1:400 or less, 1:450 or less, 1:500 or less, 1:550 or less, 1:560 or less, 1:570 or less, 1:580 or less, or 1:590 or less).

The weight ratio of (a) a pyridine carboxylic acid herbicide or an agriculturally acceptable N-oxide, salt, or ester thereof to (b) a sulfonylaminocarbonyl triazolinone or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) sulfonylaminocarbonyl triazolinone or an agriculturally acceptable salt or ester thereof is from 1:600 to 120:1 (e.g., from 1:500 to 120:1, from 1:500 to 100:1, from 1:400 to 100:1, from 1:400 to 80:1, from 1:300 to 120:1, from 1:300 to 100:1, from 1:250 to 120:1, from 1:200 to 100:1, from 1:175 to 85:1, from 1:150 to 80:1, from 1:140 to 80:1, from 1:130 to 50:1, or from 1:100 to 25:1). In certain embodiments, the weight ratio of (a) a pyridine carboxylic acid herbicide or an agriculturally acceptable N-oxide, salt, or ester thereof to (b) sulfonylaminocarbonyl triazolinone or an agriculturally acceptable salt or ester thereof is from 1:7.5 to 10:1, or from 1:5 to 1:1.

In some embodiments, (b) includes sulfonylurea or an agriculturally acceptable salt or ester thereof. In some embodiments, the weight ratio of (a) a pyridine carboxylic acid herbicide or an agriculturally acceptable N-oxide, salt, or ester thereof (in g ae/ha) to (b) a sulfonylurea or an agriculturally acceptable salt thereof (in g ai/ha) is 1:400 or more (e.g., 1:390 or more, 1:380 or more, 1:360 or more, 1:360 or more, 1:350 or more, 1:340 or more, 1:330 or more, 1:320 or more, 1:310 or more, 1:300 or more, 1:250 or more, 1:225 or more, 1:200 or more, 1:175 or more, 1:150 or more, 1:125 or more, 1:100 or more, 1:90 or more, 1:80 or more, 1:70 or more, 1:60 or more, 1:50 or more, 1:40 or more, 1:30 or more, 1:20 or more, 1:15 or more, 1:10 or more, 1:5 or more, 1:2.5 or more, 1:1.25 or more, 1:1.1 or more, 1:1 or more, 1.1:1 or more, 1.25:1 or more, 2.5:1 or more, 5:1 or more, 10:1 or more, 15:1 or more, 20:1 or more, 30:1 or more, 40:1 or more, 50:1 or more, 60:1 or more, 70:1 or more, 80:1 or more, 90:1 or more, 100:1 or more, 125:1 or more, 150:1 or more, 175:1 or more, 200:1 or more, 225:1 or more, 250:1 or more, 300:1 or more, 310:1 or more, 320:1 or more, 330:1 or more, 340:1 or more, 350:1 or more, 360:1 or more, 380:1 or more, 385:1 or more, 390:1 or more, 392:1 or more, 394:1 or more, 396:1 or more, 397:1 or more, 398:1 or more, or 399:1 or more).

In some embodiments, the weight ratio of (a) a pyridine carboxylic acid herbicide or an agriculturally acceptable N-oxide, salt, or ester thereof (in g ae/ha) to (b) a sulfonylurea or an agriculturally acceptable salt or ester thereof (in g ai/ha) is 400:1 or less (e.g., 390:1 or less, 380:1 or less, 370:1 or less, 360:1 or less, 350:1 or less, 340:1 or less, 330:1 or less, 320:1 or less, 310:1 or less, 300:1 or less, 250:1 or less, 225:1 or less, 200:1 or less, 175:1 or less, 150:1 or less, 125:1 or less, 100:1 or less, 90:1 or less, 80:1 or less, 70:1 or less, 60:1 or less, 50:1 or less, 40:1 or less, 30:1 or less, 20:1 or less, 15:1 or less, 10:1 or less, 5:1 or less, 2.5:1 or less, 1.25:1 or less, 1.1:1 or less, 1:1 or less, 1:1.1 or less, 1:1.25 or less, 1:2.5 or less, 1:5 or less, 1:10 or less, 1:15 or less, 1:20 or less, 1:30 or less, 1:40 or less, 1:50 or less, 1:60 or less, 1:70 or less, 1:80 or less, 1:90 or less, 1:100 or less, 1:125 or less, 1:150 or less, 1:175 or less, 1:200 or less, 1:225 or less, 1:250 or less, 1:300 or less, 1:310 or less, 1:320 or less, 1:330 or less, 1:340 or less, 1:350 or less, 1:360 or less, or 1:390 or less).

The weight ratio of (a) a pyridine carboxylic acid herbicide or an agriculturally acceptable N-oxide, salt, or ester thereof to (b) a sulfonylurea or an agriculturally acceptable salt or ester thereof can range from any of the minimum ratios described above to any of the maximum values described above. In some embodiments, the weight ratio of (a) a pyridine carboxylic acid herbicide or an agriculturally acceptable N-oxide, salt, or ester thereof to (b) a sulfonylurea or an agriculturally acceptable salt or ester thereof is from 1:400 to 400:1 (e.g., from 1:300 to 300:1, from 1:250 to 250:1, from 1:200 to 200:1, from 1:175 to 175:1, from 1:150 to 150:1, from 1:125 to 125:1, from 1:100 to 100:1, from 1:75 to 75:1, from 1:50 to 50:1, from 1:40 to 40:1, from 1:30 to 30:1, from 1:25 to 25:1, or from 1:20 to 20:1). In certain embodiments, the weight ratio of (a) a pyridine carboxylic acid herbicide or an agriculturally acceptable N-oxide, salt, or ester thereof to (b) sulfonylurea or an agriculturally acceptable salt thereof is from 1:10 to 5:1, or from 1:8.75 to 2:1.

In some embodiments, the active ingredients in the compositions disclosed herein consist of (a) a pyridine carboxylic acid herbicide or an agriculturally acceptable N-oxide, salt, or ester thereof and (b) an ALS inhibitor or an agriculturally acceptable salt or ester thereof.

B. Formulations

The present disclosure also relates to formulations of the compositions and methods disclosed herein. In some embodiments, the formulation can be in the form of a single package formulation including both (a) a pyridine carboxylic acid herbicide or an agriculturally acceptable N-oxide, salt, or ester thereof and (b) an ALS inhibitor or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, self-emulsifying formulations, pastes, dusts, and materials for spreading or granules.

In some embodiments, (a) a pyridine carboxylic acid herbicide or an agriculturally acceptable N-oxide, salt, or ester thereof and/or (b) an ALS inhibitor or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C., or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the pyridine carboxylic acid herbicide or agriculturally acceptable N-oxide, salt, or ester thereof. In some embodiments, the additive is premixed with the ALS inhibitor or agriculturally acceptable salt or ester thereof.

C. Other Actives

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, aminocyclopyrachlor, 4-aminopicolinic acid based herbicides, such as halauxifen, halauxifen-methyl, 4-amino-3-chloro-6-(4-chloro-2-fluoro-3-methoxyphenyl)-5-fluoro-2-pyridinecarboxylic acis, benzyl 4-amino-3-chloro-6-(4-chloro-2-fluoro-3-methoxyphenyl)-5-fluoro-2-pyridinecarboxylate, and those described in U.S. Pat. Nos. 7,314,849 and 7,432,227 to Balko, et al., aminopyralid, amiprofos-methyl, amitrole, ammonium sulfamate, anilofos, anisuron, asulam, atraton, atrazine, azafenidin, aziprotryne, barban, BCPC, beflubutamid, benazolin, bencarbazone, benfluralin, benfuresate, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlornitrofen, chloropon, chlorotoluron, chloroxuron, chloroxynil, chlorpropham, chlorthal, chlorthiamid, cinidon-ethyl, cinmethylin, cisanilide, clacyfos, clethodim, cliodinate, clodinafop-propargyl, clofop, clomazone, clomeprop, cloprop, cloproxydim, clopyralid, CMA, copper sulfate, CPMF, CPPC, credazine, cresol, cumyluron, cyanatryn, cyanazine, cycloate, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethidimuron, ethiolate, ethobenzamid, etobenzamid, ethofumesate, ethoxyfen, etinofen, etnipromid, etobenzanid, EXD, fenasulam, fenoprop, fenoxaprop, fcnoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, fluazifop, fluazifop-P-butyl, fluazolate, fluchloralin, flufenacet, flufenican, flufenpyr-ethyl, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, fluridone, flurochloridone, fluroxypyr, fluroxypyr-meptyl, flurtamone, fluthiacet, fomesafen, fosamine, fumiclorac, furyloxyfen, glufosinate, glufosinate-ammonium, glufosinate-P-ammonium, glyphosate salts and esters, halosafen, haloxydine, hexachloroacetone, hexaflurate, hexazinone, indanofan, indaziflam, iodobonil, iodomethane, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesotrione, metam, metamifop, metamitron, metazachlor, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metoxuron, metribuzin, molinate, monalide, monisouron, monochloroacetic acid, monolinuron, monuron, morfamquat, MSMA, naproanilide, napropamide, napropamide-M, naptalam, neburon, nipyraclofen, nitralin, nitrofen, nitrofluorfen, norflurazon, noruron, OCH, orbencarb, ortho-dichlorobenzene, oryzalin, oxadiargyl, oxadiazon, oxapyrazon, oxaziclomefone, oxyfluorfen, paraflufen-ethyl, parafluron, paraquat, pebulate, pelargonic acid, pendimethalin, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, procyazine, prodiamine, profluazol, profluralin, profoxydim, proglinazine, prohexadione-calcium, prometon, prometryn, pronamide, propachlor, propanil, propaquizafop, propazine, propham, propisochlor, propyzamide, prosulfalin, prosulfocarb, proxan, prynachlor, pydanon, pyraclonil, pyraflufen-ethyl, pyrasulfotole, pyrazogyl, pyrazolynate, pyrazoxyfen, pyributicarb, pyriclor, pyridafol, pyridate, quinclorac, quinmerac, quinoclamine, quinonamid, quizalofop, quizalofop-P-ethyl, rhodethanil, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfosate, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiameturon, thiazafluron, thiazopyr, thidiazimin, thidiazuron, thiobencarb, tiafenacil, tiocarbazil, tioclorim, tolpyralate, topramezone, tralkoxydim, tri-allate, triafamone, triaziflam, tricamba, triclopyr choline salt, triclopyr esters and amines, tridiphane, trietazine, trifludimoxazin, trifluralin, trifop, trifopsime, trihydroxytriazine, trimeturon, tripropindan, tritac, vernolate, xylachlor and salts, esters, optically active isomers, and mixtures thereof.

In some embodiments, the additional pesticide or an agriculturally acceptable salt or ester thereof is provided in a premixed formulation with (a), (b), or combinations thereof. In some embodiments, the pyridine carboxylic acid herbicide or an agriculturally acceptable N-oxide, salt, or ester thereof is provided in a premixed formulation with an additional pesticide. In some embodiments, the ALS inhibitor or an agriculturally acceptable salt or ester thereof is provided in a premixed formulation with an additional pesticide. In some embodiments, the florasulam the cloransulam, the diclosulam, the flumetsulam, the metosulam, the penoxsulam, the pyroxsulam, or an agriculturally acceptable salt thereof, is provided in a premixed formulation with an additional pesticide. In some embodiments, the imazamethabenz, the imazamox, the imazapic, the imazapyr, the imazaquin, the imazethapyr, or an agriculturally acceptable salt or ester thereof, is provided in a premixed formulation with an additional pesticide. In some embodiments, the bispyribac, the pyribenzoxim, the pyriftalid, the pyriminobac, the pyrimisulfan, the pyrithiobac, or an agriculturally acceptable salt or ester thereof, is provided in a premixed formulation with an additional pesticide. In some embodiments, the flucarbazone, the propoxycarbazone, the thiencarbazone, or an agriculturally acceptable salt or ester thereof, is provided in a premixed formulation with an additional pesticide. In some embodiments, the amidosulfuron, the azimsulfuron, the bensulfuron, the chlorimuron, the chlorsulfuron, the cinosulfuron, the cyclosulfamuron, the ethametsulfuron, the ethoxysulfuron, the flazasulfuron, the flucetosulfuron, the flupyrsulfuron, the foramsulfuron, the halosulfuron, the imazosulfuron, the iodosulfuron, the iofensulfuron, the mesosulfuron, the metazosulfuron, the metsulfuron, the nicosulfuron, the orthosulfamuron, the oxasulfuron, the primisulfuron, the propyrisulfuron, the prosulfuron, the pyrazosulfuron, the rimsulfuron, the sulfometuron, the sulfosulfuron, the triasulfuron, the tribenuron, the thifensulfuron, the trifloxysulfuron, the triflusulfuron, the tritosulfuron, or an agriculturally acceptable salt or ester thereof, is provided in a premixed formulation with an additional pesticide.

D. Adjuvants/Carriers/Colorants/Adhesives

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, herbicide safeners, adhesives (for instance, for use in seed formulations), surfactants, protective colloids, emulsifiers, tackifiers, and mixtures thereof.

Exemplary agriculturally acceptable adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant: $C_9$-$C_{11}$ alkylpolyglycoside; phosphate alcohol ethoxylate; natural primary alcohol ($C_{12}$-$C_{16}$) ethoxylate or less, di-sec-butylphenol EO-PO block copolymer; polysiloxane-methyl cap; nonylphenol ethoxylate+ urea ammonium nitrate; emulsified methylated seed oil; tridecyl alcohol (synthetic) ethoxylate (8 EO); tallow amine ethoxylate (15 EO); and PEG(400) dioleate-99.

In some embodiments, the additive is a safener, which is an organic compound leading to better crop plant compatibility when applied with a herbicide. In some embodiments, the safener itself is herbicidally active. In some embodiments, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, R29148, and N-phenylsulfonylbenzoic acid amides, as well as thereof agriculturally acceptable salts and, provided they have a carboxyl group, their agriculturally acceptable derivatives. In some embodiments, the safener can be cloquintocet or an ester or salt or ester thereof, such as cloquintocet (mexyl). In some embodiments, the safener can be dichlormid. In some embodiments, the safener is employed in rice, cereal, or maize. For example, dichlormid or cloquintocet can be used to antagonize harmful effects of the compositions on rice, row crops, and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivatives, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes or oil dispersions can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

III. METHODS OF USE

A. Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

In some embodiments, a method of controlling undesirable vegetation which comprises contacting the vegetation or the locus thereof with or applying to the soil or water to prevent the emergence or growth of vegetation any of the compositions is disclosed herein.

The compositions disclosed herein can be applied pre-emergence (before the emergence of undesirable vegetation) or post-emergence (i.e., during and/or after emergence of the undesirable vegetation). If desired, the compositions can be applied as an in-water application. In some embodiments, the pyridine carboxylic acid or an agriculturally acceptable N-oxide, salt, or ester thereof and the ALS inhibitor or an agriculturally acceptable salt or ester thereof are applied simultaneously.

When the compositions are used in crops, the compositions can be applied after seeding and before or after the emergence of the crop plants. In some embodiments, the compositions disclosed herein show good crop tolerance even when the crop has already emerged and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by). In some embodiments, the compositions disclosed herein can be applied as dry formulations (e.g., granules, WDGs, etc.) into water.

In some embodiments, herbicidal activity is exhibited by the compounds of the mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, wheat, barley, triticale, rye, teff, oats, maize, cotton, soy, sorghum, rice, sugarcane and range land (e.g., pasture grasses). In some embodiments, the undesirable vegetation is controlled in a row crop (e.g., maize, sorghum, soybean, cotton, or oilseed rape/canola). In some embodiments, the compositions and methods disclosed herein can be used for controlling undesired vegetation in maize, wheat, rice, barley, or a combination thereof.

The compositions and methods disclosed herein can be used for controlling undesired vegetation in non-crop areas. Exemplary non-crop areas include, but are not limited to, turfgrass, pastures, grasslands, fallow land, rights-of-way, aquatic settings, tree and vine, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, crops that are resistant to photosystem II inhibitors, or crop plants that, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, 4-hydroxyphenyl-pyruvate dioxygenase (HPPD) inhibitors, protoporphyrinogen oxidase (PPO) inhibitors, triazines, and bromoxynil tolerant crops possessing single, multiple or stacked traits conferring tolerance to single or multiple chemistries and/or multiple modes of action. In some embodiments, the undesirable vegetation can be controlled in a crop that is ACCase-tolerant. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

In some embodiments, the compositions disclosed herein can be used for controlling undesirable vegetation including grasses, broadleaf weeds, sedge weeds, and combinations thereof. In some embodiments, the compositions disclosed herein can be used for controlling undesirable vegetation including, but not limited to, *Polygonum* species such as wild buckwheat (*Polygonum convolvulus*), *Alopecurus* species such as blackgrass (*Alopecurus myosuroides*), *Amaranthus* species such as pigweed (*Amaranthus retroflexus*), *Avena* species such as wild oat (*Avena fatua*) *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Cyperus* species such as nutsedge (*Cyperus esculentus*), *Setaria* species such as giant foxtail (*Setaria faberi*), *Sorghum* species, *Acanthospermum* species, *Anthemis* species, *Atriplex* species, *Brassica* species, *Cirsium* species, *Convolvulus* species, *Conyza* species, such as horseweed (*Conyza canadensis*), *Cassia* species, *Commelina* species, *Datura* species, *Digitaria* species such as large crabgrass (*Digitaria sanguinalis*), *Echinola* species such as barnyardgrass (*Echinola crus-galli*) *Euphorbia* species, *Geranium* species, *Galinsoga* species, *Ipomoea* species such as ivyleaf morning-glory (*Ipomoea hederacea*), *Lamium* species, *Malva* species, *Matricaria* species, *Persicaria* species, *Prosopis* species, *Rumex* species, *Sisymbrium* species, *Solanum* species, *Trifolium* species, *Xanthium* species, *Veronica* species, *Viola* species such as wild pansy (*Viola tricolor*), common chickweed (*Stellaria media*), velvetleaf (*Abutilon theophrasti*), hemp *sesbania* (*Sesbania exaltata* Cory), *Anoda cristata, Bidens pilosa, Brassica kaber*, shepherd's purse (*Capsella bursa-pastoris*), cornflower (*Centaurea cyanus* or *Cyanus segetum*). *Galeopsis tetrahit*, cleavers (*Galium aparine*), *Helianthus annuus, Desmodium tortuosum*, kochia (*Kochia scoparia*). *Medicago arabica, Mercurialis annua, Myosotis arvensis*, common poppy (*Papaver rhoeas*), *Raphanus raphanistrum*, Russian thistle (*Salsola kali*), wild mustard (*Sinapis arvensis*), *Sonchus arvensis, Thlaspi arvense, Tagetes minuta, Richardia brasiliensis, Plantago major, Plantago lanceolata*, bird's-eye speedwell (*Veronica persica*) and speedwell.

In certain embodiments, the undesirable vegetation includes velvetleaf (*Abutilon theophrasti*, ABUTH), blackgrass (*Alopecurus mosuroides*, ALOMY), pigweed (*Amaranthus retroflexus*, AMARE), wild oat (*Avena fatua*, AVEFA), brown mustard (*Brassica juncea*, BRSJU), rutabaga (*Brassica napus* var. *napobrassica*. BRSNA), spring rape (*Brassica napus*, BRSNN), winter rape (*Brassica napus*, BRSNW), turnip (*Brassica rapa*, BRSRR), common lambsquarters (*Chenopodium album* L., CHEAL), thistle (*Cirsium arvense* CIRAR), nutsedge (*Cyperus esculentus*, CYPES), large crabgrass (*Digitaria sanguinalis*, DIGSA), barnyardgrass (*Echinochloa crus-galli*, ECHCG), poinsettia (*Euphorbia heterophylla*, EPHHL), soybean (*Glycine max*, GLXMA), sunflower (*Helianthus annuus*, HELAN), ivyleaf morning-glory (*Ipomoea hederacea*, IPOHE), kochia (*Kochia scoparia*, KCHSC), wild buckwheat (*Polygonum convolvulus*, POLCO), giant foxtail (*Setaria fiberi*, SETFA), grain *sorghum* (*Sorghum vulgare*, SORVU), common chickweed (*Stellaria media*, STEME), wild pansy (*Viola tricolor*, VIOTR), or a combination thereof. In certain embodiments, the undesirable vegetation includes poinsettia (*Euphorbia heterophylla*, EPHHL), nutsedge (*Cyperus esculentus*, CYPES), or a combination thereof.

The herbicidal compositions described herein can be used to control herbicide resistant or tolerant weeds. The methods employing the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinyl (oxy/thio)benzoates, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

By way of non-limiting illustration, examples of certain embodiments of the present disclosure are given below.

EXAMPLES

Example 1

Herbicidal Activity and Effect on Crop Injury on Winter Wheat of Compounds of Formula (I) and Triazolopyrimidine Sulfonamide Herbicides in Greenhouse Trials Methodology—Evaluation of Postemergence Herbicidal Activity in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Spray solutions of the experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters (m$^2$) at a spray height of 18 inches (43 centimeters (cm)) above average plant canopy. Control plants were sprayed in the same manner with the solvent blank. Application rates for component (a) are in g ae/ha, and application rates for component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 2 was combined with florasulam and applied to winter wheat (TRZAW) and the phytotoxicity of the herbicidal composition was measured. In addition, the efficacy of the herbicidal composition on poinsettia (*Euphorbia heterophylla*, EPHHL) and water grass (*Cyperus esculentus*, CYPES) was evaluated. The results are summarized in Table 1.

TABLE 1

Effect (% visual injury) of compound 2 and florasulam on weeds.

| | | Application Rate | | | | |
|---|---|---|---|---|---|---|
| Compound 2 (g ae/ha) | | 5 | 10 | 0 | 5 | 10 |
| Florasulam (g ai/ha) | | 0 | 0 | 1.25 | 1.25 | 1.25 |
| EPHHL | Obs | 35 | 75 | 0 | 100 | 90 |
| | Exp | — | — | — | 35 | 75 |
| | Δ | | | | 65 | 15 |
| CYPES | Obs | 5 | 10 | 15 | 18 | 53 |
| | Exp | — | — | — | 19 | 24 |
| | Δ | | | | −2 | 29 |

TABLE 1-continued

Effect (% visual injury) of compound 2 and florasulam on weeds.

| | | Application Rate | | | | |
|---|---|---|---|---|---|---|
| Compound 2 (g ae/ha) | | 5 | 10 | 0 | 5 | 10 |
| Florasulam (g ai/ha) | | 0 | 0 | 1.25 | 1.25 | 1.25 |
| TRZAW | Obs | 3 | 3 | 0 | 0 | 3 |
| | Exp | — | — | — | 3 | 3 |
| | Δ | | | | −3 | 0 | g ae/ha = grams acid equivalent per hectare;
g ai/ha = grams active ingredient per hectare;
EPHHL = *Euphorbia heterophylla* (poinsettia);
CYPES = *Cyperus esculentus* (nutsedge);
TRZAW = *Triticum aestivum* (winter wheat)

Example 2

Herbicidal Activity and Effect on Crop Injury on Winter Wheat, Common Rice and Maize of Compounds of Formula (I) and Triazolopyrimidine Sulfonamide Herbicides in Greenhouse Trials Methodology—Evaluation of Postemergence Herbicidal Activity in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm$^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical or formulated material (emulsifiable concentrate (EC) or soluble concentrate (SL)) were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Spray solutions of the experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters (m$^2$) at a spray height of 18 inches (43 centimeters (cm)) above average plant canopy. Control plants were sprayed in the same manner with the solvent blank. Application rates for component (a) are in g ae/ha, and application rates for component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 1 was formulated as an EC and was combined with florasulam, cloransulam, diclosulam, flumetsulam, penoxsulam, or pyroxsulam. Compound 2 was formulated as an EC and was combined with florasulam or pyroxsulam. The mixtures were applied to winter wheat (TRZAW), common rice (ORYSA), maize (ZEAMX), and the phytotoxicity of the herbicidal compositions was measured. In addition, the efficacy of the herbicidal compositions on blackgrass (*Alopecurus myosuroides*, ALOMY), pigweed (*Amaranthus retroflexus*, AMARE), wild oat (*Avena fatua*, AVEFA), common lambsquarters (*Chenopodium album* L., CHEAL), thistle (*Cirsium arvense* CIRAR), nutsedge (*Cyperus esculentus*, CYPES), barnyardgrass (*Echinochloa crus-galli*, ECHCG), poinsettia (*Euphorbia Heterophylla*, EPHHL), ivyleaf morning-glory (*Ipomoea hederacea*, IPOHE), kochia (*Kochia scoparia*, KCHSC), wild buckwheat (*Polygonum convolvulus*, POLCO), grain sorghum (*Sorghum vulgare*, SORVU), chickweed (*Stellaria media*, STEME), wild pansy (*Viola tricolor*, VIOTR), was evaluated. The results are summarized in Tables 2-9.

TABLE 2

Effect (% visual injury) of compound 2 and florasulam on weeds.

| | | Application Rate | | | | |
|---|---|---|---|---|---|---|
| | | Compound 2 (g ae/ha) | 5 | 10 | 0 | 5 | 10 |
| | | Florasulam (g ai/ha) | 0 | 0 | 1.25 | 1.25 | 1.25 |
| AMARE | Obs | 88 | 100 | 75 | 100 | 100 |
| | Exp | | | | 97 | 100 |
| | Δ | | | | 3 | 0 |
| CHEAL | Obs | 88 | 99 | 0 | 90 | 100 |
| | Exp | | | | 88 | 99 |
| | Δ | | | | 3 | 1 |
| IPOHE | Obs | 10 | 20 | 98 | 100 | 100 |
| | Exp | | | | 98 | 98 |
| | Δ | | | | 2 | 2 |
| ORYSA | Obs | 10 | 18 | 0 | 3 | 13 |
| | Exp | | | | 10 | 18 |
| | Δ | | | | −8 | −5 |
| ZEAMX | Obs | 3 | 3 | 0 | 0 | 3 |
| | Exp | | | | 3 | 3 |
| | Δ | | | | −3 | 0 | g ae/ha = grams acid equivalent per hectare
g ai/ha = grams active ingredient per hectare
AMARE = *Amaranthus retroflexus* (pigweed)
CHEAL = *Chenopodium album* L. (common lambsquarters)
IPOHE = *Ipomoea hederacea* (ivyleaf morning-glory)
ORYSA = *Oryza sativa* (common rice)
ZEAMX = *Zea mays* (maize)

TABLE 3

Effect (% visual injury) of compound 1 and florasulam on weeds.

| | | Application Rate | | |
|---|---|---|---|---|
| | | Compound 1 (g ae/ha) | 5 | 0 | 5 |
| | | Florasulam (g ai/ha) | 0 | 2.5 | 2.5 |
| CYPES | Obs | 10 | 75 | 85 |
| | Exp | | | 78 |
| | Δ | | | 8 |

TABLE 3-continued

Effect (% visual injury) of compound 1 and florasulam on weeds.

| | | Application Rate | | |
|---|---|---|---|---|
| | | Compound 1 (g ae/ha) | 5 | 0 | 5 |
| | | Florasulam (g ai/ha) | 0 | 2.5 | 2.5 |
| KCHSC | Obs | 65 | 60 | 95 |
| | Exp | | | 86 |
| | Δ | | | 9 |
| ORYSA | Obs | 0 | 0 | 0 |
| | Exp | | | 0 |
| | Δ | | | 0 |
| TRZAW | Obs | 5 | 0 | 0 |
| | Exp | | | 5 |
| | Δ | | | −5 |
| ZEAMX | Obs | 0 | 0 | 0 |
| | Exp | | | 0 |
| | Δ | | | 0 | g ae/ha = grams acid equivalent per hectare
g ai/ha = grams active ingredient per hectare
CYPES = *Cyperus esculentus* (nutsedge)
KCHSC = *Kochia scoparia* (kochia)
ORYSA = *Oryza sativa* (common rice)
TRZAW = *Triticum aestivum* (winter wheat)
ZEAMX = *Zea mays* (maize)

TABLE 4

Effect (% visual injury) of compound 1 and cloransulam on weeds.

| | | Application Rate | | |
|---|---|---|---|---|
| | | Compound 1 (g ae/ha) | 5 | 0 | 5 |
| | | Cloransulam (g ai/ha) | 0 | 4.375 | 4.375 |
| AMARE | Obs | 95 | 0 | 100 |
| | Exp | | | 95 |
| | Δ | | | 5 |
| CHEAL | Obs | 80 | 0 | 85 |
| | Exp | | | 80 |
| | Δ | | | 5 |
| CIRAR | Obs | 10 | 99 | 100 |
| | Exp | | | 99 |
| | Δ | | | 1 |
| CYPES | Obs | 10 | 50 | 70 |
| | Exp | | | 55 |
| | Δ | | | 15 |
| EPHHL | Obs | 97 | 30 | 100 |
| | Exp | | | 98 |
| | Δ | | | 2 |
| KCHSC | Obs | 65 | 0 | 90 |
| | Exp | | | 65 |
| | Δ | | | 25 |
| POLCO | Obs | 70 | 85 | 100 |
| | Exp | | | 96 |
| | Δ | | | 5 |
| STEME | Obs | 50 | 0 | 70 |
| | Exp | | | 50 |
| | Δ | | | 20 |
| TRZAW | Obs | 5 | 10 | 0 |
| | Exp | | | 15 |
| | Δ | | | −15 | g ae/ha = grams acid equivalent per hectare
g ai/ha = grams active ingredient per hectare
AMARE = *Amaranthus retroflexus* (pigweed)
CHEAL = *Chenopodium album* L. (common lambsquarters)
CIRAR = *Cirsium arvense* (thistle)
CYPES = *Cyperus esculentus* (nutsedge)
EPHHL = *Euphorbia heterophylla* (poinsettia)
KCHSC = *Kochia scoparia* (kochia)
POLCO = *Polygonum convolvulus* (wild buckwheat)
STEME = *Stellaria media* (chickweed)
TRZAW = *Triticum aestivum* (winter wheat)

TABLE 5

Effect (% visual injury) of compound 1 and diclosulam on weeds.

| | | Application Rate | | |
|---|---|---|---|---|
| | Compound 1 (g ae/ha) | 5 | 0 | 5 |
| | Diclosulam (g ai/ha) | 0 | 4.375 | 4.375 |
| AMARE | Obs | 95 | 60 | 100 |
| | Exp | | | 98 |
| | Δ | | | 2 |
| CHEAL | Obs | 80 | 0 | 85 |
| | Exp | | | 80 |
| | Δ | | | 5 |
| CIRAR | Obs | 10 | 93 | 100 |
| | Exp | | | 94 |
| | Δ | | | 6 |
| CYPES | Obs | 10 | 50 | 60 |
| | Exp | | | 55 |
| | Δ | | | 5 |
| ECHCG | Obs | 50 | 30 | 80 |
| | Exp | | | 65 |
| | Δ | | | 15 |
| EPHHL | Obs | 97 | 60 | 100 |
| | Exp | | | 99 |
| | Δ | | | 1 |
| IPOHE | Obs | 30 | 93 | 100 |
| | Exp | | | 95 |
| | Δ | | | 5 |
| KCHSC | Obs | 65 | 50 | 93 |
| | Exp | | | 83 |
| | Δ | | | 11 |
| STEME | Obs | 50 | 0 | 70 |
| | Exp | | | 50 |
| | Δ | | | 20 |
| TRZAW | Obs | 5 | 0 | 0 |
| | Exp | | | 5 |
| | Δ | | | −5 | g ae/ha = grams acid equivalent per hectare
g ai/ha = grams active ingredient per hectare
AMARE = *Amaranthus retroflexus* (pigweed)
CHEAL = *Chenopodium album* L. (common lambsquarters)
CIRAR = *Cirsium arvense* (thistle)
CYPES = *Cyperus esculentus* (nutsedge)
ECHCG = *Echinochloa crus-galli* (barnyardgrass)
EPHHL = *Euphorbia heterophylla* (poinsettia)
IPOHE = *Ipomoea hederacea* (ivyleaf morning-glory)
KCHSC = *Kochia scoparia* (kochia)
STEME = *Stellaria media* (chickweed)
TRZAW = *Triticum aestivum* (winter wheat)

TABLE 6

Effect (% visual injury) of compound 1 and flumetsulam on weeds.

| | | Application Rate | | |
|---|---|---|---|---|
| | Compound 1 (g ae/ha) | 5 | 0 | 5 |
| | Flumetsulam (g ai/ha) | 0 | 4.375 | 4.375 |
| CIRAR | Obs | 10 | 10 | 65 |
| | Exp | | | 19 |
| | Δ | | | 46 |
| CYPES | Obs | 10 | 10 | 60 |
| | Exp | | | 19 |
| | Δ | | | 41 |
| EPHHL | Obs | 97 | 30 | 100 |
| | Exp | | | 98 |
| | Δ | | | 2 |
| KCHSC | Obs | 65 | 60 | 93 |
| | Exp | | | 86 |
| | Δ | | | 7 |
| SORVU | Obs | 10 | 60 | 65 |
| | Exp | | | 64 |
| | Δ | | | 1 |
| VIOTR | Obs | 30 | 70 | 80 |
| | Exp | | | 79 |
| | Δ | | | 1 |

TABLE 6-continued

Effect (% visual injury) of compound 1 and flumetsulam on weeds.

| | | Application Rate | | |
|---|---|---|---|---|
| | Compound 1 (g ae/ha) | 5 | 0 | 5 |
| | Flumetsulam (g ai/ha) | 0 | 4.375 | 4.375 |
| ORYSA | Obs | 0 | 0 | 0 |
| | Exp | | | 0 |
| | Δ | | | 0 |
| TRZAW | Obs | 5 | 0 | 0 |
| | Exp | | | 5 |
| | Δ | | | −5 | g ae/ha = grams acid equivalent per hectare
g ai/ha = grams active ingredient per hectare
CIRAR = *Cirsium arvense* (thistle)
CYPES = *Cyperus esculentus* (nutsedge)
EPHHL = *Euphorbia heterophylla* (poinsettia)
KCHSC = *Kochia scoparia* (kochia)
SORVU = *Sorghum vulgare* (grain sorghum)
VIOTR = *Viola tricolor* (wild pansy)
ORYSA = *Oryza sativa* (common rice)
TRZAW = *Triticum aestivum* (winter wheat)

TABLE 7

Effect (% visual injury) of compound 2 and pyroxsulam on weeds.

| | | Application Rate | | | | |
|---|---|---|---|---|---|---|
| | Compound 2 (g ae/ha) | 5 | 10 | 0 | 5 | 10 |
| | Pyroxsulam (g ai/ha) | 0 | 0 | 3.75 | 3.75 | 3.75 |
| ALOMY | Obs | 0 | 0 | 10 | 10 | 25 |
| | Exp | | | | 10 | 10 |
| | Δ | | | | 0 | 15 |
| AVEFA | Obs | 0 | 0 | 60 | 65 | 60 |
| | Exp | | | | 60 | 60 |
| | Δ | | | | 5 | 0 |
| CYPES | Obs | 5 | 10 | 23 | 33 | 40 |
| | Exp | | | | 26 | 30 |
| | Δ | | | | 6 | 10 |
| IPOHE | Obs | 10 | 20 | 83 | 68 | 95 |
| | Exp | | | | 84 | 86 |
| | Δ | | | | −17 | 9 |
| ORYSA | Obs | 10 | 18 | 33 | 35 | 30 |
| | Exp | | | | 39 | 44 |
| | Δ | | | | −4 | −14 |
| TRZAW | Obs | 3 | 3 | 0 | 0 | 0 |
| | Exp | | | | 3 | 3 |
| | Δ | | | | −3 | −3 | g ae/ha = grams acid equivalent per hectare
g ai/ha = grams active ingredient per hectare
ALOMY = *Alopecurus myosuroides* (blackgrass)
AVEFA = *Avena fatua* (wild oat)
CYPES = *Cyperus esculentus* (nutsedge)
IPOHE = *Ipomoea hederacea* (ivyleaf morning-glory)
ORYSA = *Oryza sativa* (common rice)
TRZAW = *Triticum aestivum* (winter wheat)

TABLE 8

Effect (% visual injury) of compound 1 and penoxsulam on weeds.

| | | Application Rate | | |
|---|---|---|---|---|
| | Compound 1 (g ae/ha) | 5 | 0 | 5 |
| | Penoxsulam (g ai/ha) | 0 | 5 | 5 |
| CYPES | Obs | 10 | 70 | 90 |
| | Exp | | | 73 |
| | Δ | | | 17 |

TABLE 8-continued

Effect (% visual injury) of compound 1 and penoxsulam on weeds.

| | | Application Rate | | |
|---|---|---|---|---|
| | Compound 1 (g ae/ha) | 5 | 0 | 5 |
| | Penoxsulam (g ai/ha) | 0 | 5 | 5 |
| EPHHL | Obs | 97 | 60 | 100 |
| | Exp | | | 99 |
| | Δ | | | 1 |
| IPOHE | Obs | 30 | 90 | 100 |
| | Exp | | | 93 |
| | Δ | | | 7 |
| KCHSC | Obs | 65 | 10 | 93 |
| | Exp | | | 69 |
| | Δ | | | 25 |
| SORVU | Obs | 10 | 0 | 20 |
| | Exp | | | 10 |
| | Δ | | | 10 |
| ORYSA | Obs | 0 | 0 | 0 |
| | Exp | | | 0 |
| | Δ | | | 0 |
| TRZAW | Obs | 5 | 10 | 0 |
| | Exp | | | 15 |
| | Δ | | | −15 | g ae/ha = grams acid equivalent per hectare
g ai/ha = grams active ingredient per hectare
CYPES = *Cyperus esculentus* (nutsedge)
EPHHL = *Euphorbia heterophylla* (poinsettia)
IPOHE = *Ipomoea hederacea* (ivyleaf morning-glory)
KCHSC = *Kochia scoparia* (kochia)
SORVU = *Sorghum vulgare* (grain sorghum)
ORYSA = *Oryza sativa* (common rice)
TRZAW = *Triticum aestivum* (winter wheat)

TABLE 9

Effect (% visual injury) of compound 1 and pyroxsulam on weeds.

| | | Application Rate | | |
|---|---|---|---|---|
| | Compound 1 (g ae/ha) | 5 | 0 | 5 |
| | Pyroxsulam (g ai/ha) | 0 | 4.6875 | 4.6875 |
| CIRAR | Obs | 10 | 90 | 93 |
| | Exp | | | 91 |
| | Δ | | | 2 |
| CYPES | Obs | 10 | 65 | 75 |
| | Exp | | | 69 |
| | Δ | | | 7 |
| ECHCG | Obs | 50 | 93 | 97 |
| | Exp | | | 97 |
| | Δ | | | 1 |
| IPOHE | Obs | 30 | 95 | 100 |
| | Exp | | | 97 |
| | Δ | | | 4 |
| KCHSC | Obs | 65 | 50 | 95 |
| | Exp | | | 83 |
| | Δ | | | 13 |
| POLCO | Obs | 70 | 85 | 97 |
| | Exp | | | 96 |
| | Δ | | | 2 |
| ORYSA | Obs | | 0 | 30 | 25 |
| | Exp | | | 30 |
| | Δ | | | −5 |

TABLE 9-continued

Effect (% visual injury) of compound 1 and pyroxsulam on weeds.

| | | Application Rate | | |
|---|---|---|---|---|
| | Compound 1 (g ae/ha) | 5 | 0 | 5 |
| | Pyroxsulam (g ai/ha) | 0 | 4.6875 | 4.6875 |
| TRZAW | Obs | 5 | 0 | 0 |
| | Exp | | | 5 |
| | Δ | | | −5 | g ae/ha = grams acid equivalent per hectare
g ai/ha = grams active ingredient per hectare
CIRAR = *Cirsium arvense* (thistle)
CYPES = *Cyperus esculentus* (nutsedge)
ECHCG = *Echinchloa crus-galli* (barnyardgrass)
IPOHE = *Ipomoea hederacea* (ivyleaf morning-glory)
KCHSC = *Kochia scoparia* (kochia)
POLCO = *Polygonum convolvulus* (wild buckwheat)
ORYSA = *Oryza sativa* (common rice)
TRZAW = *Triticum aestivum* (winter wheat)

Example 3

Herbicidal Activity and Effect on Crop Injury on Winter Wheat of Compounds of Formula (I) and Imidazolinone Herbicides in Greenhouse Trials Methodology—Evaluation of Postemergence Herbicidal Activity in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Spray solutions of the experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters (m²) at a spray height of 18 inches (43 centimeters (cm)) above average plant canopy. Control plants were sprayed in the same manner with the solvent blank. Application rates for component (a) are in g ae/ha, and application rates for component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 1 was formulated as an EC and was combined with imazamox, imazamethabenz, imazapic, imazapyr or imazethapyr. The mixtures were applied to winter wheat (TRZAW) and/or maize (ZEAMX), and the phytotoxicity of the herbicidal compositions was measured. In addition, the efficacy of the herbicidal compositions on blackgrass (*Alopecurus myosuroides*, ALOMY), wild oat (*Avena fatua*, AVEFA), winter rape (*Brassica napus*, BRSNW), spring rape (*Brassica napus*, BRSNN), turnip (*Brassica rapa*, BRSRR), thistle (*Cirsium arvense*, CIRAR), large crabgrass (*Digitaria sanguinalis*, DIGSA), pigweed (*Amaranthus retroflexus*, AMARE), common lambsquarters (*Chenopodium album* L., CHEAL), poinsettia (*Euphorbia heterophylla*, EPHHL), ivyleaf morning-glory (*Ipomoea hederacea*, IPOHE), kochia (*Kochia scoparia*, KCHSC), wild buckwheat (*Polygonum convolvulus*, POLCO), grain sorghum (*Sorghum vulgare*, SORVU), chickweed (*Stellaria media*, STEME), wild pansy (*Viola tricolor*, VIOTR), sunflower (*Helianthus annuus*, HELAN), giant foxtail (*Setaria faberi*, SETFA), soybean (*Glycine max*, GLXMA), rutabaga (*Brassica napus* var. *napobrassica*, BRSNA) and barnyardgrass (*Echinochloa crus-galli*, ECHCG) was evaluated. The results are summarized in Tables 10-14.

TABLE 10

Effect (% visual injury) of compound 1 and imazamox on weeds.

| | | Application Rate | | |
|---|---|---|---|---|
| | Compound 1 (g ae/ha) | 5 | 0 | 5 |
| | Imazamox (g ai/ha) | 0 | 11.2 | 11.2 |
| BRSNN | Obs | 50 | 75 | 95 |
| | Exp | | | 88 |
| | Δ | | | 8 |
| BRSRR | Obs | 50 | 70 | 100 |
| | Exp | | | 85 |
| | Δ | | | 15 |
| CIRAR | Obs | 10 | 70 | 85 |
| | Exp | | | 73 |
| | Δ | | | 12 |
| POLCO | Obs | 65 | 65 | 90 |
| | Exp | | | 88 |
| | Δ | | | 2 | g ae/ha = grams acid equivalent per hectare
g ai/ha = grams active ingredient per hectare
BRSNN = *Brassica napus* (spring rape)
BRSRR = *Brassica rapa* (turnip)
CIRAR = *Cirsium arvense* (thistle)
POLCO = *Polygonum convolvulus* (wild buckwheat)

TABLE 11

Effect (% visual injury) of compound 1 and imazethapyr on weeds.

| | | Application Rate | | |
|---|---|---|---|---|
| | Compound 1 (g ae/ha) | 5 | 0 | 5 |
| | Imazethapyr (g ai/ha) | 0 | 17.5 | 17.5 |
| ALOMY | Obs | | 0 | 10 | 20 |
| | Exp | | | | 10 |
| | Δ | | | | 10 |
| AVEFA | Obs | 0 | 10 | 50 |
| | Exp | | | 10 |
| | Δ | | | 40 |
| BRSNW | Obs | 30 | 75 | 95 |
| | Exp | | | 83 |
| | Δ | | | 13 |
| BRSNA | Obs | 65 | 70 | 75 |
| | Exp | | | 72 |
| | Δ | | | 3 |
| CIRAR | Obs | 10 | 30 | 70 |
| | Exp | | | 37 |
| | Δ | | | 33 |
| DIGSA | Obs | 5 | 30 | 70 |
| | Exp | | | 34 |
| | Δ | | | 37 |
| ECHCG | Obs | 70 | 70 | 95 |
| | Exp | | | 91 |
| | Δ | | | 4 |
| VIOTR | Obs | 5 | 5 | 25 |
| | Exp | | | 10 |
| | Δ | | | 15 | g ae/ha = grams acid equivalent per hectare
g ai/ha = grams active ingredient per hectare
ALOMY = *Alopecurus myosuroides* (blackgrass)
AVEFA = *Avena fatua* (wild oat)
BRSNW = *Brassica napus* (winter rape)
BRSNA = *Brassica napus* var. *napobrassica* (rutabaga)
CIRAR = *Cirsium arvense* (thistle)
DIGSA = *Digitaria sanguinalis* (large crabgrass)
ECHCG = *Echinochloa crus-galli* (barnyardgrass)
VIOTR = *Viola tricolor* (wild pansy)

TABLE 12

Effect (% visual injury) of compound 1 and imazamethabenz on weeds.

| | | Application Rate | | | | |
|---|---|---|---|---|---|---|
| | Compound 1 (g ae/ha) | 5 | 10 | 0 | 5 | 10 |
| | Imazamethabenz (g ai/ha) | 0 | 0 | 100 | 100 | 100 |
| AMARE | Obs | 75 | 97 | 0 | 100 | 100 |
| | Exp | | | | 75 | 97 |
| | Δ | | | | 25 | 3 |
| AVEFA | Obs | 0 | 0 | 20 | 40 | 30 |
| | Exp | | | | 20 | 20 |
| | Δ | | | | 20 | 10 |
| BRSNW | Obs | 40 | 45 | 65 | 75 | 90 |
| | Exp | | | | 79 | 81 |
| | Δ | | | | −4 | 9 |
| CHEAL | Obs | 90 | 100 | 20 | 93 | 100 |
| | Exp | | | | 92 | 100 |
| | Δ | | | | 1 | 0 |
| ECHCG | Obs | 20 | 60 | 5 | 30 | 60 |
| | Exp | | | | 24 | 62 |
| | Δ | | | | 6 | −2 |
| EPHHL | Obs | 97 | 97 | 50 | 100 | 100 |
| | Exp | | | | 99 | 99 |
| | Δ | | | | 2 | 2 |
| GLXMA | Obs | 95 | 100 | 30 | 100 | 100 |
| | Exp | | | | 97 | 100 |
| | Δ | | | | 4 | 0 |
| HELAN | Obs | 90 | 90 | 5 | 95 | 95 |
| | Exp | | | | 91 | 91 |
| | Δ | | | | 5 | 5 |

TABLE 12-continued

Effect (% visual injury) of compound 1 and imazamethabenz on weeds.

| | | Application Rate | | | | |
|---|---|---|---|---|---|---|
| | Compound 1 (g ae/ha) | 5 | 10 | 0 | 5 | 10 |
| | Imazamethabenz (g ai/ha) | 0 | 0 | 100 | 100 | 100 |
| IPOHE | Obs | 10 | 10 | 0 | 10 | 20 |
| | Exp | | | | 10 | 10 |
| | Δ | | | | 0 | 10 |
| KCHSC | Obs | 60 | 60 | 0 | 60 | 65 |
| | Exp | | | | 60 | 60 |
| | Δ | | | | 0 | 5 |
| SORVU | Obs | 0 | 50 | 0 | 10 | 30 |
| | Exp | | | | 0 | 50 |
| | Δ | | | | 10 | −20 |
| STEME | Obs | 70 | 70 | 10 | 65 | 75 |
| | Exp | | | | 73 | 73 |
| | Δ | | | | −8 | 2 |
| TRZAW | Obs | 0 | 0 | 0 | 0 | 0 |
| | Exp | | | | 0 | 0 |
| | Δ | | | | 0 | 0 |
| ZEAMX | Obs | 0 | 0 | 0 | 0 | 0 |
| | Exp | | | | 0 | 0 |
| | Δ | | | | 0 | 0 | g ae/ha = grams acid equivalent per hectare;
g ai/ha = grams active ingredient per hectare;
AMARE = *Amaranthus retroflexus* (pigweed);
AVEFA = *Avena fatua* (wild oat);
BRSNW = *Brassica napus* (winter rape);
CHEAL = *Chenopodium album* L. (common lambsquarters);
ECHCG = *Echinochloa crus-galli* (barnyardgrass);
EPHHL = *Euphorbia heterophylla* (poinsettia);
GLXMA = *Glycine Max* (soybean);
HELAN = *Helianthus annuus* (sunflower);
IPOHE = *Ipomoea hederacea* (ivyleaf morning-glory);
KCHSC = *Kochia scoparia* (kochia);
SORVU = *Sorghum vulgare* (grain sorghum);
STEME = *Stellaria media* (chickweed);
TRZAW = *Triticum aestivum* (winter wheat);
ZEAMX = *Zea mays* (maize)

TABLE 13

Effect (% visual injury) of compound 1 and imazapic on weeds.

| | | Application Rate | | | | |
|---|---|---|---|---|---|---|
| | Compound 1 (g ae/ha) | 5 | 10 | 0 | 5 | 10 |
| | Imazapic (g ai/ha) | 0 | 0 | 35 | 35 | 35 |
| AVEFA | Obs | 0 | 0 | 95 | 100 | 97 |
| | Exp | | | | 95 | 95 |
| | Δ | | | | 5 | 2 |
| ECHCG | Obs | 20 | 60 | 93 | 100 | 100 |
| | Exp | | | | 94 | 97 |
| | Δ | | | | 6 | 3 |
| IPOHE | Obs | 10 | 10 | 75 | 100 | 65 |
| | Exp | | | | 78 | 78 |
| | Δ | | | | 23 | −13 |
| SETFA | Obs | 10 | 50 | 90 | 95 | 95 |
| | Exp | | | | 91 | 95 |
| | Δ | | | | 4 | 0 |
| VIOTR | Obs | 5 | 10 | 10 | 20 | 50 |
| | Exp | | | | 15 | 19 |
| | Δ | | | | 6 | 31 | g ae/ha = grams acid equivalent per hectare
g ai/ha = grams active ingredient per hectare
AVEFA = *Avena fatua* (wild oat)
ECHCG = *Echinochloa crus-galli* (barnyardgrass)
IPOHE = *Ipomoea hederacea* (ivyleaf morning-glory)
SETFA = *Setaria faberi* (giant foxtail)
VIOTR = *Viola tricolor* (wild pansy)

TABLE 14

Effect (% visual injury) of compound 1 and imazapyr on weeds.

| | | Application Rate | | | | |
|---|---|---|---|---|---|---|
| | Compound 1 (g ae/ha) | 5 | 10 | 0 | 5 | 10 |
| | Imazapyr (g ai/ha) | 0 | 0 | 280 | 280 | 280 |
| ALOMY | Obs | 0 | 0 | 97 | 100 | 100 |
| | Exp | | | | 97 | 97 |
| | Δ | | | | 3 | 3 |
| DIGSA | Obs | 0 | 10 | 95 | 97 | 97 |
| | Exp | | | | 95 | 96 |
| | Δ | | | | 2 | 2 |
| IPOHE | Obs | 10 | 10 | 85 | 90 | 100 |
| | Exp | | | | 87 | 87 |
| | Δ | | | | 4 | 14 |
| VIOTR | Obs | 5 | 10 | 80 | 85 | 93 |
| | Exp | | | | 81 | 82 |
| | Δ | | | | 4 | 11 | g ae/ha = grams acid equivalent per hectare
g ai/ha = grams active ingredient per hectare
ALOMY = *Alopecurus myosuroides* (blackgrass)
DIGSA = *Digitaria sanguinalis* (large crabgrass)
IPOHE = *Ipomoea hederacea* (ivyleaf morning-glory)
VIOTR = *Viola tricolor* (wild pansy)

Example 4

Herbicidal Activity and Effect on Crop Injury on Winter Wheat or Common Rice of Compounds of Formula (I) and Pyrimidinyl Oxybenzoates Herbicides in Greenhouse Trials Methodology—Evaluation of Postemergence Herbicidal Activity in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Spray solutions of the experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. Application rates for component (a) are in g ae/ha, and application rates for component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 1 was formulated as an EC and was combined with bispyribac-sodium or pyribenzoxim. The mixtures were applied to common rice (ORYSA), and the phytotoxicity of the herbicidal compositions was measured In addition, the efficacy of the herbicidal composition on thistle (*Cirsium arvense*, CIRAR), velvetleaf (*Abutilon theophrasti* ABUTH), large crabgrass (*Digitaria sanguinalis*, DIGSA), ivyleaf morning-glory (*Ipomoea hederacea*, IPOHE), kochia (*Kochia scoparia*, KCHSC), giant foxtail (*Setaria faberi*, SETFA), chickweed (*Stellaria media*, STEME) and wild pansy (*Viola tricolor*, VIOTR) was evaluated. The results are summarized in Tables 15 and 16.

TABLE 15

Effect (% visual injury) of compound 1 and bispyribac-sodium on weeds.

| | | Application Rate | | |
|---|---|---|---|---|
| | Compound 1 (g ae/ha) | 5 | 0 | 5 |
| | Bispyribac-sodium (g ai/ha) | 0 | 10 | 10 |
| CIRAR | Obs | 10 | 95 | 97 |
| | Exp | | | 96 |
| | Δ | | | 2 |
| VIOTR | Obs | 5 | 80 | 90 |
| | Exp | | | 81 |
| | Δ | | | 9 |
| ORYSA | Obs | 5 | 10 | 15 |
| | Exp | | | 15 |
| | Δ | | | 1 | g ae/ha = grams acid equivalent per hectare
g ai/ha = grams active ingredient per hectare
CIRAR = *Cirsium arvense* (thistle)
VIOTR = *Viola tricolor* (wild pansy)
ORYSA = *Oryza sativa* (common rice)

TABLE 16

Effect (% visual injury) of compound 1 and pyribenzoxim on weeds.

| | | Application Rate | | | | |
|---|---|---|---|---|---|---|
| | Compound 1 (g ae/ha) | 5 | 10 | 0 | 5 | 10 |
| | Pyribenzoxim (g ai/ha) | 0 | 0 | 15 | 15 | 15 |
| ABUTH | Obs | 50 | 60 | 10 | 65 | 80 |
| | Exp | | | | 55 | 64 |
| | Δ | | | | 10 | 16 |
| DIGSA | Obs | 0 | 10 | 0 | 0 | 20 |
| | Exp | | | | 0 | 10 |
| | Δ | | | | 0 | 10 |
| IPOHE | Obs | 10 | 10 | 70 | 90 | 93 |
| | Exp | | | | 73 | 73 |
| | Δ | | | | 17 | 20 |
| KCHSC | Obs | 60 | 60 | 0 | 85 | 65 |
| | Exp | | | | 60 | 60 |
| | Δ | | | | 25 | 5 |

TABLE 16-continued

Effect (% visual injury) of compound 1 and pyribenzoxim on weeds.

| | | Application Rate | | | | |
|---|---|---|---|---|---|---|
| | Compound 1 (g ae/ha) | 5 | 10 | 0 | 5 | 10 |
| | Pyribenzoxim (g ai/ha) | 0 | 0 | 15 | 15 | 15 |
| SETFA | Obs | 10 | 50 | 70 | 93 | 80 |
| | Exp | | | | 73 | 85 |
| | Δ | | | | 20 | -5 |
| STEME | Obs | 70 | 70 | 40 | 60 | 90 |
| | Exp | | | | 82 | 82 |
| | Δ | | | | -22 | 8 |
| ORYSA | Obs | 0 | 10 | 0 | 10 | 10 |
| | Exp | | | | 0 | 10 |
| | Δ | | | | 10 | 0 | g ae/ha = grams acid equivalent per hectare
g ai/ha = grams active ingredient per hectare
ABUTH = *Abutilon theophrasti* (velvetleaf)
DIGSA = *Digitaria sanguinalis* (large crabgrass)
IPOHE = *Ipomoea hederacea* (ivyleaf morning-glory)
KCHSC = *Kochia scoparia* (kochia)
SETFA = *Setaria faberi* (giant foxtail)
STEME = *Stellaria media* (chickweed)
ORYSA = *Oryza sativa* (common rice)

Example 5

Herbicidal Activity and Effect on Crop Injury on Winter Wheat of Compounds of Formula (I) and Sulfonylaminocarbonyl Triazolinone Herbicides in Greenhouse Trials Methodology—Evaluation of Postemergence Herbicidal Activity in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Spray solutions of the experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. Application rates for component (a) are in g ae/ha, and application rates for component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 1 was formulated as an EC and was combined with flucarbazone, propoxycarbazone, or thiencarbazone. The mixtures were applied to winter wheat (TRZAW), common rice (*Oryza sativa*, ORYSA) and/or maize (*Zea mays*, ZEAMX), and the phytotoxicity of the herbicidal compositions was measured. In addition, the efficacy of the herbicidal compositions on velvetleaf (*Abutilon theophrasti*, ABUTH), wild oat (*Avena fatua*, AVEFA), common lambsquarters (*Chenopodium album* L., CHEAL), thistle (*Cirsium arvense*, CIRAR), nutsedge (*Cyperus esculentus*, CYPES), large crabgrass (*Digitaria sanguinalis*, DIGSA), barnyardgrass (*Echinochloa crus-galli*, ECHCG), sunflower (*Helianthus annuus*, HELAN), ivyleaf morning-glory (*Ipomoea hederacea*, IPOHE), kochia (*Kochia scoparia*, KCHSC), wild buckwheat (*Polygonum convolvulus*, POLCO), common chickweed (*Stellaria media*, STEME), and wild pansy (*Viola tricolor*, VIOTR) was evaluated. The results are summarized in Tables 17-19.

TABLE 17

Effect (% visual injury) of compound 1 and flucarbazone on weeds.

| | | Application Rate | | |
|---|---|---|---|---|
| | Compound 1 (g ae/ha) | 5 | 0 | 5 |
| | Flucarbazone (g ai/a) | 0 | 7.5 | 7.5 |
| ABUTH | Obs | 70 | 30 | 97 |
| | Exp | | | 79 |
| | Δ | | | 18 |
| CIRAR | Obs | 10 | 85 | 90 |
| | Exp | | | 87 |
| | Δ | | | 4 |
| CYPES | Obs | 10 | 0 | 70 |
| | Exp | | | 10 |
| | Δ | | | 60 |
| DIGSA | Obs | 0 | 60 | 65 |
| | Exp | | | 60 |
| | Δ | | | 5 |
| KCHSC | Obs | 65 | 20 | 90 |
| | Exp | | | 72 |
| | Δ | | | 18 |
| STEME | Obs | 50 | 40 | 85 |
| | Exp | | | 70 |
| | Δ | | | 15 |
| ORYSA | Obs | 0 | 50 | 40 |
| | Exp | | | 50 |
| | Δ | | | −10 |
| TRZAW | Obs | 5 | 10 | 10 |
| | Exp | | | 15 |
| | Δ | | | −5 | g ae/ha = grams acid equivalent per hectare
g ai/ha = grams active ingredient per hectare
ABUTH = *Abutilon theophrasti* (velvetleaf)
CIRAR = *Cirsium arvense* (thistle)
CYPES = *Cyperus esculentus* (nutsedge)
DIGSA = *Digitaria sanguinalis* (large crabgrass)
KCHSC = *Kochia scoparia* (kochia)
STEME = *Stellaria media* (chickweed)
ORYSA = *Oryza sativa* (common rice)
TRZAW = *Triticum aestivum* (winter wheat)

TABLE 18

Effect (% visual injury) of compound 1 and propoxycarbazone on weeds.

| | | Application Rate | | |
|---|---|---|---|---|
| | Compound 1 (g ae/ha) | 5 | 0 | 5 |
| | Propoxycarbazone (g ai/ha) | 0 | 7.5 | 7.5 |
| ABUTH | Obs | 70 | 50 | 95 |
| | Exp | | | 85 |
| | Δ | | | 10 |
| AVEFA | Obs | 0 | 85 | 93 |
| | Exp | | | 85 |
| | Δ | | | 8 |
| CHEAL | Obs | 80 | 30 | 93 |
| | Exp | | | 86 |
| | Δ | | | 7 |
| CIRAR | Obs | 10 | 75 | 93 |
| | Exp | | | 78 |
| | Δ | | | 16 |
| CYPES | Obs | 10 | 75 | 85 |
| | Exp | | | 78 |
| | Δ | | | 8 |
| ECHCG | Obs | 50 | 95 | 100 |
| | Exp | | | 98 |
| | Δ | | | 3 |
| HELAN | Obs | 90 | 85 | 100 |
| | Exp | | | 99 |
| | Δ | | | 2 |
| IPOHE | Obs | 30 | 95 | 100 |
| | Exp | | | 97 |
| | Δ | | | 4 |
| KCHSC | Obs | 65 | 30 | 90 |
| | Exp | | | 76 |
| | Δ | | | 15 |
| POLCO | Obs | 70 | 10 | 100 |
| | Exp | | | 73 |
| | Δ | | | 27 |
| STEME | Obs | 50 | 50 | 97 |
| | Exp | | | 75 |
| | Δ | | | 22 |
| VIOTR | Obs | 30 | 20 | 60 |
| | Exp | | | 44 |
| | Δ | | | 16 |
| TRZAW | Obs | 5 | 10 | 10 |
| | Exp | | | 15 |
| | Δ | | | −5 | g ae/ha = grams acid equivalent per hectare;
g ai/ha = grams active ingredient per hectare;
ABUTH = *Abutilon theophrasti* (velvetleaf);
AVEFA = *Avena fatua* (wild oat);
CHEAL = *Chenopodium album* L. (common lambsquarters);
CIRAR = *Cirsium arvense* (thistle);
CYPES = *Cyperus esculentus* (nutsedge);
ECHCG = *Echinochloa crus-galli* (barnyardgrass);
HELAN = *Helianthus annuus* (sunflower);
IPOHE = *Ipomoea hederacea* (ivyleaf morning-glory);
KCHSC = *Kochia scoparia* (kochia);
POLCO = *Polygonum convolvulus* (wild buckwheat);
STEME = *Stellaria media* (common chickweed);
VIOTR = *Viola tricolor* (wild pansy);
TRZAW = *Triticum aestivum* (winter wheat)

TABLE 19

Effect (% visual injury) of compound 1 and thiencarbazone on weeds.

| | | Application Rate | | |
|---|---|---|---|---|
| | Compound 1 (g ae/ha) | 5 | 0 | 5 |
| | Thiencarbazone (g ai/ha) | 0 | 5 | 5 |
| CIRAR | Obs | 10 | 50 | 80 |
| | Exp | | | 55 |
| | Δ | | | 25 |
| CYPES | Obs | 10 | 70 | 80 |
| | Exp | | | 73 |
| | Δ | | | 7 |

TABLE 19-continued

Effect (% visual injury) of compound 1 and thiencarbazone on weeds.

|  |  | Application Rate | | |
|---|---|---|---|---|
|  |  | Compound 1 (g ae/ha) | 5 | 0 | 5 |
|  |  | Thiencarbazone (g ai/ha) | 0 | 5 | 5 |
| KCHSC | Obs | 65 | 10 | 93 |
|  | Exp |  |  | 69 |
|  | Δ |  |  | 25 |
| STEME | Obs | 50 | 95 | 100 |
|  | Exp |  |  | 98 |
|  | Δ |  |  | 3 |
| TRZAW | Obs | 5 | 0 | 0 |
|  | Exp |  |  | 5 |
|  | Δ |  |  | −5 |
| ZEAMX | Obs | 0 | 10 | 10 |
|  | Exp |  |  | 10 |
|  | Δ |  |  | 0 | g ae/ha = grams acid equivalent per hectare
g ai/ha = grams active ingredient per hectare
CIRAR = *Cirsium arvense* (thistle)
CYPES = *Cyperus esculentus* (nutsedge)
KCHSC = *Kochia scoparia* (kochia)
STEME = *Stellaria media* (chickweed)
TRZAW = *Triticum aestivum* (winter wheat)
ZEAMX = *Zea mays* (maize)

Example 6

Herbicidal Activity and Effect on Crop Injury on Winter Wheat, Common Rice and Maize of Compounds of Formula (I) and Sulfonylurea Herbicides in Greenhouse Trials Methodology—Evaluation of Postemergence Herbicidal Activity in Crops: Greenhouse Trials Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Spray solutions of the experimental compound mixtures were prepared by adding the stock solutions to the appropriate amount of dilution solution to form a 12 mL spray solution in two- and three-way combinations. Formulated compounds were applied to the plant material with an overhead Mandel track sprayer equipped with 8002E nozzles calibrated to deliver 187 L/ha over an application area of 0.503 square meters (m²) at a spray height of 18 inches (43 centimeters (cm)) above average plant canopy. Control plants were sprayed in the same manner with the solvent blank. Application rates for component (a) are in g ae/ha, and application rates for component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 1 was formulated as an EC and was combined with amidosulfuron, azimsulfuron, bensulfuron, ethoxysulfuron, foramsulfuron chlorsulfuron, flupyrsulfuron, halosulfuron, iodosulfuron, mesosulfuron, metsulfuron, nicosulfuron, orthosulfamuron, sulfosulfuron, thifensulfuron, or tribenuron, and Compound 1 was formulated as an EC and was combined with mesosulfuron+iodosulfuron or thifensulfuron+tribenuron. The mixtures were applied to winter wheat (TRZAW), maize (ZEAMX) and/or common rice (ORYSA), and the phytotoxicity of the herbicidal compositions was measured. In addition, the efficacy of the herbicidal compositions on velvetleaf (*Abutilon theophrasti*, ABUTH), blackgrass (*Alopecurus myosuroides*, ALOMY), pigweed (*Amaranthus retroflexus*, AMARE), brown mustard (*Brassica juncea*, BRSJU), spring rape (*Brassica napus*, BRSNN), winter rape (*Brassica napus*, BRSNW), lambsquarters (*Chenopodium album* L., CHEAL), thistle (*Cirsium arvense* CIRAR), nutsedge (*Cyperus esculentus*, CYPES), barnyardgrass (*Echinochloa crus-galli*, ECHCG), poinsettia (*Euphorbia heterophylla*, EPHHL), common sunflower (*Helianthus annuus*, HELAN), ivyleaf morning-glory (*Ipomoea hederacea*, IPOHE), kochia (*Kochia scoparia*, KCHSC), wild buckwheat (*Polygonum convolvulus*, POLCO), giant foxtail (*Setaria faberi*, SETFA), grain sorghum (*Sorghum vulgare*, SORVU), common chickweed (*Stellaria media*, STEME), wild pansy (*Viola tricolor*, VIOTR) and was evaluated. The results are summarized in Tables 20-38.

TABLE 20

Effect (% visual injury) of compound 1 and amidosulfuron on weeds.

|  |  | Application Rate | | |
|---|---|---|---|---|
|  |  | Compound 1 (g ae/ha) | 5 | 0 | 5 |
|  |  | Amidosulfuron (g ai/ha) | 0 | 7.5 | 7.5 |
| CIRAR | Obs | 10 | 20 | 70 |
|  | Exp |  |  | 28 |
|  | Δ |  |  | 42 |
| CYPES | Obs | 10 | 20 | 50 |
|  | Exp |  |  | 28 |
|  | Δ |  |  | 22 |
| ECHCG | Obs | 50 | 0 | 70 |
|  | Exp |  |  | 50 |
|  | Δ |  |  | 20 |
| IPOHE | Obs | 30 | 35 | 65 |
|  | Exp |  |  | 55 |
|  | Δ |  |  | 11 |
| KCHSC | Obs | 65 | 10 | 75 |
|  | Exp |  |  | 69 |
|  | Δ |  |  | 7 |
| POLCO | Obs | 70 | 85 | 100 |
|  | Exp |  |  | 96 |
|  | Δ |  |  | 5 |

TABLE 20-continued

Effect (% visual injury) of compound 1 and amidosulfuron on weeds.

|  |  | Application Rate | | |
|---|---|---|---|---|
|  | Compound 1 (g ae/ha) | 5 | 0 | 5 |
|  | Amidosulfuron (g ai/ha) | 0 | 7.5 | 7.5 |
| ORYSA | Obs | 0 | 0 | 0 |
|  | Exp |  |  | 0 |
|  | Δ |  |  | 0 |
| TRZAW | Obs | 5 | 0 | 10 |
|  | Exp |  |  | 5 |
|  | Δ |  |  | 5 |
| ZEAMX | Obs | 0 | 0 | 10 |
|  | Exp |  |  | 0 |
|  | Δ |  |  | 10 | g ae/ha = grams acid equivalent per hectare
g ai/ha = grams active ingredient per hectare
CIRAR = *Cirsium arvense* (thistle)
CYPES = *Cyperus esculentus* (nutsedge)
ECHCG = *Echinochloa crus-galli* (barnyardgrass)
IPOHE = *Ipomoea hederacea* (ivyleaf morning-glory)
KCHSC = *Kochia scoparia* (kochia)
POLCO = *Polygonum convolvulus* (wild buckwheat)
ORYSA = *Oryza sativa* (common rice)
TRZAW = *Triticum aestivum* (winter wheat)
ZEAMX = *Zea mays* (maize)

TABLE 21

Effect (% visual injury) of compound 1 and azimsulfuron on weeds.

|  |  | Application Rate | | | | |
|---|---|---|---|---|---|---|
|  | Compound 1 (g ae/ha) | 5 | 10 | 0 | 5 | 10 |
|  | Azimsulfuron (g ai/ha) | 0 | 0 | 6.25 | 6.25 | 6.25 |
| CHEAL | Obs | 90 | 100 | 10 | 95 | 93 |
|  | Exp |  |  |  | 91 | 100 |
|  | Δ |  |  |  | 4 | −7 |
| EPHHL | Obs | 97 | 97 | 10 | 100 | 100 |
|  | Exp |  |  |  | 97 | 97 |
|  | Δ |  |  |  | 3 | 3 |
| IPOHE | Obs | 10 | 10 | 93 | 97 | 100 |
|  | Exp |  |  |  | 94 | 94 |
|  | Δ |  |  |  | 3 | 6 |
| KCHSC | Obs | 60 | 60 | 0 | 65 | 70 |
|  | Exp |  |  |  | 60 | 60 |
|  | Δ |  |  |  | 5 | 10 |
| SORVU | Obs | 0 | 50 | 65 | 70 | 80 |
|  | Exp |  |  |  | 63 | 83 |
|  | Δ |  |  |  | 5 | −3 |
| STEME | Obs | 70 | 70 | 20 | 95 | 85 |
|  | Exp |  |  |  | 76 | 76 |
|  | Δ |  |  |  | 19 | 9 |
| VIOTR | Obs | 5 | 10 | 60 | 70 | 75 |
|  | Exp |  |  |  | 62 | 64 |
|  | Δ |  |  |  | 8 | 11 |
| ORYSA | Obs | 0 | 10 | 0 | 0 | 0 |
|  | Exp |  |  |  | 0 | 10 |
|  | Δ |  |  |  | 0 | −10 |
| TRZAW | Obs | 0 | 0 | 0 | 0 | 0 |
|  | Exp |  |  |  | 0 | 0 |
|  | Δ |  |  |  | 0 | 0 | g ae/ha = grams acid equivalent per hectare
g ai/ha = grams active ingredient per hectare
CHEAL = *Chenopodium album* L. (common lambsquarters)
EPHHL = *Euphorbia heterophylla* (poinsettia)
IPOHE = *Ipomoea hederacea* (ivyleaf morning-glory)
KCHSC = *Kochia scoparia* (kochia)
SORVU = *Sorghum vulgare* (grain sorghum)
STEME = *Stellaria media* (chickweed)
VIOTR = *Viola tricolor* (wild pansy)
ORYSA = *Oryza sativa* (common rice)
TRZAW = *Triticum aestivum* (winter wheat)

TABLE 22

Effect (% visual injury) of compound 1 and bensulfuron on weeds.

|  |  | Application Rate | | |
|---|---|---|---|---|
|  | Compound 1 (g ae/ha) | 5 | 0 | 5 |
|  | Bensulfuron (g ai/ha) | 0 | 17.5 | 17.5 |
| BRSJU | Obs | 60 | 93 | 100 |
|  | Exp |  |  | 97 |
|  | Δ |  |  | 3 |
| BRSNW | Obs | 50 | 70 | 93 |
|  | Exp |  |  | 85 |
|  | Δ |  |  | 8 |
| HELAN | Obs | 70 | 10 | 100 |
|  | Exp |  |  | 73 |
|  | Δ |  |  | 27 |
| VIOTR | Obs | 5 | 0 | 10 |
|  | Exp |  |  | 5 |
|  | Δ |  |  | 5 |
| ORYSA | Obs | 5 | 0 | 0 |
|  | Exp |  |  | 5 |
|  | Δ |  |  | −5 |
| TRZAW | Obs | 5 | 0 | 10 |
|  | Exp |  |  | 5 |
|  | Δ |  |  | 5 | g ae/ha = grams acid equivalent per hectare
g ai/ha = grams active ingredient per hectare
BRSJU = *Brassica juncea* (brown mustard)
BRSNW = *Brassica napus* (winter rape)
HELAN = *Helianthus annuus* (sunflower)
VIOTR = *Viola tricolor* (wild pansy)
ORYSA = *Oryza sativa* (common rice)
TRZAW = *Triticum aestivum* (winter wheat)

TABLE 23

Effect (% visual injury) of compound 1 and chlorsulfuron on weeds.

|  |  | Application Rate | | |
|---|---|---|---|---|
|  | Compound 1 (g ae/ha) | 5 | 0 | 5 |
|  | Chlorsulfuron (g ai/ha) | 0 | 2.2 | 2.2 |
| BRSNN | Obs | 70 | 93 | 100 |
|  | Exp |  |  | 98 |
|  | Δ |  |  | 2 |
| CHEAL | Obs | 80 | 90 | 100 |
|  | Exp |  |  | 98 |
|  | Δ |  |  | 2 |
| CIRAR | Obs | 10 | 90 | 95 |
|  | Exp |  |  | 91 |
|  | Δ |  |  | 4 |
| CYPES | Obs | 10 | 0 | 50 |
|  | Exp |  |  | 10 |
|  | Δ |  |  | 40 |
| ECHCG | Obs | 50 | 0 | 60 |
|  | Exp |  |  | 50 |
|  | Δ |  |  | 10 |
| VIOTR | Obs | 30 | 60 | 75 |
|  | Exp |  |  | 72 |
|  | Δ |  |  | 3 |
| KCHSC | Obs | 65 | 50 | 85 |
|  | Exp |  |  | 83 |
|  | Δ |  |  | 3 |
| ORYSA | Obs | 0 | 0 | 0 |
|  | Exp |  |  | 0 |
|  | Δ |  |  | 0 |

TABLE 23-continued

Effect (% visual injury) of compound 1 and chlorsulfuron on weeds.

| | | Application Rate | | |
|---|---|---|---|---|
| | | Compound 1 (g ae/ha) | 5 | 0 | 5 |
| | | Chlorsulfuron (g ai/ha) | 0 | 2.2 | 2.2 |
| TRZAW | Obs | 5 | 0 | 0 |
| | Exp | | | 5 |
| | Δ | | | −5 | g ae/ha = grams acid equivalent per hectare
g ai/ha = grams active ingredient per hectare
BRSNN = *Brassica napus* (spring rape)
CHEAL = *Chenopodium album* L. (common lambsquarters)
CIRAR = *Cirsium arvense* (thistle)
CYPES = *Cyperus esculentus* (nutsedge)
ECHCG = *Echinochloa crus-galli* (barnyardgrass)
VIOTR = *Viola tricolor* (wild pansy)
KCHSC = *Kochia scoparia* (kochia)
ORYSA = *Oryza sativa* (common rice)
TRZAW = *Triticum aestivum* (winter wheat)

TABLE 24

Effect (% visual injury) of compound 1 and ethoxysulfuron on weeds.

| | | Application Rate | | | | |
|---|---|---|---|---|---|---|
| | | Compound 1 (g ae/ha) | 5 | 10 | 0 | 5 | 10 |
| | | Ethoxysulfuron (g ai/ha) | 0 | 0 | 10 | 10 | 10 |
| AMARE | Obs | 75 | 97 | 20 | 97 | 97 |
| | Exp | | | | 80 | 98 |
| | Δ | | | | 17 | −1 |
| KCHSC | Obs | 60 | 60 | 0 | 65 | 65 |
| | Exp | | | | 60 | 60 |
| | Δ | | | | 5 | 5 |
| STEME | Obs | 70 | 70 | 10 | 40 | 90 |
| | Exp | | | | 73 | 73 |
| | Δ | | | | −33 | 17 |
| VIOTR | Obs | 5 | 10 | 40 | 50 | 55 |
| | Exp | | | | 43 | 46 |
| | Δ | | | | 7 | 9 |
| ORYSA | Obs | 0 | 10 | 5 | 0 | 0 |
| | Exp | | | | 5 | 15 |
| | Δ | | | | −5 | −15 |
| TRZAW | Obs | 0 | 0 | 0 | 0 | 0 |
| | Exp | | | | 0 | 0 |
| | Δ | | | | 0 | 0 |
| ZEAMX | Obs | 0 | 0 | 0 | 0 | 0 |
| | Exp | | | | 0 | 0 |
| | Δ | | | | 0 | 0 | g ae/ha = grams acid equivalent per hectare
g ai/ha = grams active ingredient per hectare
AMARE = *Amaranthus retroflexus* (pigweed)
KCHSC = *Kochia scoparia* (kochia)
STEME = *Stellaria media* (chickweed)
VIOTR = *Viola tricolor* (wild pansy)
ORYSA = *Oryza sativa* (common rice)
TRZAW = *Triticum aestivum* (winter wheat)
ZEAMX = *Zea mays* (maize)

TABLE 25

Effect (% visual injury) of compound 1 and foramsulfuron on weeds.

| | | Application Rate | | | | |
|---|---|---|---|---|---|---|
| | | Compound 1 (g ae/ha) | 5 | 10 | 0 | 5 | 10 |
| | | Foramsulfuron (g ai/ha) | 0 | 0 | 10 | 10 | 10 |
| ALOMY | Obs | 0 | 0 | 93 | 100 | 95 |
| | Exp | | | | 93 | 93 |
| | Δ | | | | 7 | 2 |

TABLE 25-continued

Effect (% visual injury) of compound 1 and foramsulfuron on weeds.

| | | Application Rate | | | | |
|---|---|---|---|---|---|---|
| | | Compound 1 (g ae/ha) | 5 | 10 | 0 | 5 | 10 |
| | | Foramsulfuron (g ai/ha) | 0 | 0 | 10 | 10 | 10 |
| AMARE | Obs | 75 | 97 | 85 | 100 | 90 |
| | Exp | | | | 96 | 100 |
| | Δ | | | | 4 | −10 |
| ORYSA | Obs | 0 | 10 | 70 | 75 | 70 |
| | Exp | | | | 70 | 73 |
| | Δ | | | | 5 | −3 |
| TRZAW | Obs | 0 | 0 | 97 | 97 | 97 |
| | Exp | | | | 97 | 97 |
| | Δ | | | | 0 | 0 |
| ZEAMX | Obs | 0 | 0 | 0 | 0 | 0 |
| | Exp | | | | 0 | 0 |
| | Δ | | | | 0 | 0 | g ae/ha = grams acid equivalent per hectare
g ai/ha = grams active ingredient per hectare
ALOMY = *Alopecurus myosuroides* (blackgrass)
AMARE = *Amaranthus retroflexus* (pigweed)
ORYSA = *Oryza sativa* (common rice)
TRZAW = *Triticum aestivum* (winter wheat)
ZEAMX = *Zea mays* (maize)

TABLE 26

Effect (% visual injury) of compound 1 and flupyrsulfuron on weeds.

| | | Application Rate | | |
|---|---|---|---|---|
| | | Compound 1 (g ae/ha) | 5 | 0 | 5 |
| | | Flupyrsulfuron (g ai/ha) | 0 | 5 | 5 |
| ABUTH | Obs | 70 | 80 | 97 |
| | Exp | | | 94 |
| | Δ | | | 3 |
| CIRAR | Obs | 10 | 75 | 95 |
| | Exp | | | 78 |
| | Δ | | | 18 |
| CYPES | Obs | 10 | 70 | 85 |
| | Exp | | | 73 |
| | Δ | | | 12 |
| KCHSC | Obs | 65 | 10 | 95 |
| | Exp | | | 69 |
| | Δ | | | 7 |
| ORYSA | Obs | 0 | 0 | 0 |
| | Exp | | | 0 |
| | Δ | | | 0 |
| TRZAW | Obs | 5 | 0 | 5 |
| | Exp | | | 5 |
| | Δ | | | 0 | g ae/ha = grams acid equivalent per hectare
g ai/ha = grams active ingredient per hectare
ABUTH = *Abutilon theophrasti* (velvetleaf)
CIRAR = *Cirsium arvense* (thistle)
CYPES = *Cyperus esculentus* (nutsedge)
KCHSC = *Kochia scoparia* (kochia)
ORYSA = *Oryza sativa* (common rice)
TRZAW = *Triticum aestivum* (winter wheat)

TABLE 27

Effect (% visual injury) of compound 1 and halosulfuron on weeds.

| | | Application Rate | | |
|---|---|---|---|---|
| | | Compound 1 (g ae/ha) | 5 | 0 | 5 |
| | | Halosulfuron (g ai/ha) | 0 | 8.75 | 8.75 |
| CIRAR | Obs | 10 | 10 | 60 |
| | Exp | | | 19 |
| | Δ | | | 41 |

TABLE 27-continued

Effect (% visual injury) of compound 1 and halosulfuron on weeds.

|  |  | Application Rate | | |
|---|---|---|---|---|
|  | Compound 1 (g ae/ha) | 5 | 0 | 5 |
|  | Halosulfuron (g ai/ha) | 0 | 8.75 | 8.75 |
| POLCO | Obs | 65 | 30 | 93 |
|  | Exp |  |  | 76 |
|  | Δ |  |  | 18 |
| ORYSA | Obs | 5 | 0 | 0 |
|  | Exp |  |  | 5 |
|  | Δ |  |  | −5 |
| TRZAW | Obs | 5 | 0 | 0 |
|  | Exp |  |  | 5 |
|  | Δ |  |  | −5 |
| ZEAMX | Obs | 0 | 0 | 0 |
|  | Exp |  |  | 0 |
|  | Δ |  |  | 0 | g ae/ha = grams acid equivalent per hectare
g ai/ha = grams active ingredient per hectare
CIRAR = *Cirsium arvense* (thistle)
ORYSA = *Oryza sativa* (common rice)
POLCO = *Polygonum convolvulus* (wild buckwheat)
TRZAW = *Triticum aestivum* (winter wheat)
ZEAMX = *Zea mays* (maize)

TABLE 28

Effect (% visual injury) of compound 1 and halosulfuron on weeds.

|  |  | Application Rate | | | | |
|---|---|---|---|---|---|---|
|  | Compound 1 (g ae/ha) | 5 | 10 | 0 | 5 | 10 |
|  | Halosulfuron (g ai/ha) | 0 | 0 | 17.5 | 17.5 | 17.5 |
| AMARE | Obs | 75 | 97 | 30 | 97 | 100 |
|  | Exp |  |  |  | 83 | 98 |
|  | Δ |  |  |  | 15 | 2 |
| IPOHE | Obs | 10 | 10 | 20 | 40 | 70 |
|  | Exp |  |  |  | 28 | 28 |
|  | Δ |  |  |  | 12 | 42 |
| KCHSC | Obs | 60 | 60 | 0 | 70 | 80 |
|  | Exp |  |  |  | 60 | 60 |
|  | Δ |  |  |  | 10 | 20 |
| STEME | Obs | 70 | 70 | 50 | 40 | 100 |
|  | Exp |  |  |  | 85 | 85 |
|  | Δ |  |  |  | −45 | 15 |
| ORYSA | Obs | 0 | 10 | 0 | 0 | 10 |
|  | Exp |  |  |  | 0 | 10 |
|  | Δ |  |  |  | 0 | 0 |
| TRZAW | Obs | 0 | 0 | 0 | 10 | 0 |
|  | Exp |  |  |  | 0 | 0 |
|  | Δ |  |  |  | 10 | 0 |
| ZEAMX | Obs | 0 | 0 | 0 | 0 | 0 |
|  | Exp |  |  |  | 0 | 0 |
|  | Δ |  |  |  | 0 | 0 | g ae/ha = grams acid equivalent per hectare
g ai/ha = grams active ingredient per hectare
AMARE = *Amaranthus retroflexus* (pigweed)
IPOHE = *Ipomoea hederacea* (ivyleaf morning-glory)
KCHSC = *Kochia scoparia* (kochia)
STEME = *Stellaria media* (chickweed)
ORYSA = *Oryza sativa* (common rice)
TRZAW = *Triticum aestivum* (winter wheat)
ZEAMX = *Zea mays* (maize)

TABLE 29

Effect (% visual injury) of compound 1 and iodosulfuron on weeds.

|  |  | Application Rate | | |
|---|---|---|---|---|
|  | Compound 1 (g ae/ha) | 5 | 0 | 5 |
|  | Iodosulfuron (g ai/ha) | 0 | 2.5 | 2.5 |
| POLCO | Obs | 75 | 80 | 100 |
|  | Exp | — | — | 94 |
|  | Δ |  |  | 6 |
| TRZAW | Obs | 5 | 0 | 0 |
|  | Exp | — | — | 5 |
|  | Δ |  |  | −5 |
| ZEAMX | Obs | 0 | 0 | 0 |
|  | Exp | — | — | 0 |
|  | Δ |  |  | 0 | g ae/ha = grams acid equivalent per hectare
g ai/ha = grams active ingredient per hectare
POLCO = *Polygonum convolvulus* (wild buckwheat)
TRZAW = *Triticum aestivum* (winter wheat)
ZEAMX = *Zea mays* (maize)

TABLE 30

Effect (% visual injury) of compound 1 and mesosulfuron on weeds.

|  |  | Application Rate | | |
|---|---|---|---|---|
|  | Compound 1 (g ae/ha) | 5 | 0 | 5 |
|  | Mesosulfuron (g ai/ha) | 0 | 3 | 3 |
| KCHSC | Obs | 65 | 10 | 85 |
|  | Exp |  |  | 69 |
|  | Δ |  |  | 17 |
| POLCO | Obs | 70 | 20 | 100 |
|  | Exp |  |  | 76 |
|  | Δ |  |  | 24 |
| SORVU | Obs | 10 | 97 | 100 |
|  | Exp |  |  | 97 |
|  | Δ |  |  | 3 |
| ORYSA | Obs | 0 | 10 | 10 |
|  | Exp |  |  | 10 |
|  | Δ |  |  | 0 |
| TRZAW | Obs | 5 | 0 | 10 |
|  | Exp |  |  | 5 |
|  | Δ |  |  | 5 | g ae/ha = grams acid equivalent per hectare
g ai/ha = grams active ingredient per hectare
KCHSC = *Kochia scoparia* (kochia)
POLCO = *Polygonum convolvulus* (wild buckwheat)
SORVU = *Sorghum vulgare* (grain sorghum)
ORYSA = *Oryza sativa* (common rice)
TRZAW = *Triticum aestivum* (winter wheat)

TABLE 31

Effect (% visual injury) of compound 1 and mesosulfuron + iodosulfuron on weeds.

|  |  | Application Rate | | |
|---|---|---|---|---|
|  | Compound 1 (g ae/ha) | 5 | 0 | 5 |
|  | Mesosulfuron + Iodosulfuron (g ai/ha) | 0 | 2.5 | 2.5 |
| CIRAR | Obs |  | 10 | 93 | 97 |
|  | Exp |  |  | 94 |
|  | Δ |  |  | 3 |
| STEME | Obs |  | 50 | 70 | 90 |
|  | Exp |  |  | 85 |
|  | Δ |  |  | 5 |
| ORYSA | Obs |  | 0 | 10 | 0 |
|  | Exp |  |  | 10 |
|  | Δ |  |  | −10 |

TABLE 31-continued

Effect (% visual injury) of compound 1 and mesosulfuron + iodosulfuron on weeds.

| | | Application Rate | | |
|---|---|---|---|---|
| | Compound 1 (g ae/ha) | 5 | 0 | 5 |
| | Mesosulfuron + Iodosulfuron (g ai/ha) | 0 | 2.5 | 2.5 |
| TRZAW | Obs | 5 | 5 | 0 |
| | Exp | | | 10 |
| | Δ | | | −10 | g ae/ha = grams acid equivalent per hectare
g ai/ha = grams active ingredient per hectare
CIRAR = *Cirsium arvense* (thistle)
STEME = *Stellaria media* (chickweed)
ORYSA = *Oryza sativa* (common rice)
TRZAW = *Triticum aestivum* (winter wheat)

TABLE 32

Effect (% visual injury) of compound 1 and metsulfuron on weeds.

| | | Application Rate | | |
|---|---|---|---|---|
| | Compound 1 (g ae/ha) | 5 | 0 | 5 |
| | Metsulfuron (g ai/ha) | 0 | 1.5 | 1.5 |
| CIRAR | Obs | 10 | 90 | 97 |
| | Exp | | | 91 |
| | Δ | | | 6 |
| CYPES | Obs | 10 | 50 | 70 |
| | Exp | | | 55 |
| | Δ | | | 15 |
| ECHCG | Obs | 50 | 0 | 60 |
| | Exp | | | 50 |
| | Δ | | | 10 |
| KCHSC | Obs | 65 | 70 | 93 |
| | Exp | | | 90 |
| | Δ | | | 4 |
| ORYSA | Obs | 0 | 20 | 10 |
| | Exp | | | 20 |
| | Δ | | | −10 |
| TRZAW | Obs | 5 | 0 | 0 |
| | Exp | | | 5 |
| | Δ | | | −5 | g ae/ha = grams acid equivalent per hectare
g ai/ha = grams active ingredient per hectare
CIRAR = *Cirsium arvense* (thistle)
CYPES = *Cyperus esculentus* (nutsedge)
ECHCG = *Echinochloa crus-galli* (barnyardgrass)
KCHSC = *Kochia scoparia* (kochia)
ORYSA = *Oryza sativa* (common rice)
TRZAW = *Triticum aestivum* (winter wheat)

TABLE 33

Effect (% visual injury) of compound 1 and nicosulfuron on weeds.

| | | Application Rate | | | | |
|---|---|---|---|---|---|---|
| | Compound 1 (g ae/ha) | 5 | 10 | 0 | 5 | 10 |
| | Nicosulfuron (g ai/ha) | 0 | 0 | 17.5 | 17.5 | 17.5 |
| BRSNW | Obs | 40 | 45 | 85 | 93 | 97 |
| | Exp | | | | 91 | 92 |
| | Δ | | | | 2 | 5 |
| IPOHE | Obs | 10 | 10 | 30 | 95 | 100 |
| | Exp | | | | 37 | 37 |
| | Δ | | | | 58 | 63 |
| KCHSC | Obs | 60 | 60 | 5 | 65 | 70 |
| | Exp | | | | 62 | 62 |
| | Δ | | | | 3 | 8 |
| SETFA | Obs | 10 | 50 | 80 | 100 | 90 |
| | Exp | | | | 82 | 90 |
| | Δ | | | | 18 | 0 |
| STEME | Obs | 70 | 70 | 30 | 30 | 95 |
| | Exp | | | | 79 | 79 |
| | Δ | | | | −49 | 16 |
| VIOTR | Obs | 5 | 10 | 40 | 50 | 30 |
| | Exp | | | | 43 | 46 |
| | Δ | | | | 7 | −16 |
| ZEAMX | Obs | 0 | 0 | 0 | 0 | 5 |
| | Exp | | | | 0 | 0 |
| | Δ | | | | 0 | 5 | g ae/ha = grams acid equivalent per hectare
g ai/ha = grams active ingredient per hectare
BRSNW = *Brassica napus* (winter rape)
IPOHE = *Ipomoea hederacea* (ivyleaf morning-glory)
KCHSC = *Kochia scoparia* (kochia)
SETFA = *Setaria faberi* (giant foxtail)
STEME = *Stellaria media* (chickweed)
VIOTR = *Viola tricolor* (wild pansy)
ZEAMX = *Zea mays* (maize)

TABLE 34

Effect (% visual injury) of compound 1 and orthosulfamuron on weeds.

| | | Application Rate | | | | |
|---|---|---|---|---|---|---|
| | Compound 1 (g ae/ha) | 5 | 10 | 0 | 5 | 10 |
| | Orthosulfamuron (g ai/ha) | 0 | 0 | 15 | 15 | 15 |
| AMARE | Obs | 75 | 97 | 10 | 90 | 100 |
| | Exp | | | | 78 | 97 |
| | Δ | | | | 13 | 3 |
| IPOHE | Obs | 10 | 10 | 90 | 93 | 100 |
| | Exp | | | | 91 | 91 |
| | Δ | | | | 2 | 9 |
| KCHSC | Obs | 60 | 60 | 0 | 65 | 73 |
| | Exp | | | | 60 | 60 |
| | Δ | | | | 5 | 13 |
| ORYSA | Obs | 0 | 10 | 0 | 0 | 0 |
| | Exp | | | | 0 | 10 |
| | Δ | | | | 0 | −10 |
| TRZAW | Obs | 0 | 0 | 0 | 5 | 5 |
| | Exp | | | | 0 | 0 |
| | Δ | | | | 5 | 5 | g ae/ha = grams acid equivalent per hectare
g ai/ha = grams active ingredient per hectare
AMARE = *Amaranthus retroflexus* (pigweed)
IPOHE = *Ipomoea hederacea* (ivyleaf morning-glory)
KCHSC = *Kochia scoparia* (kochia)
ORYSA = *Oryza sativa* (common rice)
TRZAW = *Triticum aestivum* (winter wheat)

TABLE 35

Effect (% visual injury) of compound 1 and sulfosulfuron on weeds.

| | | Application Rate | | |
|---|---|---|---|---|
| | Compound 1 (g ae/ha) | 5 | 0 | 5 |
| | Sulfosulfuron g ai/ha | 0 | 8.75 | 8.75 |
| CIRAR | Obs | 10 | 85 | 90 |
| | Exp | | | 87 |
| | Δ | | | 4 |
| CYPES | Obs | 10 | 80 | 85 |
| | Exp | | | 82 |
| | Δ | | | 3 |

TABLE 35-continued

Effect (% visual injury) of compound 1 and sulfosulfuron on weeds.

|  |  | Application Rate | | |
|---|---|---|---|---|
|  | Compound 1 (g ae/ha) | 5 | 0 | 5 |
|  | Sulfosulfuron g ai/ha | 0 | 8.75 | 8.75 |
| POLCO | Obs | 70 | 80 | 100 |
|  | Exp |  |  | 94 |
|  | Δ |  |  | 6 |
| VIOTR | Obs | 30 | 80 | 95 |
|  | Exp |  |  | 86 |
|  | Δ |  |  | 9 |
| ORYSA | Obs | 0 | 10 | 0 |
|  | Exp |  |  | 10 |
|  | Δ |  |  | −10 |
| TRZAW | Obs | 5 | 0 | 0 |
|  | Exp |  |  | 5 |
|  | Δ |  |  | −5 |
| ZEAMX | Obs | 0 | 0 | 10 |
|  | Exp |  |  | 0 |
|  | Δ |  |  | 10 | g ae/ha = grams acid equivalent per hectare
g ai/ha = grams active ingredient per hectare
CIRAR = *Cirsium arvense* (thistle)
CYPES = *Cyperus esculentus* (nutsedge)
POLCO = *Polygonum convolvulus* (wild buckwheat)
VIOTR = *Viola tricolor* (wild pansy)
ORYSA = *Oryza sativa* (common rice)
TRZAW = *Triticum aestivum* (winter wheat)
ZEAMX = *Zea mays* (maize)

TABLE 36

Effect (% visual injury) of compound 1 and thifensulfuron on weeds.

|  |  | Application Rate | | |
|---|---|---|---|---|
|  | Compound 1 (g ae/ha) | 5 | 0 | 5 |
|  | Thifensulfuron (g ai/ha) | 0 | 15 | 15 |
| CIRAR | Obs | 10 | 10 | 75 |
|  | Exp |  |  | 19 |
|  | Δ |  |  | 56 |
| CYPES | Obs | 10 | 0 | 60 |
|  | Exp |  |  | 10 |
|  | Δ |  |  | 50 |
| ECHCG | Obs | 50 | 10 | 60 |
|  | Exp |  |  | 55 |
|  | Δ |  |  | 5 |
| IPOHE | Obs | 30 | 85 | 100 |
|  | Exp |  |  | 90 |
|  | Δ |  |  | 11 |
| ORYSA | Obs | 0 | 10 | 10 |
|  | Exp |  |  | 10 |
|  | Δ |  |  | 0 |
| TRZAW | Obs | 5 | 0 | 0 |
|  | Exp |  |  | 5 |
|  | Δ |  |  | −5 |
| ZEAMX | Obs | 0 | 0 | 0 |
|  | Exp |  |  | 0 |
|  | Δ |  |  | 0 | g ae/ha = grams acid equivalent per hectare
g ai/ha = grams active ingredient per hectare
CIRAR = *Cirsium arvense* (thistle)
CYPES = *Cyperus esculentus* (nutsedge)
ECHCG = *Echinochloa crus-galli* (barnyardgrass)
IPOHE = *Ipomoea hederacea* (ivyleaf morning-glory)
ORYSA = *Oryza sativa* (common rice)
TRZAW = *Triticum aestivum* (winter wheat)
ZEAMX = *Zea mays* (maize)

TABLE 37

Effect (% visual injury) of compound 1 and thifensulfuron + tribenuron on weeds.

|  |  | Application Rate | | |
|---|---|---|---|---|
|  | Compound 1 (g ae/ha) | 5 | 0 | 5 |
|  | Thifensulfuron + Tribenuron (g ai/ha) | 0 | 15 | 15 |
| CYPES | Obs | 10 | 0 | 60 |
|  | Exp |  |  | 10 |
|  | Δ |  |  | 50 |
| KCHSC | Obs | 65 | 50 | 97 |
|  | Exp |  |  | 83 |
|  | Δ |  |  | 15 |
| ORYSA | Obs | 0 | 0 | 0 |
|  | Exp |  |  | 0 |
|  | Δ |  |  | 0 |
| TRZAW | Obs | 5 | 0 | 0 |
|  | Exp |  |  | 5 |
|  | Δ |  |  | −5 | g ae/ha = grams acid equivalent per hectare
g ai/ha = grams active ingredient per hectare
CYPES = *Cyperus esculentus* (nutsedge)
KCHSC = *Kochia scoparia* (kochia)
ORYSA = *Oryza sativa* (common rice)
TRZAW = *Triticum aestivum* (winter wheat)

TABLE 38

Effect (% visual injury) of compound 1 and tribenuron on weeds.

|  |  | Application Rate | | |
|---|---|---|---|---|
|  | Compound 1 (g ae/ha) | 5 | 0 | 5 |
|  | Tribenuron (g ai/ha) | 0 | 7.5 | 7.5 |
| CYPES | Obs | 10 | 0 | 70 |
|  | Exp |  |  | 10 |
|  | Δ |  |  | 60 |
| IPOHE | Obs | 30 | 65 | 100 |
|  | Exp |  |  | 76 |
|  | Δ |  |  | 25 |
| KCHSC | Obs | 65 | 70 | 100 |
|  | Exp |  |  | 90 |
|  | Δ |  |  | 11 |
| POLCO | Obs | 70 | 90 | 100 |
|  | Exp |  |  | 97 |
|  | Δ |  |  | 3 |
| ORYSA | Obs | 0 | 10 | 0 |
|  | Exp |  |  | 10 |
|  | Δ |  |  | −10 |
| TRZAW | Obs | 5 | 0 | 0 |
|  | Exp |  |  | 5 |
|  | Δ |  |  | −5 | g ae/ha = grams acid equivalent per hectare
g ai/ha = grams active ingredient per hectare
CYPES = *Cyperus esculentus* (nutsedge)
IPOHE = *Ipomoea hederacea* (ivyleaf morning-glory)
KCHSC = *Kochia scoparia* (kochia)
POLCO = *Polygonum convolvulus* (wild buckwheat)
ORYSA = *Oryza sativa* (common rice)
TRZAW = *Triticum aestivum* (winter wheat)

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a herbicidally effective amount of (a) a pyridine carboxylic acid herbicide or an agriculturally acceptable N-oxide, salt, or ester thereof, and (b) an acetolactate synthase (ALS) inhibitor selected from the group consisting of florasulam, cloransulam, diclosulam, flumetsulam, penoxsulam, pyroxsulam, imazamethabenz, imazamox, imazapic, imazapyr, imazethapyr, bispyribac, pyribenzoxim, flucarbazone, propoxycarbazone, thiencarbazone, amidosulfuron, azimsulfuron, bensulfuron, chlorsulfuron, ethoxysulfuron, flupyrsulfuron, foramsulfuron, halosulfuron, iodosulfuron, mesosulfuron, metsulfuron, nicosulfuron, orthosulfamuron, sulfosulfuron, thifensulfuron, or an agriculturally acceptable salts and esters thereof, and combinations thereof, wherein (a) and (b) are provided in a weight ratio of (a) in grams acid equivalent to (b) in grams active ingredient of from 1:56 to 8:1, and wherein the pyridine carboxylic acid herbicide comprises a compound defined by the formula below

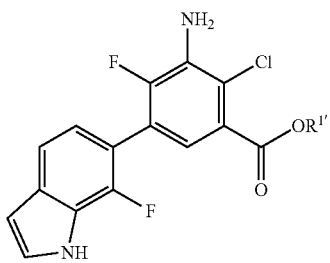

wherein $R^{1'}$ is hydrogen, or substituted or unsubstituted $C_7-C_{10}$ arylalkyl;

or an agriculturally acceptable N-oxide or salt thereof.

2. The composition of claim 1, wherein the pyridine carboxylic acid herbicide comprises one of the following:

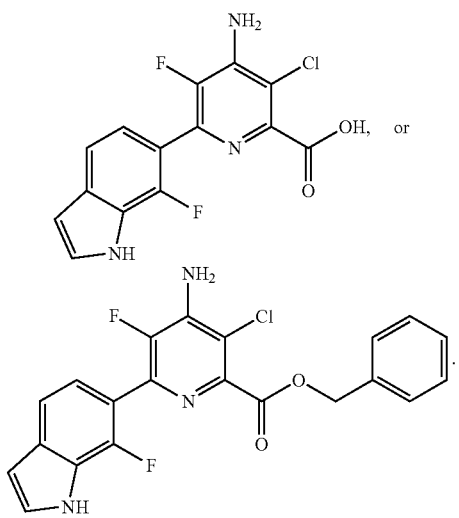

3. The composition of claim 1, wherein the pyridine carboxylic acid herbicide comprises

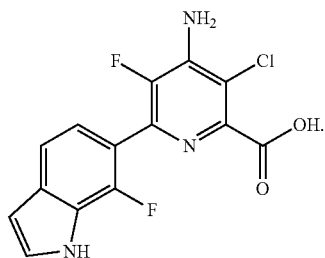 [SMILES: Nc1c(F)c(-c2ccc3cc[nH]c3c2F)nc(C(=O)O)c1Cl]

4. The composition of claim 1, wherein (b) is a triazolopyrimidine sulfonamide herbicide selected from the group consisting of florasulam, cloransulam, diclosulam, flumetsulam, penoxsulam, pyroxsulam, agriculturally acceptable salts and esters thereof, and combinations thereof.

5. The composition of claim 4, wherein the weight ratio of (a) to (b) is from 1:10 to 8:1.

6. The composition of claim 1, wherein (b) is an imidazolinone herbicide selected from the group consisting of imazamethabenz, imazamox, imazapic, imazapyr, imazethapyr, agriculturally acceptable salts and esters thereof, and combinations thereof.

7. The composition of claim 6, wherein the weight ratio of (a) to (b) is from 1:50 to 8:1.

8. The composition of claim 1, wherein (b) is a pyrimidinyl oxybenzoate herbicide selected from the group consisting of bispyribac, pyribenzoxim, agriculturally acceptable salts and esters thereof, and combinations thereof.

9. The composition of claim 8, wherein the weight ratio of (a) to (b) is from 1:10 to 5:1.

10. The composition of claim 1, wherein (b) is a sulfonylaminocarbonyl triazolinone herbicide selected from the group consisting of flucarbazone, propoxycarbazone, thiencarbazone, agriculturally acceptable salts and esters thereof, and combinations thereof.

11. The composition of claim 10, wherein the weight ratio of (a) to (b) is from 1:10 to 5:1.

12. The composition of claim 1, wherein (b) is a sulfonylurea herbicide selected from the group consisting of amidosulfuron, azimsulfuron, bensulfuron, chlorsulfuron, ethoxysulfuron, flupyrsulfuron, foramsulfuron, halosulfuron, iodosulfuron, mesosulfuron, metsulfuron, nicosulfuron, orthosulfamuron, sulfosulfuron, thifensulfuron, agriculturally acceptable salts and esters thereof, and combinations thereof.

13. The composition of claim 12, wherein the weight ratio of (a) to (b) is from 1:20 to 5:1.

14. The composition of claim 1, further comprising an agriculturally acceptable adjuvant or carrier.

15. The composition of claim 1, further comprising an additional pesticide.

16. The composition of claim 1, wherein the active ingredients in the composition consist of (a) and (b).

17. The composition of claim 1, wherein the composition is provided as a herbicidal concentrate.

18. The composition of claim 1, wherein $R^{1'}$ is hydrogen.

19. The composition of claim 1, wherein $R^{1'}$ is a substituted or unsubstituted $C_8$ arylalkyl group.

20. The composition of claim 1, wherein $R^{1'}$ is a benzyl group.

21. The composition of claim 1, wherein (b) is propoxycarbazone.

22. The composition of claim 1, wherein (b) is thiencarbazone.

23. The composition of claim 1, wherein (b) is iodosulfuron.

24. The composition of claim 1, wherein (b) is mesosulfuron.

25. The composition of claim 1, wherein (b) is a combination of mesosulfuron and iodosulfuron.

26. A method of controlling undesirable vegetation comprising applying to vegetation or an area adjacent the vegetation or applying to soil or water to control the emergence or growth of vegetation a herbicidally effective amount of the composition of claim 1.

27. The method of claim 26, wherein (a) is applied in amount of from 0.1 g ae/ha to 300 g ae/ha.

28. The method of claim 26, wherein (b) is applied in amount of from 0.25 g ai/ha to 1700 g ai/ha.

29. The method of claim 26, wherein (a) and (b) are applied post-emergence to the undesirable vegetation.

30. The method of claim 26, further comprising applying an additional pesticide.

31. The method of claim 26, wherein the undesirable vegetation includes a broadleaf weed.

32. The method of claim 26, wherein the undesirable vegetation comprises a herbicide resistant or tolerant weed.

33. The method of claim 26, wherein the undesirable vegetation includes velvetleaf, blackgrass, pigweed, wild oat, brown mustard, rutabaga, spring rape, winter rape, turnip, lambsquarters, thistle, nutsedge, large crabgrass, barnyardgrass, poinsettia, soybean, sunflower, ivyleaf morning-glory, *kochia*, wild buckwheat, giant foxtail, sorghum, common chickweed, wild pansy, or a combination thereof.

34. The method of claim 26, wherein the active ingredients applied to the vegetation or an area adjacent the vegetation or applied to soil or water to control the emergence or growth of vegetation consist of (a) and (b).

* * * * *

UNITED STATES PATENT AND TRADEMARK OFFICE
CERTIFICATE OF CORRECTION

PATENT NO. : 10,448,638 B2  
APPLICATION NO. : 14/854684  
DATED : October 22, 2019  
INVENTOR(S) : Norbert M. Satchivi et al.

Page 1 of 1

It is certified that error appears in the above-identified patent and that said Letters Patent is hereby corrected as shown below:

In the Claims

Claim 1 at Column 143, Lines 40-41 should read:
"...orthosulfamuron, sulfosulfuron, thifensulfuron, agriculturally acceptable salts and esters thereof, and..."

Signed and Sealed this  
Twenty-first Day of January, 2020

Andrei Iancu  
*Director of the United States Patent and Trademark Office*